(12) United States Patent
Chambers et al.

(10) Patent No.: US 6,900,209 B2
(45) Date of Patent: May 31, 2005

(54) NITROGEN SUBSTITUTED 1,2,4-TRIAZOLO [3,4-A]PHTHALAZINE DERIVATIVES FOR ENHANCING COGNITION

(75) Inventors: Mark Stuart Chambers, Puckeridge (GB); Philip Jones, Pomezia (IT); Angus Murray MacLeod, Bishops Stortford (GB); Robert James Maxey, Amersham (GB); Helen Jane Szekeres, Roydon (GB)

(73) Assignee: Merck sharp & Dohme Ltd., Hoddesdon ( * ) Notice: Subject to any disclaimer, the term of this patent is extended or adjusted under 35 U.S.C. 154(b) by 0 days.

(21) Appl. No.: 10/432,391

(22) PCT Filed: Nov. 22, 2001

(86) PCT No.: PCT/GB01/05164
§ 371 (c)(1),
(2), (4) Date: May 21, 2003

(87) PCT Pub. No.: WO02/42305
PCT Pub. Date: May 30, 2002

(65) Prior Publication Data
US 2004/0043982 A1 Mar. 4, 2004

(30) Foreign Application Priority Data
Nov. 23, 2000 (GB) .............................................. 0028583

(51) Int. Cl.$^7$ .................. C07D 487/04; A61K 31/5025; A61P 25/28
(52) U.S. Cl. ....................... 514/248; 544/234; 544/111; 514/233.2
(58) Field of Search ................................ 544/234, 111; 514/248, 233.2

(56) References Cited

U.S. PATENT DOCUMENTS

| | | | |
|---|---|---|---|
| 4,788,186 A | 11/1988 | Occelli et al. | |
| 5,145,684 A | 9/1992 | Liversidge | |
| 5,182,290 A | 1/1993 | Albaugh | |
| 5,212,310 A | 5/1993 | Thurkauf et al. | |
| 5,306,819 A | 4/1994 | Albaugh | |
| 6,200,975 B1 * | 3/2001 | Carling et al. | 514/248 |

FOREIGN PATENT DOCUMENTS

| | | | |
|---|---|---|---|
| DE | 196 17 862 | | 10/1997 |
| EP | 0 085 840 | | 8/1983 |
| EP | 0 134 946 | | 3/1985 |
| WO | WO 96/25948 | | 8/1996 |
| WO | WO 98/04559 | | 2/1998 |
| WO | WO 98/50385 A | * | 11/1998 |
| WO | WO 99/06407 A | * | 2/1999 |

OTHER PUBLICATIONS

G. Tarzia et al., "Benzodiazepine ReceptorLigands, Synthesis and Preliminary Pharmacological Evaluation . . . ", Farmaco, Edizione Scientifica, vol. 43, No. 2, pp. 189–201, XP 002041885.

Cai, Dongwei et al., "A Study of the Lithiation of 2,6–Dibromopyridine with Butyllithium, and its Application to Synthesis of L–739,010", Tetrahedron Letters, vol. 37, No. 15, pp. 2537–2540 (1996).

McNamara, Robert, K. et al., "Benzodiazepine receptor antagonists flumazenil and CGS 8216 and inverse–agonist β–CCM enhance spatial learning in the rat: Dissociation from anxiogenic actions", Psychobiology, Vo. 21, No. 2, pp. 101–101 (1993).

* cited by examiner

Primary Examiner—Venkataraman Balasubramanian
(74) Attorney, Agent, or Firm—John C. Todaro; Melvin Winokur

(57) ABSTRACT

The present invention provides a compound of formula (I) wherein A is an optionally substituted $C_{1-4}$alkylidene group or a bond, $R^{20}$ and $R^{21}$ are hydrogen, alkyl groups or heterocyclic groups, $R^1$ and $R^2$ are small substituents or hydrogen, L is O, S or substituted N, X is a 5- or 6-membered heteroaromatic ring, Y is $C_{1-4}$alkylidene and Z is a 5- or 6-membered heteroaromatic ring; or a pharmaceutically acceptable salt thereof; pharmaceutical compositions comprising it; its use in therapy; its use in making medicaments for treating neurodegenerative disease and methods of using it to enhance cognition.

10 Claims, No Drawings

NITROGEN SUBSTITUTED 1,2,4-TRIAZOLO [3,4-A]PHTHALAZINE DERIVATIVES FOR ENHANCING COGNITION

CROSS REFERENCE TO RELATED APPLICATIONS

This application is a U.S. National Phase application under 35 U.S.C. § 371 of PCT Application No. PCT/GB01/05164, filed Nov. 22, 2001, which claims priority under 35 U.S.C. § 119 from GB Application No. 0028583.3, filed Nov. 23, 2000.

The present invention relates to a class of substituted triazolo-phthalazine derivatives and to their use in therapy. More particularly, this invention is concerned with nitrogen substituted 1,2,4-triazolo[3,4-α]phthalazine derivatives which are ligands for $GABA_A$ receptors containing the α5 subunit and are therefore useful in the therapy where cognition enhancement is required.

Receptors for the major inhibitory neurotransmitter, gamma-aminobutyric acid (GABA), are divided into two main classes: (1) $GABA_A$ receptors, which are members of the ligand-gated ion channel superfamily; and (2) $GABA_B$ receptors, which may be members of the G-protein linked receptor superfamily. Since the first cDNAs encoding individual $GABA_A$ receptor subunits were cloned the number of known members of the mammalian family has grown to thirteen (six α subunits, three β subunits, three γ subunits and one δ subunit). It may be that further subunits remain to be discovered; however, none has been reported since 1993.

Although knowledge of the diversity of the $GABA_A$ receptor gene family represents a huge step forward in our understanding of this ligand-gated ion channel, insight into the extent of subtype diversity is still at an early stage. It has been indicated that an α subunit, a β subunit and a γ subunit constitute the minimum requirement for forming a fully functional $GABA_A$ receptor expressed by transiently transfecting cDNAs into cells. As indicated above, a δ subunit also exists, but is apparently uncommon in the native receptor.

Studies of receptor size and visualisation by electron microscopy conclude that, like other members of the ligand-gated ion channel family, the native $GABA_A$ receptor exists in pentameric form. The selection of at least one α, one β and one γ subunit from a repertoire of thirteen allows for the possible existence of more than 10,000 pentameric subunit combinations. Moreover, this calculation overlooks the additional permutations that would be possible if the arrangement of subunits around the ion channel had no constraints (i.e. there could be 120 possible variants for a receptor composed of five different subunits).

Receptor subtype assemblies which do exist include α1β2γ2, α2β2/3γ2, α3βγ2/3, α2βγ1, α5β3γ2/3, α6βγ2, α6βδ and α4βδ. Subtype assemblies containing an α1 subunit are present in most areas of the brain and account for over 40% of $GABA_A$ receptors in the rat. Subtype assemblies containing α2 and α3 subunits respectively account for about 25% and 17% of $GABA_A$ receptors in the rat. Subtype assemblies containing an α5 subunit are primarily hippocampal and represent about 4% of receptors in the rat.

A characteristic property of some $GABA_A$ receptors is the presence of a number of modulatory sites, of which the most explored is the benzodiazepine (BZ) binding site through which anxiolytic drugs such as diazepam and temazepam exert their effect. Before the cloning of the $GABA_A$ receptor gene family, the benzodiazepine binding site was historically subdivided into two subtypes, BZ1 and BZ2, on the basis of radioligand binding studies. The BZ1 subtype has been shown to be pharmacologically equivalent to a $GABA_A$ receptor comprising the α1 subunit in combination with β2 and γ2. This is the most abundant $GABA_A$ receptor subtype, representing almost half of all $GABA_A$ receptors in the brain.

A number of dementing illnesses such as Alzheimer's disease are characterised by a progressive deterioration in cognition in the sufferer. It would clearly be desirable to enhance cognition in subjects desirous of such treatment, for example for subjects suffering from a dementing illness.

It has been reported by McNamara and Skelton in Psychobiology, 21:101–108, that the benzodiazepine receptor inverse agonist β-CCM enhanced spatial learning in the Morris watermaze. However, β-CCM and other conventional benzodiazepine receptor inverse agonists are proconvulsant or convulsant which makes it clear that they cannot be used as cognition enhancing agents in humans.

However, we have now discovered that it is possible to obtain medicaments which have cognition enhancing effects which may be employed with less risk of proconvulsant effects previously described with benzodiazepine receptor partial or full inverse agonists.

It has now been discovered that use of an α5 receptor partial or full inverse agonist which is relatively free of activity at α1 and/or α2 and/or α3 receptor binding sites can be used to provide a medicament which is useful for enhancing cognition but in which proconvulsant activity is reduced or eliminated. Inverse agonists at α5 which are not free of activity at α1 and/or α2 and/or α3 but which are functionally selective for α5 can also be used. Inverse agonists which are both selective for α5 and are relatively free of activity at α1, α2 and α3 receptor binding sites are preferred.

WO-A-9850385 describes a related series of 1,2,4-triazolo[3,4-α]phthalazine derivatives which are stated to possess cognition enhancing activity. However, there is no disclosure nor any suggestion in either of the publications of the compounds of the present invention, which have advantageous solubility. Compared to such compounds those of the present invention generally have improved pharmacokinetics, such as improved volume of distribution.

The present invention provides a compound of the formula I:

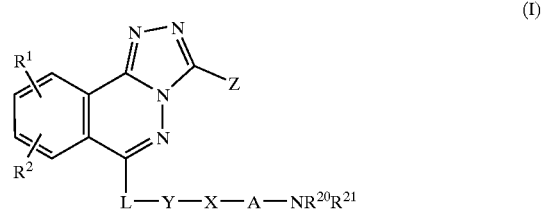

(I)

wherein:

A is a $C_{1-4}$alkylidene group optionally substituted with one or more $C_{1-4}$alkyl, halogen or hydroxy groups in which case $R^{20}$ and $R^{21}$ are independently chosen from hydrogen, $C_{1-10}$alkyl, $C_{3-6}$cycloalkyl, $C_{5-6}$cycloalkenyl, $C_{2-10}$alkenyl, $C_{2-10}$alkynyl, amino$C_{1-10}$alkyl, $C_{1-6}$alkylamino$C_{1-10}$alkyl, di($C_{1-6}$alkyl)amino$C_{1-10}$alkyl and phenyl$C_{1-10}$alkyl, or $R^{20}$ and $R^{21}$, together with the nitrogen atom to which they are attached, form an unsaturated 4–7 membered heterocyclic ring optionally containing a further nitrogen atom or an oxygen atom, or a 5 or 6 membered heteroaromatic ring containing one, two or three further heteroatoms chosen from O, N and S, at most one of the heteroatoms being O or S, may be substituted with one or two groups chosen from halogen, hydroxy, $C_{1-6}$alkyl, $CF_3$, CN, amino and nitro or $R^{20}$ and/or $R^{21}$, together with A and the nitrogen to which $R^{20}$ and/or $R^{21}$ is attached, form a 4–7 membered heterocyclic ring optionally containing a further nitrogen or oxygen atom, $R^{20}$ and $R^{21}$ being optionally substituted with one, two or three groups chosen from halogen, hydroxy, $C_{1-6}$alkyl, $CF_3$, CN, amino, C(O)H, carboxy and $CO_2C_{1-6}$alkyl;

alternatively A is a bond in which case $R^{20}$ and $R^{21}$, together with the nitrogen atom to which they are attached, form a 4–7 membered saturated heterocyclic ring containing a further nitrogen or oxygen atom, or a partially saturated heterocyclic ring optionally containing a further nitrogen or oxygen atom, $R^{20}$ and $R^{21}$ being optionally substituted with one, two or three groups chosen from halogen, hydroxy, $C_{1-6}$alkyl, $CF_3$, CN, amino, nitro, C(O)H, carboxy and $CO_2C_{1-6}$alkyl;

$R^1$ is hydrogen, halogen or CN or a group $CF_3$, $OCF_3$, $C_{1-4}$alkyl, $C_{2-4}$alkenyl, $C_{2-4}$alkynyl, $C_{1-4}$alkoxy, $C_{2-4}$alkenyloxy or $C_{2-4}$alkyloxy, each of which groups is unsubstituted or substituted with one or two halogen atoms or with a pyridyl or phenyl ring each of which rings may be unsubstituted or independently substituted by one or two halogen atoms or nitro, cyano, amino, methyl or $CF_3$ groups;

$R^2$ is hydrogen, halogen or CN or a group $CF_3$, $OCF_3$, $C_{1-4}$alkyl, $C_{2-4}$alkenyl, $C_{2-4}$alkynyl, $C_{1-4}$alkoxy, $C_{2-4}$alkenyloxy or $C_{2-4}$alkynyloxy each of which groups is unsubstituted or substituted with one or two halogen atoms;

L is O, S or $NR^n$ where $R^n$ is H, $C_{1-6}$alkyl or $C_{3-6}$cycloalkyl;

X is a 5-membered heteroaromatic ring containing 1, 2, 3 or 4 heteroatoms independently chosen from oxygen, nitrogen and sulphur, at most one of the heteroatoms being oxygen or sulphur, or a 6-membered heteroaromatic ring containing 1, 2 or 3 nitrogen atoms, the 5- or 6-membered heteroaromatic ring being optionally fused to a benzene ring and the heteroaromatic ring being optionally substituted by $R^x$ and/or $R^y$ and/or $R^z$, where $R^x$ is halogen, $R^3$, $OR^3$, $OCOR^3$, $NR^4R^5$, $NR^4COR^5$, tri($C_{1-6}$alkyl)silyl$C_{1-6}$alkoxy$C_{1-4}$alkyl, CN or $R^9$, $R^y$ is halogen, $R^3$, $OR^3$, $OCOR^3$, $NR^4R^5$, $NR^4COR^5$ or CN and $R^z$ is $R^3$, $OR^3$ or $OCOR^3$, where $R^3$ is $C_{1-6}$alkyl, $C_{2-6}$alkenyl, $C_{2-6}$alkynyl, $C_{3-6}$cycloalkyl, hydroxy$C_{1-6}$alkyl and $R^3$ is optionally mono-, di- or tri-fluorinated, $R^4$ and $R^5$ are each independently hydrogen, $C_{1-6}$alkyl, $C_{2-6}$alkenyl, $C_{2-6}$alkynyl, $C_{3-6}$cycloalkyl or $CF_3$ or $R^4$ and $R^5$, together with the nitrogen atom to which they are attached, form a 4–7 membered heteroaliphatic ring containing the nitrogen atom as the sole heteroatom, and $R^9$ is benzyl or an aromatic ring containing either 6 atoms, 1, 2 or 3 of which are optionally nitrogen, or 5 atoms, 1, 2 or 3 of which are independently chosen from oxygen, nitrogen and sulphur, at most one of the atoms being oxygen or sulphur, and $R^9$ is optionally substituted by one, two or three substituents independently chosen from halogen atoms and $C_{1-4}$alkyl, $C_{2-4}$alkenyl, $C_{2-4}$alkynyl, $C_{1-4}$alkoxy, $C_{2-4}$alkenyloxy and $C_{2-4}$alkynyloxy groups each of which groups is unsubstituted or substituted by one, two or three halogen atoms, and when X is a pyridine derivative, the pyridine derivative is optionally in the form of the N-oxide and providing that when X is a tetrazole derivative it is protected by a $C_{1-4}$alkyl group; or X is phenyl optionally substituted by one, two or three groups independently selected from halogen, cyano, $C_{1-6}$alkyl, $C_{2-6}$alkenyl, $C_{2-6}$alkynyl and $C_{3-6}$cycloalkyl;

Y is optionally branched $C_{1-4}$alkylidene optionally substituted by an oxo group or Y is a group $(CH_2)_jO$ wherein the oxygen atom is nearest the group X and j is 2, 3 or 4;

Z is a 5-membered heteroaromatic ring containing 1, 2 or 3 heteroatoms independently selected from oxygen, nitrogen and sulphur, at most one of the heteroatoms being oxygen or sulphur and providing that when one of the atoms is oxygen or sulphur then at least one nitrogen atom is present, or a 6-membered heteroaromatic ring containing 2 or 3 nitrogen atoms, Z being optionally substituted by $R^v$ and/or $R^w$, where $R^v$ is halogen, $R^6$, $NR^7R^8$, $NR^7COR^8$, CN, furyl, thienyl, phenyl, benzyl, pyridyl or a 5-membered heteroaromatic ring containing at least one nitrogen atom and optionally 1, 2 or 3 other heteroatoms independently selected from oxygen, nitrogen and sulphur, at most one of the other heteroatoms being oxygen or sulphur and $R^w$ is $R^6$ or CN;

$R^6$ is $C_{1-6}$alkyl, $C_{2-6}$alkenyl, $C_{2-6}$alkynyl, $C_{3-6}$cycloalkyl, hydroxy$C_{1-6}$alkyl, $C_{1-6}$alkoxy, $C_{2-6}$alkenyloxy, $C_{2-6}$alkynyloxy, $C_{1-6}$alkoxy$C_{1-6}$alkyl, $CH_2F$ or $CF_3$; and $R^7$ and $R^8$ are each independently hydrogen, $C_{1-6}$alkyl, $C_{2-6}$alkenyl, $C_{2-6}$alkynyl, $C_{3-6}$cycloalkyl or $CF_3$ or $R^7$ and $R^8$, together with the nitrogen atom to which they are attached, form a 4–7 membered heteroaliphatic ring containing the nitrogen atom as the sole heteroatom;

or a pharmaceutically acceptable salt thereof.

As used herein, the expression "$C_{1-6}$alkyl" includes methyl and ethyl groups, and straight-chained and branched propyl, butyl, pentyl and hexyl groups. Particular alkyl groups are methyl, ethyl, n-propyl, isopropyl and t-butyl. Derived expressions such as "$C_{1-4}$alkyl", "$C_{2-4}$alkenyl", "$C_{2-6}$alkenyl", "hydroxy$C_{1-6}$alkyl", "$C_{2-4}$alkyl" and "$C_{2-6}$alkynyl" are to be construed in an analogous manner.

The expression "$C_{3-6}$cycloalkyl" as used herein includes cyclic propyl, butyl, pentyl and hexyl groups such as cyclopropyl and cyclohexyl. $C_{5-6}$cycloalkenyl shall be construed in an analogous manner.

Suitable 5- and 6-membered heteroaromatic rings include pyridinyl, pyridazinyl, pyrimidinyl, pyrazinyl, pyrrolyl, pyrazolyl, oxazolyl, isoxazolyl, thiazolyl, isothiazolyl, imidazolyl, oxadiazolyl and thiadiazolyl groups. A suitable 5-membered heteroaromatic ring containing four nitrogen atoms is tetrazolyl. Suitable 6-membered heteroaromatic rings containing three nitrogen atoms include 1,2,4-triazine and 1,3,5-triazine.

Suitable 4–7 membered heterocyclic rings include piperidine, piperazine, morpholine, pyrrole, azetidine, homopiperazine and homopiperidine, unless otherwise indicated. Such rings may be partially saturated or unsaturated.

The term "halogen" as used herein includes fluorine, chlorine, bromine and iodine, of which fluorine and chlorine are preferred.

As used herein the term "$C_{1-6}$alkoxy" includes methoxy and ethoxy groups, and straight-chained, branched and cyclic propoxy, butoxy, pentoxy and hexoxy groups, including cyclopropylmethoxy. Derived expressions such as "$C_{2-6}$alkenyloxy", "$C_{2-6}$alkynyloxy", "$C_{1-4}$alkoxy", "$C_{2-4}$alkenyloxy" and "$C_{2-4}$alkyloxy" should be construed in an analogous manner.

A may be a $C_{1-4}$alkylidene group optionally substituted with one or more $C_{1-4}$alkyl.

A may be $C_{1-2}$alkylidene optionally substituted by one or two hydroxy or $C_{1-2}$alkyl groups. A may be $C_{1-2}$alkylidene substituted by hydroxy or by two methyl groups.

A is preferably $C_{1-2}$alkylidene optionally substituted with one, two or three methyl groups. Particularly A is $CH_2$, $CH_2CH_2$, $C(CH_3)H$ or $C(CH_3)_2$.

$R^1$ may be hydrogen, halogen or CN or a group $C_{1-4}$alkyl, $C_{2-4}$alkenyl, $C_{2-4}$alkynyl, $C_{1-4}$alkoxy, $C_{2-4}$alkenyloxy or $C_{2-4}$alkynyloxy, each of which groups is unsubstituted or substituted with one or two halogen atoms or with a pyridyl or phenyl ring each of which rings may be unsubstituted or independently substituted by one or two halogen atoms or nitro, cyano, amino, methyl or $CF_3$ groups. $R^1$ is typically hydrogen, fluorine, chlorine, bromine or a group $C_{1-4}$alkyl, $C_{2-4}$alkenyl, $C_{2-4}$alkynyl, $C_{1-4}$alkoxy, $C_{2-4}$alkenyloxy or $C_{2-4}$alkynyloxy, each of which groups is unsubstituted or substituted with one or two halogen atoms or by a pyridyl or phenyl ring each of which rings may be unsubstituted or substituted by one or two halogen atoms or nitro, cyano, amino, methyl or $CF_3$ groups and is generally hydrogen, fluorine or pyridylmethoxy, typically hydrogen.

$R^2$ may be hydrogen, halogen or CN or a group $C_{1-4}$alkyl, $C_{2-4}$alkenyl, $C_{2-4}$alkynyl, $C_{1-4}$alkoxy, $C_{2-4}$alkenyloxy or $C_{2-4}$alkynyloxy each of which groups is unsubstituted or substituted with one or two halogen atoms. $R^2$ is typically hydrogen, fluorine, chlorine or bromine, and is generally hydrogen or fluorine, typically hydrogen.

$R^{20}$ and $R^{21}$ may be $R^{20}$ and $R^{21}$ are independently chosen from hydrogen, $C_{1-10}$alkyl, $C_{2-10}$alkenyl, $C_{2-10}$alkynyl, amino$C_{1-10}$alkyl, $C_{1-6}$alkylamio$C_{1-10}$alkyl, di($C_{1-6}$alkyl) amino $C_{1-10}$alkyl and phenyl$C_{1-10}$alkyl, or $R^{20}$ and $R^{21}$, together with the nitrogen atom to which they are attached, form an unsaturated 4–7 membered heterocyclic ring optionally containing a further nitrogen atom or an oxygen atom, or a 5 or 6 membered heteroaromatic ring containing one, two or three further heteroatoms chosen from O, N and S, at most one of the heteroatoms being O or S, V may be substituted with one or two groups chosen from halogen, hydroxy, $C_{1-6}$alkyl, $CF_3$, CN, amino and nitro.

$R^{20}$ and $R^{21}$ are preferably independently selected from hydrogen, $C_{1-6}$alkyl, amino $C_{1-6}$alkyl, $C_{1-6}$alkylamino$C_{1-6}$alkyl, di($C_{1-6}$alkyl)amino $C_{1-6}$alkyl and phenyl $C_{1-6}$alkyl or $R^{20}$ and $R^{21}$, together with the nitrogen atom to which they are attached, form an azetidinyl, piperidinyl, piperazinyl or morpholinyl ring or a 5 or 6 membered heteroaromatic ring containing 1,2 or 3 further heteroatoms chosen from O, N and S, at most one of the heteroatoms being O or S, the heteroaromatic ring being optionally substituted by $C_{1-4}$alkyl.

Specific examples of $NR^{20}R^{21}$ are azetidinyl, dimethylamino, morpholinyl, N-methylpiperazinyl, piperidinyl, piperazinyl, imidazolyl, diethylamino, amino, (dimethylaminopropyl)(methyl)amino, methylamino, benzylamino and phenylethylamino.

Further specific examples of $NR^{20}R^{21}$ are morpholin-4-yl, ′butylamino, ethylamino, 4-methylpiperazin-1-yl, propylamino, 2,6-dimethylpiperidin-1-yl, diisopropylamino, 2,6-dimethylmorpholin-4-yl, diisobutylamino, dicyclohexylamino, (tertiarybutyl)(ethyl) amino, cyclohexylamino, (isopropyl)(cyclohexyl)amino, pyrrolyl, (ethyl)(cyclohexyl)amino, 2,5-dimethylpyrrol-1-yl, 4-methoxycarbonylpiperidin-1-yl, methoxycarbonylmethylamino, 4-(piperidin-1-yl)carboxylic acid, methylcarboxylic acid and 2,2,2-trifluoroethyl.

Particular preferred groups $ANR^{20}R^{21}$ are dimethylaminoethyl, azetidin-1-ylethyl, dimethylaminomethyl, dimethylaminoethyl, 1-amino-1-methylethyl and 1-dimethyl-1-methylethylamino.

Further specific examples of $ANR^{20}R^{21}$ include 1-methylpyrrol-2-yl, 4-hydroxypiperidin-1-yl and piperid-3-en-4-yl.

Preferably L is an oxygen atom. L may also be $NR^n$ in which $R^n$ is preferably hydrogen or methyl. $R^n$ may be hydrogen.

X is generally: pyridyl, pyrazinyl, pyridazinyl or pyrimidinyl optionally substituted by a halogen atom or a group $R^3$, $OR^3$, $NR^4R^5$ or a five membered heteroaromatic ring containing 1, 2 or 3 nitrogen atoms, and X is optionally fused to a benzene ring; a 5-membered heteroaromatic ring containing 2 or 3 heteroatoms chosen from oxygen, sulphur and nitrogen, at most one of the heteroatoms being oxygen or sulphur, which is unsubstituted or substituted by one, two or three groups independently chosen from halogen and $R^3$, or which is substituted by a pyridyl, phenyl or benzyl ring which ring is optionally independently substituted by one, two or three halogen atoms or $C_{1-6}$alkyl or $CF_3$ groups; or phenyl optionally substituted by one, two or three independently chosen halogen atoms. In particular X is pyridyl, pyrazinyl, pyridazinyl or pyrimidinyl which is unsubstituted or substituted by methyl, $CF_3$, methoxy, bromine, chlorine, isopropoxy, dimethylamino or a 5-membered heterocyclic ring containing 1, 2 or 3 nitrogen atoms, and X is optionally fused to a benzene ring, or X is pyrazolyl, isothiazolyl, isoxazolyl, 1,2,4-triazolyl, thiazolyl, 1,2,3-triazolyl or imidazolyl which is unsubstituted or substituted by one, two or three groups independently chosen from methyl, $CF_3$ and chlorine or is substituted by a phenyl, benzyl or pyridyl ring which ring is unsubstituted or substituted by chlorine or $CF_3$, or X is phenyl which is unsubstituted or substituted by chlorine. X may be monosubstituted by tri($C_{1-6}$alkyl) silyl$C_{1-6}$alkoxy$C_{1-4}$alkyl such as trimethylsilylethoxymethyl. A favoured value of X is pyridazine. Specific values of X are 2-pyridyl, 6-methylpyridin-2-yl, 3-pyridyl, 4-pyridyl, 3,5-dimethylpyrazol-1-yl, 3-methoxypyridin-2-yl, 3-methylisoxazol-5-yl, pyrazol-1-yl, 6-chloropyridin-2-yl, 6-bromopyridin-2-yl, 6-methoxypyridin-2-yl, 6-isopropoxypyridin-2-yl, 6-N,N-dimethylpyridin-2-yl, 6-(imidazol-1-yl)pyridin-2-yl, 3-pyridazino, 4-pyrimidinyl, pyrazin-2-yl, 2-quinolinyl, 2-quinoxalyl, 2-(4-trifluoromethyl)pyridyloxy, 4-methylisothiazolyl, 2,6-dichlorophenyl, 4-methylthiazol-5-yl, 2-methylthiazol-4-yl, 2-[1-(3-trifluoromethyl)pyrid-6-yl]imidazolyl, 1-benzylimidazol-2-yl, 1-(4-chlorophenyl)-1,2,3-triazol-4-yl, 3-chloro-2-methyl-5-trifluoromethylpyrazol-4-yl and 1-methyl-1,2,4-triazol-3-yl. Further specific values of X are (5-trifluoromethyl)pyridyl-2-yl, (3-trifluoromethyl)pyrid-2-yl, (4-trifluoromethyl)pyrid-2-yl, 1-methylimidazol-2-yl, 3-methylimidazol-4-yl, 1,2,4-triazol-3-yl, 1-isopropyl-1,2,4-triazol-3-yl, 4-methyl-1,2,4-triazol-3-yl, 1,2,3-triazol-4-yl, isothiazol-3-yl, 1-ethyl-1,2,4-triazol-3-yl, 2-methyl-1,2,3-triazol-4-yl, 1-methyl-1,2,3-triazol-4-yl, 2-methyl-1,2,4-triazol-3-yl, 1-methylimidazol-4-yl, 5-tert-butylpyridazin-3-yl and 1-methyl-1,2,3-triazol-5-yl. Still further particular values of X are 2-benzyl-1,2,4-triazol-3-yl, 1-benzyl-1,2,4-triazol-3-yl, 1-nbutyl-1,2,4-triazol-3-yl, 2-ethyl-1,2,4triazol-3-yl, 2-methylpyrazol-3-yl, 1-methylpyrazol-3-yl, 1-npropyl-1,2,4-triazol-3-yl, 1-(2,2,2-trifluoroethyl)-1,2,4-triazol-3-yl, 1-ethyl-1,2,3 -triazol-5-yl, 1-methyltetrazol-2-yl, imidazol-2-yl, 2-npropyl-1,2,4-triazol-3-yl,1-ethyl-1,2,3-triazol-4yl, 2-ethyl-1,2,3-triazol-4-yl, 1-ethylimidazol-5-yl, 1-ethylimidazol-4-yl, 1-npropyl-1,2,4-triazol-3-yl and 1-ethyl-1,2,3-triazol-5-yl.

When X is a substituted 6-membered heteroaromatic ring: $R^x$ is preferably halogen, $R^3$, $OR^3$, $NR^4R^5$ or a five-membered heteroaromatic ring containing 1, 2 or 3 nitrogen atoms and more preferably methyl, $CF_3$, methoxy, bromine, chlorine, isopropoxy, dimethylamino or a five-membered heterocyclic ring containing 1, 2 or 3 nitrogen atoms; and $R^y$ and $R^z$ are preferably absent.

When X is a substituted 5-membered heteroaromatic ring: $R^x$ is preferably halogen, $R^3$ or a pyridyl, phenyl or benzyl ring which ring is optionally independently substituted by one, two or three halogen atoms or $C_{1-6}$alkyl or $CF_3$ groups and more preferably $R^x$ is methyl, $CF_3$, chlorine or a phenyl, pyridyl or benzyl ring which ring is unsubstituted or substituted by chlorine or $CF_3$; and $R^y$ and $R^z$ are preferably halogen or $R^3$, and more preferably methyl, $CF_3$ or chlorine.

Particularly aptly X is an unsubstituted six-membered heteroaromatic group containing one or two nitrogen atoms.

Apt values for Y include $CH_2$, $CH(CH_3)$, $CH_2CH_2$ and $CH_2CH_2CH_2$ optionally substituted by an oxo group, and $CH_2CH_2O$ and $CH_2CH_2CH_2O$. For example, Y can be $CH_2$, $CH_2CH_2$, $CH_2CH_2CH_2$, $CH_2CH_2O$ or $CH_2CH_2CH_2O$. Preferably Y is $CH_2$ or $CH_2CH_2$ and most preferably $CH_2$.

From the foregoing it will be understood that particularly suitable groups L—Y—X are $OCH_2X$ groups where X is pyridyl or pyridazinyl, particularly 2-pyridyl.

$R^v$ is suitably chlorine, $R^6$, thienyl, furyl, pyridyl or $NR^7R^8$, more particularly $R^6$, thienyl, furyl, pyridyl or $NR^7R^8$, for example $C_{1-6}$alkyl, $C_{3-6}$cycloalkyl, hydroxy$C_{1-6}$alkyl, pyridyl, thienyl or amino and more particularly methyl, ethyl, ethoxy, isopropyl, cyclopropyl, thienyl or pyridyl, and even more particularly methyl, ethyl, isopropyl, cyclopropyl, thienyl or pyridyl. A further example of $R^v$ is chlorine.

$R^w$ is suitably $R^6$, for example $C_{1-6}$alkyl, $CH_2F$ or hydroxy$C_{1-6}$alkyl, more particularly methyl, $CH_2F$ or hydroxymethyl. Generally $R^w$ is absent.

$R^x$ may be halogen, $R^3$, $OR^3$, $OCOR^3$, $NR^4R^5$, $NR^4COR^5$, CN or $R^9$.

Z is preferably a 5-membered heteroaromatic ring containing 1, 2 or 3 heteroatoms independently selected from oxygen, nitrogen and sulphur, at most one of the heteroatoms being oxygen or sulphur and providing that when two of the heteroatoms are nitrogen an oxygen or sulphur atom is also present and that when one of the atoms is oxygen or sulphur then at least one nitrogen atom is present, or a 6-membered heteroaromatic ring containing 2 or 3 nitrogen atoms, Z being optionally substituted by $R^v$ and/or $R^w$, where $R^v$ is halogen, $R^6$, $NR^7R^8$, $NR^7COR^8$, CN, furyl, thienyl, phenyl, benzyl, pyridyl or a 5-membered heteroaromatic ring containing at least one nitrogen atom and optionally 1, 2 or 3 other heteroatoms independently selected from oxygen, nitrogen and sulphur, at most one of the other heteroatoms being oxygen or sulphur and $R^w$ is $R^6$ or CN.

Suitable values for Z include pyrimidinyl, pyrazinyl, pyrrolyl, oxazolyl, isoxazolyl, thiazolyl, isothiazolyl, oxadiazolyl and thiadiazolyl groups which groups are optionally substituted by $R^6$, thienyl, furyl, pyridyl or $NR^7R^8$ groups.

Z is very aptly a 5-membered heteroaromatic ring containing one oxygen and one or two nitrogen ring atoms and is optionally substituted by a group $R^6$. In such compounds $R^6$ is favourably a methyl group.

Favoured values for Z include optionally substituted isoxazoles and oxadiazoles.

Z may be unsubstituted.

Z may very aptly be substituted by methyl.

Particular values of Z are 3-methyloxadiazol-5-yl, 3-cyclopropyloxadiazol-5-yl, 5-methylisoxazol-3-yl, 5-(3-pyridyl)-isoxazol-3-yl, 5-hydroxymethylisoxazol-3-yl, 4,5-dimethylisoxazol-3-yl, 5-ethylisoxazol-3-yl, 5-cyclopropylisoxazol-3-yl, 5-isopropylisoxazol-3-yl, isoxazol-3-yl and 5-thienylisoxazol-3-yl. Further particular values for Z include 5-fluoromethylisoxazol-3-yl, 4-methylisoxazol-3-yl, 5-ethoxyisoxazol-3-yl, 4-methyl-5-chloroisoxazol-3-yl, 5-trifluoromethylisoxazol-3-yl, 5-(pyrid-2-yl)isoxazol-3-yl, 5-benzylisoxazol-3-yl, 5-chloroisoxazol-3-yl and 3-cyclopropyloxadiazol-5-yl. Still further particular values for Z include 5-methoxyisoxazol-3-yl, 5-methoxymethylisoxazol-3-yl, 5-methyloxadiazol-3-yl, pyrazin-2-yl and 3-methylisoxazol-5-yl.

$R^3$ may be $C_{1-6}$alkyl, $C_{2-6}$alkenyl, $C_{2-6}$alkynyl, $C_{3-6}$cycloalkyl, hydroxy$C_{1-6}$alkyl or $CF_3$.

Generally $R^3$ is $C_{1-6}$alkyl, $C_{1-6}$alkoxy or $CF_3$. In particular $R^3$ is methyl, methoxy, ispropoxy or trifluoromethyl.

Generally $R^4$ and $R^5$ are independently hydrogen or $C_{1-6}$alkyl, in particular hydrogen or methyl, for example both can be methyl.

$R^6$ may be $C_{1-6}$alkyl, $C_{2-6}$alkenyl, $C_{2-6}$alkynyl, $C_{3-6}$cycloalkyl, hydroxy$C_{1-6}$alkyl, $C_{1-6}$alkoxy, $C_{2-6}$alkenyloxy, $C_{2-6}$alkynyloxy, $CH_2F$ or $CF_3$. Generally $R^6$ is $CH_2F$, $CF_3$, $C_{1-6}$alkoxy, $C_{3-6}$cycloalkoxy, $C_{1-6}$alkyl or hydroxy$C_{1-6}$alkyl, for example, $CH_2F$, $CF_3$, methyl, ethyl, isopropyl, cyclopropyl or hydroxymethyl, particularly methyl or cyclopropyl. Alternatively $R^6$ is $C_{1-6}$alkyl or hydroxy$C_{1-6}$alkyl, for example, methyl, ethyl, isipropyl, cyclopropyl or hydroxymethyl.

Generally $R^7$ and $R^8$ are independently hydrogen or $C_{1-6}$alkyl, particularly hydrogen or methyl.

Generally $R^9$ is pyrazolyl, imidazolyl, phenyl, benzyl or pyridyl optionally substituted by halogen, preferably chlorine, or $CF_3$. In particular $R^9$ can be imidazol-1-yl, 3-trifluoromethylpyrid-5-yl, benzyl and 4-chlorophenyl.

Generally $R^{10}$ is $C_{1-6}$alkyl or $CF_3$, in particular methyl or $CF_3$, for example $CF_3$.

A preferred subclass of compounds is that represented by formula I':

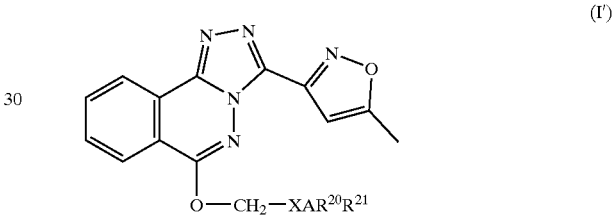

(I')

wherein A, X, $R^{20}$ and $R^{21}$ are as defined above. The preferred definitions of A, X, $R^{20}$ and $R^{21}$ apply to this subclass also.

For use in medicine, the salts of the compounds of formula I will be pharmaceutically acceptable salts. Hence in a favoured aspect this invention provides the compounds of the formula I and pharmaceutically acceptable salts thereof. Other salts may, however, be useful in the preparation of the compounds according to the invention or of their pharmaceutically acceptable salts. Suitable pharmaceutically acceptable salts of the compounds of this invention include acid addition salts which may, for example, be formed by mixing a solution of the compound according to the invention with a solution of a pharmaceutically acceptable acid such as hydrochloric acid, sulphuric acid, methanesulphonic acid, fumaric acid, maleic acid, succinic acid, acetic acid, benzoic acid, oxalic acid, citric acid, tartaric acid or phosphoric acid. Furthermore, where the compounds of the invention carry an acidic moiety, suitable pharmaceutically acceptable salts thereof may include alkali metal salts, e.g. sodium or potassium salts; alkaline earth metal salts, e.g. calcium or magnesium salts; and salts formed with suitable organic ligands, e.g. quaternary ammonium salts.

Where the compounds according to the invention have at least one asymmetric centre, they may accordingly exist as enantiomers. Where the compounds according to the invention possess two or more asymmetric centres, they may additionally exist as diastereoisomers. It is to be understood that all such isomers and mixtures thereof in any proportion are encompassed within the present invention.

It will be understood by the skilled person that when a five-membered heteroaromatic ring is referred to in the foregoing having four heteroatoms in the ring, then all these heteroatoms are nitrogen. It will further be understood that when a substituted five-membered heteroaromatic ring is referred to having two nitrogen atoms and an oxygen or sulphur atom in the ring, then only one substituent may be present so that aromaticity is maintained. Thus, for example, in such a case X may only be substituted by $R^x$ and Z may only be substituted by $R^y$.

Specific compounds within the scope of the present invention include:

dimethyl(2-{6-[3-(5-methylisoxazol-3-yl)-[1,2,4]triazolo[3,4-α]phthalazin-6-yloxymethyl]pyridin-3-yl}ethyl)amine;
6-[5-(1-azetidin-1-ylethyl)pyridin-2-ylmethyloxy]-3-(5-methylisoxazol-3-yl)-[1,2,4]triazolo[3,4-α]phthalazine;
dimethyl{6-[3-(5-methylisoxazol-3-yl)-[1,2,4]triazolo[3,4-α]phthalazin-6-yloxymethyl]pyridin-3-ylmethyl}amine;
dimethyl[2-{5-[3-(5-methylisoxazol-3-yl)-[1,2,4]triazolo[3,4-α]phthalazin-6-yloxymethyl]-[1,2,4]triazol-1-yl}ethyl] amine;
1-methyl-1-{2-[3-(5-methylisoxazol-3-yl)-[1,2,4]triazolo[3,4-α]phthalazin-6-yloxymethyl]pyridin-5-yl}ethylamine;
dimethyl-(1-methyl-1-{2-[3-(5-methyl-isoxazol-3-yl)-{1,2,4]triazolo[3,4-α]phthalazin-6-yloxymethyl]pyridin-5-yl}ethyl)amine;

and their pharmaceutically acceptable salts.
Further specific compounds include:

3-(5-methylisoxazol-3-yl)-6-[5-(1-methylpyrrolidin-2-yl)pyridin-2-ylmethoxy]-[1,2,4]triazolo[3,4-α]phthalazine;
N,N-dimethyl-2-[5-({[3-(5-methylisoxazol-3-yl)[1,2,4]triazolo[3,4-α]phthalazin-6-yl]oxy}methyl)-1H-[1,2,3]triazol-1-yl]ethylamine;
dimethyl-(2-{4-[3-(5-methylisoxazol-3-yl)-[1,2,4]triazolo[3,4-α]phthalazin-6-yloxymethyl]-[1,2,3]triazol-1-yl}ethyl)amine;
3-(5-methylisoxazol-3-yl)-6-(6-[morpholin-4-yl]pyridin-2-ylmethoxy)[1,2,4]triazolo-[3,4-α]phthalazine;
6-[5-(2-(azetidin-1-yl)ethyl)-1-methyl-1H-[1,2,3]triazol-4-ylmethoxy]-3-(5-methyl-isoxazol-3-yl)-[1,2,4]triazolo[3,4-α]phthalazine;
4-[5-({[3-(5-methylisoxazol-3-yl)[1,2,4]triazolo[3,4-α]phthalazin-6-yl]oxy}methyl)pyridin-2-yl]piperidin-4-ol;
3-(5-methylisoxazol-3-yl)-6-(1',2',3',6'-tetrahydro-[2,4']bipyridinyl-5-ylmethoxy)-[1,2,4]triazolo[3,4-α]phthalazine;
3-(5-methylisoxazol-3-yl)-6-(1-methyl-5-(piperidin-1-yl)methyl-1H-[1,2,3]triazol-4-ylmethoxy)-[1,2,4]triazolo[3,4-α]phthalazine;
2-(azetidin-1-yl)-1-{5-[3-(5-methylisoxazol-3-yl)-[1,2,4]triazolo[3,4-α]phthalazin-6-yloxymethyl]pyridin-2-yl}ethanol;
N-methyl-2-{4-[3-(5-methylisoxazol-3-yl)-[1,2,4]triazolo[3,4-α]phthalazin-6-yloxymethyl]-[1,2,3]triazol-1-yl}ethyl)amine;
tert-butyl[3-(5-methylisoxazol-3-yl)-[1,2,4]triazolo[3,4-α]phthalazin-6-yloxymethyl]pyridazin-3-ylmethyl}amine;
{2-[5-(3-isoxazol-3-yl-[1,2,4]triazolo[3,4-α]phthalazin-6-yloxymethyl)-[1,2,4]triazol-1-yl]ethyl}dimethylamine;
dimethyl[2-{5-[3-(3-methyl[1,2,4]oxadiazol-5-yl)-[1,2,4]triazolo[3,4-α]phthalazin-6-yloxymethyl]-[1,2,4]triazol-1-yl}ethyl)amine;
dimethyl{1-methyl-5-[3-(5-methylisoxazol-3-yl)-[1,2,4]triazolo[3,4-α]phthalazin-6-yloxymethyl]-1H-[1,2,4]triazol-3-ylmethyl}amine;
N-ethyl(1-{1-methyl-5-({[3-(5-methylisoxazol-3-yl)[1,2,4]triazolo[3,4-α]phthalazin-6-yl]oxy}methyl)-1H-[1,2,4]triazol-3-yl]ethylamine;

and their pharmaceutically acceptable salts.

Examples of pharmaceutically acceptable salts are hydrochlorides, sulfates, citrates, tartrates, acetates, methanesulfonates, phosphates, oxalates and benzoates.

The compounds of the present invention have a good binding affinity ($K_i$) for the α5 subunit. In a preferred embodiment the compounds of the invention are binding selective for the α5 subunit relative to the α1, α2 and α3 subunits. In another preferred embodiment the compounds are functionally selective for the α5 subunit as partial or full inverse agonists whilst substantially being antagonists at the α1, α2 and α3 subunits.

Cognition enhancement can be shown by testing the compounds in the Morris watermaze as reported by McNamara and Skelton, Psychobiology, 21:101–108. The functional efficacy at the various receptor subtypes can be calculated using the method disclosed in WO-A-9625948.

The invention also provides pharmaceutical compositions comprising one or more compounds of this invention and a pharmaceutically acceptable carrier. Preferably these compositions are in unit dosage forms such as tablets, pills, capsules, powders, granules, sterile parenteral solutions or suspensions, metered aerosol or liquid sprays, drops, ampoules, transdermal patches, auto-injector devices or suppositories; for oral, parenteral, intranasal, sublingual or rectal administration, or for administration by inhalation or insufflation. For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums or surfactants such as sorbitan monooleate, polyethylene glycel, and other pharmaceutical diluents, e.g. water, to form a solid preformulation composition containing a homogeneous mixture of a compound of the present invention, or a pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation composition is then subdivided into unit dosage forms of the type described above containing from 0.1 to about 500 mg of the active ingredient of the present invention. Typical unit dosage forms contain from 1 to 100 mg, for example 1, 2, 5, 10, 25, 50 or 100 mg, of the active ingredient. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

The present invention also provides a compound of the invention for use in a method of treatment of the human body. Preferably the treatment is for a condition associated with $GABA_A$ receptors comprising the α5 subunit and/or for the enhancement of cognition. Preferably the condition is a neurological deficit with an associated cognitive disorder such as a dementing illness such as Alzheimer's disease.

Other conditions to be treated include cognition deficits due to traumatic injury, stroke, Parkinson's disease, Downs syndrome, age related memory deficits, attention deficit disorder and the like.

Thus, for example, the compounds of the present invention can be used in a variety of disorders of the central nervous system. Such disorders include delirium, dementia and amnestic and other cognitive disorders. Examples of delirium are delirium due to substance intoxication or substance withdrawal, delirium due to multiple etiologies and delirium NOS (not otherwise specified). Examples of dementia are: dementia of the Alzheimer's type with early onset which can be uncomplicated or with delirium, delusions or depressed mood; dementia of the Alzheimer's type, with late onset, which can be uncomplicated or with delirium, delusions or depressed mood; vascular dementia which can be uncomplicated or with delirium, delusions or depressed mood; dementia due to HIV disease; dementia due to head trauma; dementia due to Parkinson's disease; dementia due to Huntington's disease; dementia due to Pick's disease; dementia due to Creutzfeld-Jakob disease; dementia which is substance-induced persisting or due to multiple etiologies; and dementia NOS. Examples of amnestic disorders are amnestic disorder due to a particular medical condition or which is substance-induced persisting or which is amnestic disorder NOS.

Those compounds which are not inverse agonists at the α5 subtype may be used as alcohol antagonists or to treat obesity.

The present invention further provides the use of a compound of the present invention in the manufacture of a medicament for the enhancement of cognition, preferably in a human suffering from a dementing illness such as Alzheimer's disease.

Also disclosed is a method of treatment of a subject suffering from a cognition deficit, such as that resulting from a dementing illness such as Alzheimer's disease, which comprises administering to that subject an effective amount of a compound according to the present invention.

The liquid forms in which the novel compositions of the present invention may be incorporated for administration orally or by injection include aqueous solutions, suitably flavoured syrups, aqueous or oil suspensions, and flavoured emulsions with edible oils such as cottonseed oil, sesame oil, coconut oil or peanut oil, as well as elixirs and similar pharmaceutical vehicles. Suitable dispersing or suspending agents for aqueous suspensions include synthetic and natural gums such as tragacanth, acacia, alginate, dextran, sodium carboxymethylcellulose, methylcellulose, polyvinyl-pyrrolidone or gelatin.

For the enhancement of cognition, a suitable dosage level is about 0.01 to 250 mg/kg per day, preferably about 0.01 to 100 mg/kg per day, and especially about 0.01 to 5 mg/kg of body weight per day. The compounds may be administered on a regimen of 1 to 4 times per day. In some cases, however, dosage outside these limits may be used.

The compounds of the invention may be coadministered with known treatments for Alzheimer's Disease, such as acetylcholinesterase inhibitors, muscarinic agonists, nicotinic agonists, β- or γ-secretase inhibitors, spheron disruptors, Aβ formation inhibitors and Aβ aggregation inhibitors.

It is preferred that the compounds of the present invention are ground, for example using a pestle and mortar or industrial equivalent thereto, to a particle size of between 1 and 10 μM, and preferably less than 5 μM, before formulation. The compounds may be micronised or sonicised by methods known in the art or nanonised, for example by methods disclosed in U.S. Pat. No. 5,145,684.

The compounds in accordance with the present invention may be prepared by a process which comprises reacting a compound of formula III with a compound of formula IV:

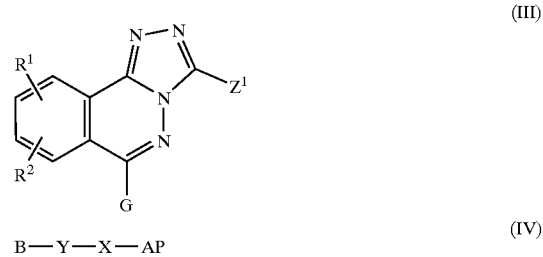

wherein A, $R^1$, $R^2$, X and Y are as defined above, G is a leaving group such as chlorine, $OCH_2CF_3$ or paratoluenesulfyloxy, B is LH where L is as defined above, $Z^1$ is a group Z as defined above or is a moiety which can be converted into a group Z by further reaction and P is a group $NR^{20}R^{21}$ as defined above or is a protected oxygen atom.

The reaction between compounds III and IV when L is O is conveniently effected by stirring the reactants in a suitable solvent, typically N,N-dimethylformamide and/or tetrahydrofuran, in the presence of a strong base such as sodium hydride or lithium hexamethyldisilylazide typically without heating and under an inert atmosphere such as nitrogen. When L is $NR''$ the reaction is conveniently effected in the presence of a strong base such as $Et_3N$ or NaH and a solvent such as DMF or DMSO generally for 15 to 60 hours with heating to 50–120° C. An example of oxygen protecting group is tert-butyl (dimethyl)silyl.

If necessary, the product of the reaction between the compounds of formulae III and IV is deprotected, for example by using tetrabutylammonium fluoride or a mixture of acetic acid, tetrahydrofuran and water. The resulting hydroxy compound is reacted with methane sulfonylchloride, generally at 0° C. in the presence of a base such as triethylamine for about an hour. The resulting methanesulfonic acid ester is then reacted with $HNR^{20}R^{21}$, where $R^{20}$ and $R^{21}$ are as defined above, to produce a compound of formula I. This reaction is generally carried out at reflux for several hours in solvents such as tetrahydrofuran and dichloromethane. Alternatively, after deprotection, the resulting alcohol is reacted with thionylbromide, generally in a solvent such as $CH_2Cl_2$ at about room temperature for 1 h at room temperature. The resulting bromide is then reacted with $HNR^{20}R^{21}$ to give the desired compound of formula I. The reaction is generally carried out under pressure in a solvent such as DMF at about 80° C. for 4 h. Alternatively the chloride can be produced using thionyl chloride generally in a solvent such as $CH_2Cl_2$ at room temperature for about 1 h under an inert atmosphere. The resulting compound is reacted with $HNR^{20}R^{21}$ at about room temperature for about 8 h.

Where the protecting group is a double bond the product of the reaction between the compounds of formulae III and IV can be reacted with N-bromo succinimide, generally in a mixture of DMF and $H_2O$ with an acid catalyst such as acetic acid at room temperature for 90 min. The resulting epoxide is reacted with $HNR^{20}R^{21}$ generally in a solvent such as DMF at about 80° C. for 4 h.

The intermediates of formula III above may be prepared by reacting a compound of formula V, which constitutes a further feature of the present invention, with a compound of formula VI:

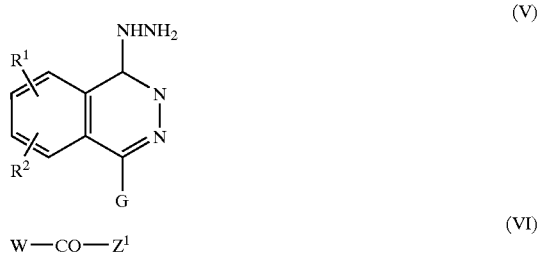

wherein $R^1$, $R^2$, G and $Z^1$ are as defined above, and W represents a suitable leaving group such as $C_{1-6}$alkoxy, chlorine or hydroxy.

The reaction is advantageously conducted in an inert organic solvent, generally in the presence of an organic nitrogen base and preferably under an inert atmosphere such as nitrogen. Suitable solvents include xylene, dioxane, tetrahydrofuran and lower aliphatic halogenated and aromatic hydrocarbons. Suitable organic nitrogen bases that may be employed include trialkylamines and pyridine. The reaction is generally conducted at a temperature range of from −20° C. to the reflux temperature of the reaction mixture, for a period of time that depends on the reactants employed and the temperature at which the reaction is carried out. The compound of formula VI may be activated by reacting with a compound such as bis (2-oxo-3-oxazolidinyl)phosphinic chloride or 1,1'-carbonyldiimidazole before reaction with the hydrazine.

When $Z^1$ is not a group Z, it is, for example, an alkyl-formyloxime group which can be converted to a carboxaldehydeoxime using tetrakis(triphenylphosphine)palladium (0) generally under an inert atmosphere such as nitrogen in the presence of triethylammonium formate, in a solvent such as ethanol for about 18 hours. The carboxaldehydeoxime can be converted to a carboxaldehydechloroxime by reacting with a chlorinating agent such as N-chlorosuccinimide in a solvent such as DMF. The carboxaldehydechloroxime can be converted to the desired group Z by reacting with an unsaturated compound such a vinylidene chloride, methyl propargyl ether, 3-phenyl-1-propyne, 2-pyridylacetylene, trifluoromethylacetylene or ethoxyacetylene generally in the presence of a base such a triethylamine, and a solvent such as dichloromethane. Alternatively, the carboxaldehydechloroxime can be converted to a group Z by reacting with ammonium hydroxide generally in a solvent such as ethanol for about 30 minutes and then acetic anhydride generally with heating to reflux for about 16 hours.

The reaction is advantageously conducted in an inert organic solvent, generally in the presence of an organic nitrogen base and preferably under an inert atmosphere such as nitrogen. Suitable solvents include xylene, dioxane, tetrahydrofuran and lower aliphatic halogenated and aromatic hydrocarbons. Suitable organic nitrogen bases that may be employed include trialkylamines and pyridine. The reaction is generally conducted at a temperature range of from −20° C. to the reflux temperature of the reaction mixture, for a period of time that depends on the reactants employed and the temperature at which the reaction is carried out. The compound of formula VI may be activated by reacting with a compound such as bis (2-oxo-3-oxazolidinyl)phosphinic chloride or 1,1'-carbonyldiimidazole before reaction with the hydrazine.

Compounds of formula III in which G is $OCH_2CF_3$ can be prepared by reacting a compound of formula III in which G is chlorine with 2,2,2-trifluoroethanol in the presence of a base such as lithium bis(trimethylsilyl)amide generally in a solvent such as DMF, preferably with cooling to about −20° C.−0° C. for a period of about 30 minutes.

The compound of formula V is prepared by reaction of a compound of formula VII:

where $R^1$, $R^2$ and G are as defined above, and G' is another suitable leaving group which may be the same as or different to G, with hydrazine, usually in the form of its monohydrate, generally in a solvent such as ethanol and generally by refluxing for a suitable period such as 15 minutes to 2 hours.

When the compound of formula VII is asymmetrical, that is $R^1$ and $R^2$ are different or if they are the same, the substitution pattern about the fused benzene ring is not symmetrical, the reaction between this compound and hydrazine will usually give rise to a mixture of isomeric products depending on whether group G or G' is displaced first. Thus in addition to the required product of formula V, the isomeric compound wherein the $R^1$ and $R^2$ moieties are reversed will usually be obtained to some extent. For this reason it will generally be necessary to separate the resulting mixture of isomers by conventional methods such as chromatography.

The compound of formula VII can be used to prepare a compound of formula III in a single step by reacting with the appropriate hydrazoic acid. This is generally carried out in the presence of a base, such as triethylamine, in a solvent such as xylene, at reflux under an inert atmosphere such as nitrogen.

The compound of formula VII can be prepared by reacting a compound of formula X:

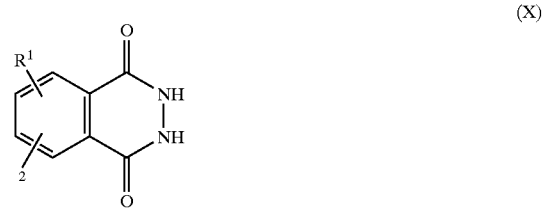

where $R^1$ and $R^2$ are as defined above, with a suitable reagent for introducing leaving groups G and $G^1$, for example where G and $G^1$ are both chlorine $POCl_3$ can be used generally with heating to reflux for about 16 hours.

The compound of formula X can be prepared by reacting a compound of formula XI with hydrazine hydrate ($H_2NNH_2.H_2O$):

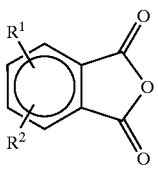

(XI)

where $R^1$ and $R^2$ are as defined above. The reaction is generally carried out in a protic solvent, such as 40% aqueous acetic acid, and in the presence of a buffering agent such as sodium acetate, generally with heating to reflux for about 16 hours.

The compound of formula XI can be prepared by reaction of a compound of formula XII:

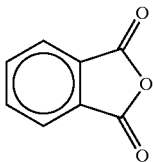

(XII)

with suitable reagents to introduce the substituents $R^1$ and $R^2$ where necessary. For example, when $R^1$ is phenyloxy or pyridyloxy or a derivative thereof, the corresponding hydroxy compound can be used as a reagent. The compound of formula XII is commercially available.

Alternatively, compounds of formula IV in which L is O and the carbon atom of Y adjacent to L is not tri-substituted can be made by reacting a compound of formula IX with a compound of formula XVIII:

Br—X—AP  (IX)

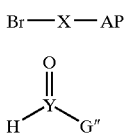

(XVII)

in which A, P, X and Y are as defined above and G″ is a leaving group such as NMe$_2$ generally between −78° C. and room temperature in a solvent such as THF. The bromine of the compound of formula IX is activated by conversion to an organometallic group with, for example BuLi, generally at −78° C. under an inert atmosphere, in a solvent such as THF. The product of the compounds of formulae IX and XVIII is reduced with, for example, sodium borohydride for about 1 h at room temperature to produce the compound of formula IV.

The compounds of formula IX in which P is a protected oxygen atom can be produced by protecting a compound of formula XIII:

Br—X—A—OH  (XIII)

with a protecting agent such as tert-butyldimethylsilylchloride under conventional conditions as shown in the Examples.

Compounds of formula IX in which P is a group NR$^{20}$R$^{21}$ can be made by reacting a compound of formula XIV with a compound of formula HNR$^{20}$R$^{21}$:

Br—X—A$^2$  (XIV)

where X, R$^{20}$ and R$^{21}$ are as defined above and A$^2$ is a group A as defined above substituted by an oxo group. The reaction is generally carried out in the presence of a reducing agent such as NaBH(OAc)$_3$ in a solvent such as dichloroethane at room temperature for above two days.

The compound of formula XIV can be made by reacting a compound of formula XV with a compound of formula XVI:

Br—X—Br  (XV)

A$^2$—NMe$_2$  (XVI)

where A$^2$ and X are as defined above, generally by initial reaction of the compound of formula XV with, for example, BuLi to convert the bromine to an organometallic group in a solvent such as diethylether at about −78° C. for about one hour, followed by addition of the compound of formula XVI.

Compounds of formula IV in which L is O can be produced by reacting a compound of formula XIX with HNR$^{20}$R$^{21}$ as defined above:

G‴—A—X—Y—P  (XIX)

where A, X and Y are as defined above, P is a protected oxygen atom and G‴ is a leaving group such as bromine or mesyl. When G‴ is bromine and A is a bond the Buchwald reaction utilising a palladium catalyst is carried out. When G‴ is mesyl the reaction is generally caried out in a solvent such as THF at reflux for about 4 hours.

Where they are not commercially available, the compounds of formula (XIX) in which A has two carbon atoms can be prepared by reacting a compound of formula XX:

H—X—Y—P  (XX)

in which X, Y and P are as defined above, with a strong base such as BuLi, generally in a solvent such as THF at −78° C. under an inert atmosphere, to generate the anion which is reacted with the appropriate epoxide at room temperature for abut 1 h to produce an alcohol which, if needed, can be converted to an alternative leaving group using, for example, mesyl chloride generally in a solvent such as CH$_2$Cl$_2$ in the presence of a strong base such as Et$_3$N at 0° C. under an inert atmosphere.

Where they are not commercially available, the starting materials of formulae IV, VI, HNR$^{20}$R$^{21}$, XIII, XV, XVI, XVII, XVIII and XX may be prepared by methods analogous to those described in the accompanying Examples, or by standard methods known from the art.

It will be understood that any compound of formula I initially obtained from the above process may, where appropriate, subsequently be elaborated into a further compound of formula I by techniques known from the art.

It will also be appreciated that where more than one isomer can be obtained from a reaction then the resulting mixture of isomers can be separated by conventional means.

Where the above-described process for the preparation of the compounds according to the invention gives rise to mixtures of stereoisomers, these isomers may be separated by conventional techniques such as preparative chromatography. The novel compounds may be prepared in racemic form, or individual enantiomers may be prepared either by enantiospecific synthesis or by resolution. The novel compounds may, for example, be resolved into their component enantiomers by standard techniques such as preparative HPLC, or the formation of diastereomeric pairs by salt formation with an optically active acid, such as (−)-di-p-toluoyl-d-tartaric acid and/or (+)-di-p-toluoyl-1-tartaric acid, followed by fractional crystallization and regeneration of the free base. The novel compounds may also be resolved by formation of diastereomeric esters or amides, followed by chromatographic separation and removal of the chiral auxiliary.

During any of the above synthetic sequences it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene & P. G. M. Wuts, *Protective Groups in Organic Synthesis*, John Wiley & Sons, 1991. The protecting groups may be removed at a convenient subsequent stage using methods known from the art.

The compounds in accordance with this invention potently inhibit the binding of [$^3$H]-flumazenil to the benzodiazepine binding site of human $GABA_A$ receptors containing the α5 subunit stably expressed in Ltk$^-$ cells.

Reagents

Phosphate buffered saline (PBS).

Assay buffer: 10 mM $KH_2PO_4$, 100 mM KCl, pH 7.4 at room temperature.

[$^3$H-Flumazenil (18 nM for α1β3γ2 cells; 18 nM for α2β3γ2 cells; 10 nM for α3β3γ2 cells; 10 nM for α5β3γ2 cells) in assay buffer.

Flunitrazepam 100 μM in assay buffer.

Cells resuspended in assay buffer (1 tray to 10 ml).

Harvesting Cells

Supernatant is removed from cells. PBS (approximately 20 ml) is added. The cells are scraped and placed in a 50 ml centrifuge tube. The procedure is repeated with a further 10 ml of PBS to ensure that most of the cells are removed. The cells are pelleted by centrifuging for 20 min at 3000 rpm in a benchtop centrifuge, and then frozen if desired. The pellets are resuspended in 10 ml of buffer per tray (25 cm×25 cm) of cells.

Assay

Can be carried out in deep 96-well plates or in tubes. Each tube contains:

300 μl of assay buffer.

50 μl of [$^3$H]-flumazenil (final concentration for α1β3γ2: 1.8 nM; for α2β3γ2: 1.8 nM; for α3β3γ2: 1.0 nM; for α5β3γ2: 1.0 nM).

50 μl of buffer or solvent carrier (e.g. 10% DMSO) if compounds are dissolved in 10% DMSO (total); test compound or flunitrazepam (to determine non-specific binding), 10 μM final concentration.

100 μl of cells.

Assays are incubated for 1 hour at 40° C., then filtered using either a Tomtec or Brandel cell harvester onto GF/B filters followed by 3×3 ml washes with ice cold assay buffer. Filters are dried and counted by liquid scintillation counting. Expected values for total binding are 3000–4000 dpm for total counts and less than 200 dpm for non-specific binding if using liquid scintillation counting, or 1500–2000 dpm for total counts and less than 200 dpm for non-specific binding if counting with meltilex solid scintillant. Binding parameters are determined by non-linear least squares regression analysis, from which the inhibition constant $K_i$ can be calculated for each test compound.

The compounds of the accompanying Examples were tested in the above assay, and all were found to possess a $K_i$ value for displacement of [$^3$H]Ro 15-1788 from the α5 subunit of the human $GABA_A$ receptor of 100 nM or less, most were at 50 nM or less, many were at 10 nM or less and some were at 1 nM or less.

The compounds of the present can be tested in the rat water maze test (Morris, Learning and Motivation, 1981, 12, 239ff) to show that they enhance cognition. Further details of methodology for demonstrating that the present compounds enhance cognition can be found in WO-A-9625948.

The following Examples illustrate the present invention:

INTERMEDIATE 1

6-Chloro-3-(5-methylisoxazol-3-yl)-1,2,4-triazolo[3, 4-α]phthalazine a) 1-Chloro-4-hydrazinophthalazine 1,4-Dichlorophthalazine (20.0 g, 0.100 mol) was added to a boiling solution of hydrazine monohydrate (37.3 ml, 0.765 mol) in ethanol (500 ml) and the mixture heated at reflux for 0.5 h. The mixture was cooled to room temperature and the solid collected by filtration and washed with ether. The material was taken with n-butanol and ammonia solution (sp. gr. 0.91) and heated until the solid dissolved. The organic layer was separated, evaporated in vacuo and the residue azeotroped with xylene (×2) and dried in vacuo to give the title-hydrazine (11.5 g, 59%), $^1$H NMR (250 MHz, d$^6$DMSO) δ 7.84–8.04 (3H, m, Ar—H), 8.20 (1H, m, Ar—H); MS (ES$^+$) m/e 194 [MH]$^+$.

b) 5-Methylisoxazole-3-carboxylic acid

A mixture of acetonylacetone (10 g, 88 mmol) and nitric acid (sp. gr. 1.42)/water (2:3) (50 ml) was cautiously brought to reflux under a stream of nitrogen and boiled for 1 h. The solution was cooled to room temperature and aged overnight. The resultant solid was collected by filtration, washed with chilled water (2×7 ml) and hexane, and dried in vacuo to give the title-acid (4.4 g, 40%), $^1$H NMR (CDCl$_3$) δ 2.50 (3H, d, J=0.8 Hz, Me), 6.41 (1H, d, J=0.8 Hz, Ar—H).

c) 6-Chloro-3-(5-Methylisoxazol-3-yl)-1,2,4-triazolo[3,4-α]phthalazine

5-Methylisoxazole-3-carboxylic acid (5.24 g, 41.3 mmol), bis(2-oxo-3-oxazolidinyl)phosphinic chloride (10.5 g, 41.2 mmol) and triethylamine (11.5 ml, 82.5 mmol) were added successively to a stirred suspension of 1-chloro-4-hydrazinophthalazine (8.00 g, 41.2 mmol) in dichloromethane (1 l) at 0° C. under nitrogen. The mixture was stirred at 0° C. for 2 h and at room temperature overnight. The solvent was evaporated in vacuo, the residue triturated with water and the solid filtered off, washed with hexane and dried in vacuo to give the ketohydrazine (11 g), MS (ES$^+$) m/e 304 [MH]$^+$. A solution of the ketohydrazine (11 g) and triethylamine hydrochloride (2.2 g, 20% w/w) in xylene (500 ml) was heated at reflux for 3 h. The mixture was cooled to room temperature and the solvent evaporated in vacuo. The residue was dissolved in dichloromethane, washed with water (×2), dried (MgSO$_4$) and evaporated in vacuo, and the solid recrystallised (dichloromethane/hexane) to give the title-compound (6.8 g, 58%), $^1$H NMR (360 MHz, CDCl$_3$) δ 2.59 (3H, s, Me), 6.90 (1H, s, Ar—H), 7.95 (1H, m, Ar—H), 8.07 (1H, m, Ar—H), 8.34 (1H, m, Ar—H), 8.78 (1H, s, Ar—H); MS (ES$^+$) m/e 286 [MH]$^+$.

EXAMPLE 1

Dimethyl(2-{6-[3-(5-methylisoxazol-3-yl)-[1,2,4] triazolo[3,4-α]phthalazin-6-yloxymethyl]pyridin-3-yl}ethyl)amine Step 1: 2-(2-Bromopyridin-5-yl)ethanol BuLi (32.2 ml of a 1.6 M solution in hexanes, 52 mmol) added dropwise to a stirred solution of 2,5-dibromopyridine (11.09 g, 46.8 mmol) in Et$_2$O (400 ml) at −78° C. under nitrogen. Upon complete addition the reaction mixture was stirred for 45 min and then a solution of ethylene oxide (6.74 g, 0.14 mol) in THF (70 ml) was added. The reaction mixture was warmed to room temperature, stirred for 1 h and then quenched by addition of NH₄Cl solution (sat., 150 ml). The organics were extracted with EtOAc (3×100 ml), washed with brine (100 ml) and dried (MgSO₄). The material was concentrated under reduced pressure, whilst simultaneously dry-loading onto silica. The material was purified by column chromatography on silica eluting with Et₂O and then EtOAc to give the pure alcohol (3.8 g, 40%).

¹H NMR (360 MHz, CDCl₃). δ 2.30 (1H, s), 2.80 (2H, t, J=6.0 Hz), 3.87 (2H, t, J=6.0 Hz), 7.39 (1H, d, J=8.1 Hz) 7.46 (1H, dd, J=8.1, 2.4 Hz), 8.20 (1H, d, J=2.4 Hz).

Step 2: 2-Bromo-5-[2-(tert-butyldimethylsilyloxy)ethyl]pyridine tert-Butyldimethylsilylchloride (2.98 g, 19.7 mmol) was added portionwise to a stirred solution of 2-(2-bromopyridin-5-yl)ethanol (3.8 g, 18.8 mmol), Et₃N (2.75 ml, 19.7 mmol) and DMAP (114 mg, 5 mol%) in CH₂Cl₂ (200 ml) at room temperature. The reaction was stirred for 12 h and then isohexane (300 ml) was added. The resulting precipitate was filtered and the filtrate concentrated under reduced pressure. The crude oil was purified by column chromatography on silica using 30% Et₂O/iso-hexane as eluent to give the silyl ether (4.92 g, 83%).

¹H NMR (360 MHz, CDCl₃) δ 0.00 (6H, s), 0.88 (9H, s), 2.78 (2H, t, J=6.2 Hz), 3.82 (2H, t, J=6.2 Hz), 7.37–7.50 (2H, m), 8.26 (1H, d, J=2.0 Hz).

Step 3: {5-[2-(tert-Butyldimethylsilyloxy)ethyl]pyridin-2-yl}methanol

BuLi (14.6 ml of a 1.6 M solution in hexanes, 23 mmol) was added to a stirred solution of 2-bromo-5-[2-(tert-butyldimethylsilyloxy)ethyl]pyridine (4.92 g, 15.6 mmol) in THF (100 ml) at −78° C. The resulting pale yellow solution was stirred for 1 h and then DMF (3.6 ml, 46.6 mmol) was added in one portion. The reaction mixture was warmed to room temperature and stirred for 90 min. MeOH (70 ml) was added, followed by NaBH₄ (589 mg, 15.6 mmol) and stirring was continued for a further 1 h. The reaction was quenched by cautious addition of NH₄Cl (sat. 100 ml) and the organics extracted with EtOAc (3×100 ml). The combined extracts were then washed with H₂O (70 ml) and brine (70 ml), dried (MgSO₄) and concentrated under reduced pressure. The material was used crude without further purification.

¹H NMR (360 MHz, CDCl₃) δ 0.00 (6H, s), 0.88 (9H, s), 2.83 (2H, t, J=6.4 Hz), 3.83 (2H, t, J=6.4 Hz), 4.76 (2H, s), 7.19 (1H, d, J=8.0 Hz), 7.54–7.60 (1H, m), 8.43 (1H, s).

Step 4: 6-{5-[2-(tert-Butyldimethylsilyloxy)ethyl]pyridin-2-ylmethyloxy}-3-(5-methyl-isoxazol-3-yl)-[1,2,4]triazolo[3,4-α]phthalazine A suspension of 6-chloro-3-(5-methylisoxazol-3-yl)-[1,2,4]triazolo[3,4-α]phthalazine and {5-[2-tert-butyldimethylsilyloxy)ethyl]pyridin-2-yl} methanol in THF (20 ml) and DMF (20 ml) at −78° C. under nitrogen was treated with lithium hexamethyldisilylazide (3.74 ml of a 1.0 M solution in THF, 3.74 mmol). The dark red reaction mixture was warmed to room temperature and stirred overnight. The solvent was removed under reduced pressure. Xylene (20 ml) was added and then removed under reduced pressure. CH₂Cl₂ (20 ml) and MeOH (20 ml) were added and the crude material was dry loaded onto silica. The mixture was purified by column chromatography on silica using 2→3% MeOH/CH₂Cl₂ containing 1% NH₃ solution to yield the title phthalazine (1.28 g, 66%).

¹H NMR (400 MHz, CDCl₃) δ 0.00 (6H, s), 0.87 (9H, s), 2.65 (3H, s), 2.89 (2H, t, J=5.7 Hz), 3.88 (2H, t, J=5.7 Hz), 5.79 (1H, s), 6.91 (1H, s), 7.66–7.74 (2H, m), 7.83–7.90 (1H, m), 7.95–8.04 (1H, m) 8.32–8.40 (1H, m), 8.57 (1H, br. s), 8.72–8.77 (1H, m).

Step 5: 2-{6-[3-(5-Methylisoxazol-3-yl)-[1,2,4]triazolo[3,4-α]phthalazin-6-yloxymethyl]pyridin-3-yl}ethanol Tetrabutylammonium fluoride (2.97 ml of a 1.0 M solution in THF, 2.0 mmol) was added to a stirred solution of the foregoing silyl ether (1.28 g, 2.48 mmol) in THF (100 ml) at room temperature. The reaction mixture was stirred for 1 h and then quenched by addition of NH₄Cl solution (sat., 50 ml). The organics were extracted with EtOAc (2×100 ml), then washed with brine (50 ml), dried MgSO₄ and dry loaded onto silica under reduced pressure. The crude residue was purified by column chromatography on silica using 8% MeOH/CH₂Cl₂ containing 1% NH₃ solution to yield the alcohol (423 mg, 42%).

¹H NMR (360 MHz, d₄-MeOH) δ 2.59 (3H, s), 2.87 (2H, t, J=6.4 Hz), 3.79 (2H, t, J=6.4 Hz), 5.71 (2H, s), 6.90 (1H, s), 7.71–7.75 (1H, m), 7.78–7.83 (1H, m), 7.88–7.96 (1H, m), 8.00–8.07 (1H, m), 8.33 (1H, d, J=8.0 Hz), 8.49(1H, br. s), 8.54 (1H, d, J=8.0 Hz). MS (ES⁺) 403 (M+1).

Step 6: Methanesulfonic acid 2-{6-[3-(5-Methylisoxazol-3-yl)-[1,2,4]triazolo[3,4-α]phthalazin-6-yloxymethyl]pyridin-3-yl}ethyl ester Methanesulfonyl chloride (96 μl, 1.22 mmol) was added to an ice-cold solution of 2-{6-[3-(5-methylisoxazol-3-yl)-[1,2,4]triazolo[3,4-α]phthalazin-6-yloxymethyl]pyridin-3-yl}ethanol (250 mg, 0.62 mmol) and Et₃N (173 μl, 122 mmol) in CH₂Cl₂ (50 ml) at 0° C. under nitrogen. The resulting mixture was stirred at 0° C. for 1 h, then diluted with CH₂Cl₂ (50 ml). The resultant solution was washed with H₂O (50 ml), HCl (40 ml) and NaHCO₃ solution (sat., 40 ml). The colourless solution was dried (MgSO₄) and concentrated under reduced pressure. The resultant mesylate was used directly without any further purification.

¹H NMR (360 MHz, CDCl₃) δ 2.58 (3H, s), 2.95 (3H, s), 3.11 (2H, t, J=6.5 Hz), 4.45 (2H, t, J=6.5 Hz), 5.73 (2H, s), 6.83 (1H, s), 7.27–7.95 (4H, m), 8.28 (1H, d, J=8.0 Hz), 8.55 (1H, br. s), 8.62 (1H, d, J=8.0 Hz). MS (ES⁺) 481 (M+1).

Step 7: Dimethyl(2-{6-[3-(5-methylisoxazol-3-yl)-[1,2,4]triazolo[3,4-α]phthalazin-6-yloxymethyl]pyridin-3-yl}ethyl)amine Dimethylamine (1.55 ml of a 2.0 M solution in THF, 3.1 mmol) was added to a stirred solution of methanesulfonic acid 2-{6-[3-(5-methylisoxazol-3-yl)-[1,2,4]triazolo[3,4-α]phthalazin-6-yloxymethyl]pyridin-3-yl}ethyl ester in CH₂Cl₂ (10 ml) and the mixture was heated at reflux overnight. More dimethylamine (3.1 mmol) was added and heating continued for a further 24 h. The reaction mixture was concentrated under reduced pressure, taken up in CH₂Cl₂ (20 ml) and dry loaded onto silica. Column chromatography on silica using 2.5% MeOH/CH₂Cl₂ containing 1% NH₃ solution as eluent gave the amine (52 mg, 39%) as a white solid which was recrystallised from CH₂Cl₂/isohexane.

¹H MNR (400 MHz, CDCl₃) δ 2.29 (6H, s), 2.50–2.58 (2H, m), 2.59 (3H, s), 2.80 (2H, t, J=7.4 Hz), 5.73 (2H, s), 6.84 (1H, s), 7.61 (1H, dd, J=7.2, 2.0 Hz), 7.68 (1H, d, J=7.2 Hz), 7.83 (1H, t, J=6.4 Hz), 7.92–7.98 (1H, m), 8.30 (1H, d, J=7.1 Hz), 8.51 (1H, br. s), 8.68 (1H, d, J=7.1 Hz). MS (ES⁺), 430 (M+1). MP 118–120° C.

C₂₃H₂₃N₇O₂. H₂O requires: C, 61.73; H, 5.63; N, 21.91%. Found: C, 61.54; H, 5.39; N, 21.73%.

EXAMPLE 2

6-[5-(1-Azetidin-1-ylethyl)pyridin-2-ylmethyloxy]-3-(5-methylisoxazol-3-yl)-[1,2,4]triazolo[3,4-α]phthalazine Step 1: 1-(6-Bromopyridin-3-yl)ethanone BuLi (32.8 ml of a 1.6 M solution in hexanes, 53 mmol) was added dropwise over 10 min to a stirred solution of 2,5-dibromopyridine (12.44 g, 52.5 mmol) in Et$_2$O (600 ml) at −78° C. under nitrogen. The resulting suspension was stirred at −78° C. for 1 h and then heated with dimethylacetamide (5.86 ml, 63 mmol). The reaction mixture was warmed to room temperature and stirred for 1 h. 1N HCl (100 ml) was added and the organic layer separated. The aqueous layer was extracted with EtOAc (3×100 ml). The combined organic extracts were dried (MgSO$_4$), concentrated under reduced pressure, then taken up in CH$_2$Cl$_2$ (200 ml) and dry loaded onto silica. Column chromatography on silica using 30–40% EtOAc/iso-hexane as eluent gave the ketone (6.0 g, 57%).

$^1$H NMR (360 MHz, CDCl$_3$) δ 2.62 (3H, s), 7.61 (1H, dd, J=8.3, 0.6 Hz), 8.07 (1H, dd, J=8.3, 2.4 Hz), 8.85–8.95 (1H, m).

Step 2: 5-[1-(Azetidin-1-yl)ethyl]-2-bromopyridine

NaBH(OAc)$_3$ (795 mg, 3.75 mmol) was added in one portion to a stirred solution of azetidine (674 μl, 10 mmol) and 1-(6-bromopyridin-3-yl)ethanone (500 mg, 2.5 mmol) in 1,2-dichloroethane (60 ml) at room temperature under nitrogen. The reaction was stirred at room temperature for 48 h and then 2N NaOH (10 ml) was added. The organics were extracted with CH$_2$Cl$_2$ (3×20 ml) and the combined extracts were concentrated under reduced pressure whilst dry loading onto silica. Purification by column chromatography on silica using 1.5% MeOH/CH$_2$Cl$_2$ containing 1% NH$_3$ solution gave the amine (400 mg, 66%).

$^1$H NMR (360 MH$_z$, CDCl$_3$), δ 1.18 (3H, d, J=6.5 Hz) 2.02 (2H, quintet, J=7.0 Hz), 3.06 (2H, q, J=7.0 Hz) 3.15 (2H, q, J=7.0 Hz), 3.26 (2H, q, J=6.5 Hz) 7.42 (1H, d, J=8.2 Hz), 7.53 (1H, dd, J=8.2, 2.5 Hz) 8.27 (1H, d, J=2.5 Hz).

Step 3: [5-{1-(Azetidin-1-yl)ethyl}pyridin-2-yl]methanol

In the same way as described in Example 1, Step 3 using 5-[1-(azetidin-1-yl)ethyl]-2-bromopyridine (0.4 g, 1.66 mmol), purification by column chromatography on silica using 10% MeOH/CH$_2$Cl$_2$+1% NH$_3$ solution gave the alcohol (67 mg, 21%).

$^1$H NMR (360 MHz, CDCl$_3$) δ 1.20 (3H, d, J=6.5 Hz) 2.02 (2H, quintet, J=7.0 Hz), 3.06 (2H, q, J=7.0 Hz) 3.18 (2H, q, J=7.0 Hz), 3.30 (2H, q, J=6.5 Hz), 4.74 (2H, s), 7.23 (1H, d, J=8.0 Hz), 7.66 (1H, dd, J=8.0, 2.1 Hz), 8.45 (1H, d, J=2.1 Hz) MS (ES$^+$) 193 (M+1).

Step 4: 6-[5-{1-(Azetidin-1-yl)ethyl}pyridin-2-ylmethyloxyl]-3-(5-methyl isoxazol-3-yl)-[1,2,4]triazolo[3,4-α]phthalazine The reaction was carried out as described in Example 1, Step 4 using 6-chloro-3-(5-methylisoxazol-3-yl)-[1,2,4]triazolo[3,4-α]phthalazine (100 mg, 0.35 mmol) and [5-{1-(azetidin-1-yl)ethyl}pyridin-2-yl]methanol (67 mg, 0.35 mmol) to give, after column chromatography on silica, eluting with 2.5% MeOH/CH$_2$Cl$_2$ containing 1% NH$_3$ solution, the amine (121 mg, 79%) which was recrystallised from CH$_2$Cl$_2$/hexane.

$^1$H NMR (360 MHz, CDCl$_3$) δ 1.22 (3H, d, J=6.5 Hz), 2.02 (2H, quintet, J=7.0 Hz), 2.60 (3H, s), 3.08 (2H, q, J=7.0 Hz), 3.18 (2H, q, J=7.0 Hz), 3.34 (2H, q, J=6.5 Hz), 5.72 (2H, s), 6.81 (1H, s), 7.68–7.85 (3H, m), 7.87–7.96 (1H, m), 8.27 (1H, d, J=8.0 Hz), 8.57 (1H, br. s), 8.62 (1H, d, J=7.9 Hz). MS (ES$^+$) 442 (M+1). MP 195–198° C.

C$_{24}$H$_{23}$N$_7$O$_2$. 0.25 (H$_2$O) requires: C, 64.63; H, 5.31; N, 21.98%. Found: C, 64.61; H, 4.95; N, 21.71%.

EXAMPLE 3

Dimethyl{6-[3-(5-methylisoxazol-3-yl)-[1,2,4]triazolo[3,4-α]phthalazin-6-yloxymethyl]pyridin-3-ylmethyl}amine Step 1: (2-Bromopyridin-5-yl)methanol Two simultaneous reactions were conducted whereby: BuLi (29.9 ml of a 1.6 M solution in hexanes, 47.7 mmol) was added to a stirred solution of 2,5-dibromopyridine (10.3 g, 43.4 mmol) in Et$_2$O (250 ml) at −78° C. under nitrogen over 10 min. The resulting mixture was stirred for 15 min, then DMF (10.07 ml, 0.13 mol) was added. The reaction was allowed to warm to room temperature and then stirred for a further 30 min. The reaction was quenched by addition of H$_2$O (30 ml). The reaction mixtures were combined and extracted with EtOAc (3×250 ml). The combined organic extracts were washed with brine (100 ml), dried and concentrated under reduced pressure. The crude residue was taken up in EtOH (100 ml) and cooled to 0° C. NaBH$_4$ (3.26 g, 86.4 mmol) was added portionwise over 10 min, the reaction was warmed to room temperature and stirred for 90 min. NH$_4$Cl (sat., 50 ml) was added cautiously, most of the EtOH was removed under reduced pressure and the reaction mixture was diluted with H$_2$O (100 ml). After extraction with EtOAc (3×250 ml), the combined organic extracts were washed with brine (50 ml), dried and concentrated under reduced pressure. Column chromatography on silica using 75–80% Et$_2$O/hexanes as eluent gave the title alcohol (5.65 g, 35%).

$^1$H NMR (360 MHz, CDCl$_3$) δ 4.69 (2H, s), 7.46 (1H, d, J=8.2 Hz), 7.59 (1H, dd, J=8.2, 2.2 Hz), 8.30 (1H, d, J=2.2 Hz). MS (ES$^+$) 187 (M$^+$).

Step 2: 2-Bromo-5-(tert-butyldimethylsilyloxymethyl)pyridine

The reaction was carried out as described in Example 1, Step 2 using (2-bromopyridin-5-yl)methanol (5.69 g, 30.06 mmol) to give after column chromatography on silica using 15% Et$_2$O/hexanes as eluent the silyl ether (7.86 g, 87%).

$^1$H NMR (360 MHz, CDCl$_3$) δ 0.00 (6H, s), 0.82 (9H, s), 4.60 (2H, s), 7.34 (1H, d, J=8.2 Hz), 7.42 (1H, dd, J=8.2, 2.0 Hz), 8.20 (1H, d, J=2.0 Hz). MS (ES$^+$) 302 (M$^+$).

Step 3: 5-(tert-Butyldimethylsilyloxymethyl)-2-(hydroxymethyl)pyridine

The reaction was carried out as described in Example 1, Step 3 using 2-bromo-5-(tert-butyldimethylsilyloxymethyl)pyridine (12 g, 39.7 mmol), BuLi (37 ml of a 1.6 M solution in hexanes, 59.6 mmol) DMF (9.2 ml, 0.12 mol) and NaBH$_4$ (1.5 g, 39.7 mmol) to yield, after column chromatography on silica using Et$_2$O as eluent, the title alcohol (6.66 g, 66%).

$^1$H NMR (360 MHz, CDCl$_3$) δ 00.0 (6H, s), 0.83 (9H, s), 4.64 (4H, br. s), 7.11 (1H, d, J=8.0 Hz), 7.54 (1H, d, J=8.0 Hz), 8.39 (1H, s).

Step 4: 6-[5-(tert-Butyldimethylsilyloxymethyl)pyridin-2-ylmethyloxy]-3-(5-methylisoxazol-3-yl)-[1,2,4]triazolo[3,4-α]phthalazine The reaction was carried out as described in Example 1, Step 4 using 5-(tert-butyldimethylsilyloxymethyl)-2-(hydroxymethyl)pyridine (1.0 g, 3.95 mmol) and 6-chloro-3-(5-methylisoxazol-3-yl)-[1,2,4]triazolo[3,4-α]phthalazine (1.12 g, 3.95 mmol) to give, after column chromatography on silica using 2–3% MeOH/CH$_2$Cl$_2$ as eluent, the title phthalazine (1.4 g, 70%).

$^1$H NMR (360 MHz, CDCl$_3$) δ 0.00 (6H, s), 0.82 (9H, s), 2.47 (3H, s), 4.67 (2H, s), 5.64 (2H, s), 6.72 (1H, s), 7.54–7.63 (3H, m), 7.66–7.73 (1H, m), 7.80–7.87 (1H, m), 8.18 (1H, d, J=8.1 Hz), 8.50 (1H, s), 8.57 (1H, d, J=8.1 Hz).

Step 5: {6-[3-(5-Methylisoxazol-3-yl)-[1,2,4]triazolo[3,4-α]phthalazin-6-yloxymethyl]pyridin-3-yl}methanol A solution of 6-[5(tert-butyldimethylsilyloxymethyl) pyridin-2-ylmethyloxy]-3-(5-methylisoxazol-3-yl)-[1,2,4] triazolo[3,4-α]phthalazine (1.4 g, 2.78 mmol) in AcOH/THF/H$_2$O [3:1:1, 50 ml] was stirred at room temperature for 36 h. The mixture was concentrated under reduced pressure and then azeotroped with toluene (2×50 ml). The material was used without further purification.

$^1$H NMR (360 MHz d$_6$-DMSO) δ 2.58 (3H, s), 4.56 (2H, s), 5.69 (2H, s), 6.98 (1H, s), 7.72 (1H, d, J=7.9 Hz), 7.81 (1H, dd, J=8.0, 2.1 Hz), 7.96 (1H, t, J=7.6 Hz), 8.10 (1H, t, J=7.6 Hz), 8.30 (1H, d, J=7.9 Hz), 8.53–8.64 (2H, m).

Step 6: Methanesulfonic acid 6-[3-(5-Methylisoxazol-3-yl)-[1,2,4]triazolo[3,4-α]-phthalazin-6-yloxymethyl]pyridin-3-ylmethyl ester Methanesulfonyl chloride (1.07 ml, 13.9 mmol) was added to a stirred suspension of {6-[3-(5-methylisoxazol-3-yl)-[1,2,4]triazolo[3,4-α]phthalazin-6-yloxymethyl]pyridin-3-yl}methanol (2.78 mmol), Et$_3$N (1.94 ml, 13.9 mmol) in CH$_2$Cl$_2$ (100 ml) under nitrogen. The reaction mixture was stirred overnight and then diluted with CH$_2$Cl$_2$. The resulting solution was washed with H$_2$O (100 ml), 1 N HCl (100 ml), NaHCO$_3$ (sat., 100 ml) and brine (100 ml). The solution was then dried MgSO$_4$) and concentrated under reduced pressure. The resultant mesylate was used without further purification.

$^1$H NMR (360 MHz, CDCl$_3$) δ 2.59 (3H, s), 3.67 (3H, s), 5.28 (2H, s), 5.78 (2H, s), 6.83 (1H, s), 7.86–8.03 (4H, m), 8.31 (1H, d, J=8.1 Hz), 8.66–8.76 (2H, m). MS (ES$^+$) 467 (M+1).

Step 7: Dimethyl{6-[3-(5-methylisoxazol-3-yl)-[1,2,4]triazolo[3,4-α]phthalazin-6-yloxymethyl]pyridin-3-ylmethyl}amine Dimethylamine (5 ml of a 2 M solution in THF, 10 mmol) was added to a stirred solution of the crude methanesulfonic acid 6-[3-(5-methylisoxazol-3-yl)-[1,2,4]triazolo[3,4-α] phthalazin-6-yloxymethyl]pyridin-3-ylmethyl ester (0.278 mmol) in CH$_2$Cl$_2$ (20 ml) and stirred at room temperature for 60 h. The reaction mixture was diluted with CH$_2$Cl$_2$ (20 ml) and dry loaded onto silica whilst concentrating under reduced pressure. The residue was purified by column chromatography on silica, using 3% MeOH/CH$_2$Cl$_2$ containing 1% NH$_3$ solution as eluent, to give the amine (68 mg, 59%) after recrystallisation from CH$_2$Cl$_2$/hexanes.

$^1$H NMR (360 MHz, CDCl$_3$) δ 2.25 (6H, s), 2.59 (3H, s), 3.46 (2H, s), 5.76 (2H, s), 6.83 (1H, s), 7.69–7.88 (3H, m), 7.93–8.00 (1H, m), 8.32 (1H, d, J=8.0 Hz), 8.57 (1H, s), 8.69 (1H, d, J=7.6 Hz). MS (ES$^+$) 416 (M+1). MP 170–172° C.

C$_{22}$H$_{21}$N$_7$O$_2$. 0.5 (H$_2$O) requires: C, 62.25; H, 5.22; N, 23.10%. Found: C, 62.37; H, 4.82; N, 23.08%.

EXAMPLE 4

Dimethyl[2-{5-[3-(5-methylisoxazol-3-yl)-[1,2,4] triazolo[3,4-α]phthalazin-6-yloxymethyl]-[1,2,4] triazol-1-yl}ethyl]amine Step 1: Dimethyl(2-[1,2,4]triazol-1-ylethyl)amine Sodium hydride (2.08 g of a 60% dispersion in mineral oils, 52.0 mmol) was added portionwise over 5 min to a stirred solution of 1,2,4-triazole (3.0 g, 43.4 mmol) in DMF (50 ml) at room temperature. The mixture was stirred for 15 min and then added to a stirred suspension of 2-dimethylaminoethyl chloride hydrochloride (8.13 g, 56.4 mmol) in DMF (50 ml). The mixture was stirred for 15 min and then NaH (60%, 2.08 g, 52.0 mmol) was added portionwise over 15 min. The reaction mixture was stirred overnight at room temperature and then for a further 3 h at 70° C. The reaction was quenched by cautious addition to H$_2$O/ice (150 ml). Xylene (500 ml) was added and the mixture concentrated under reduced pressure. More xylene (500 ml) was added and the process repeated. The crude residue was extracted with CH$_2$Cl$_2$ (3×300 ml) and the combined organics washed with brine (50 ml), dried (MgSO$_4$) and concentrated under reduced pressure. Finally the residue was azeotroped with xylene (3×200 ml) to give the title amine (4.35 g, 71%).

$^1$H NMR (360 MHz, CDCl$_3$) δ 2.28 (6H, s), 2.74 (2H, t, J=6.3 Hz), 4.25 (2H, t, J=6.3 Hz), 7.93 (1H, s), 8.18 (1H, s). MS (ES$^+$) 140 (M$^+$).

Step 2: [2-(2-Dimethylaminoethyl)-2H-[1,2,4]triazol-3-yl] methanol

BuLi (6.87 ml of a 1.6 M solution in hexanes, 11.0 mmol) was added dropwise over 2 min to a stirred solution of dimethyl(2-[1,2,4]triazol-1-ylethyl)amine (1.4 g, 10 mmol) in THF (50 ml) at −78° C. under nitrogen. The resulting mixture was stirred at −78° C. for 15 min, then warmed to −40° C. and re-cooled to −78° C. DMF (2.31 ml, 30 mmol) was added and the reaction mixture warmed to room temperature and stirred for 15 min. MeOH was added followed by NaBH$_4$ (567 mg, 15 mmol) and the reaction mixture stirred for 30 min. H$_2$O (10 ml) was added followed by 1N HCl (50 ml). The reaction was left to stand overnight. The solvent was removed under reduced pressure and the aqueous extracted with CH$_2$Cl$_2$ (5×75 ml). The combined organic extracts were washed with brine (25 ml), dried (MgSO$_4$) and concentrated under reduced pressure. The crude residue was azeotroped with xylene (2×100 ml) to yield the alcohol (1.24 g, 73%).

$^1$H NMR (360 MHz, CDCl$_3$) δ 2.27 (6H, s), 2.70–2.77 (2H, m), 4.28–4.36 (2H, m), 4.69 (2H, s), 7.83 (1H, s).

Step 3: Dimethyl[2-{5-[3-(5-methylisoxazol-3-yl)-[1,2,4] triazolo[3,4-α]phthalazin-6-yloxymethyl]-[1,2,4]triazol-1-yl}ethyl]amine The reaction was carried out as described in Example 1, Step 4 using [2-(2-dimethylaminoethyl)-2H-[1,2,4)]triazol-3-yl]methanol (200 mg, 1.17 mmol) and 6-chloro-3-(5-methylisoxazol-3-yl)-[1,2,4]triazolo[3,4-α]phthalazine (336 mg, 1.17 mmol) to give after column chromatography on silica, using 5→10% MeOH/CH$_2$Cl$_2$ containing 1% NH$_3$ solution as eluent, the amine (347 mg, 71%) which was recrystallised from CH$_2$Cl$_2$/iso-hexane.

$^1$H NMR (400 MHz, CDCl$_3$) δ 2.25 (6H, s), 2.57 (3H, s), 2.77 (2H, t, J=5.5 Hz), 4.49 (2H, t, J=5.5 Hz), 5.84 (2H, s), 6.85 (1H, s), 7.81 (1H, t, J=7.5 Hz), 7.90–8.00 (2H, m), 8.25 (1H, d, J=6.9 Hz), 8.66 (1H, d, J=7.5 Hz). MS (ES$^+$) 420 (M+1). MP 148–153° C.

C$_{20}$H$_{21}$N$_9$O$_2$ requires: C, 57.27; H, 5.05; N, 30.05%. Found: C, 56.96; H, 5.01; N, 29.92%.

EXAMPLE 5

1-Methyl-1-{2-[3-(5-methylisoxazol-3-yl)-[1,2,4] triazolo[3,4-α]phthalazin-6-yloxymethyl]pyridin-5-yl}ethylamine Step 1: (6-Methyl-1-oxy)nicotinonitrile Trifluoroacetic acid (11.0 g) was added to a stirred solution of 5-cyano-2-methylpyridine (10 g, 84.6 mmol) in AcOH (125 ml) at room temperature under nitrogen. H$_2$O$_2$ (30% (w/v) in H$_2$O, 15 ml) was then added and the reaction was warmed to 90° C. and heated for 12 h. The reaction mixture was diluted with H$_2$O (100 ml) and concentrated under reduced pressure. Further H$_2$O (70 ml) was added and the resultant mixture was neutralised with solid Na$_2$CO$_3$ and then extracted with CHCl$_3$ (2×125 ml). The combined organic extracts were dried (MgSO$_4$) and concentrated under reduced pressure to yield the crude N-oxide (10.7 g, 94%).

¹H NMR (360 MHz, CDCl₃) δ 2.57 (3H, s), 7.40–7.45 (2H, br. s), 8.49 (1H, s). MS (ES⁺) 134 (M⁺).

Step 2: 6-(tert-Butyldimethylsilyloxymethyl)nicotinonitrile

Trifluoroacetic anhydride (27.9 ml, 0.2 mol) was added dropwise over 10 min. to a stirred solution of (6-methyl-1-oxy)nicotinonitrile (10.7 g, 79.9 mmol) in dry CH₂Cl₂ (250 ml) at room temperature under nitrogen which produced an exothermic reaction. The reaction mixture was then stirred for a further 1 h and concentrated under reduced pressure. The crude mixture was dissolved in CH₂Cl₂ (100 ml) then Na₂CO₃ (2N, 300 ml) was added and stirred for 2.5 h. The organics were extracted with CH₂Cl₂ (3×200 ml) and the combined extracts were washed with brine (150 ml), dried (MgSO₄) and concentrated under reduced pressure, to yield the crude alcohol (7.85 g). Tert-butyldimethylsilyl chloride (8.88 g, 58 mmol) was then added to a stirred solution of the crude alcohol (7.85 g, 58 mmol), Et₃N (12.24 ml, 87 mmol) and DMAP (357 mg, 5 mol %) in CH₂Cl₂ (250 ml) at room temperature. The resulting solution was stirred overnight. Iso-hexane (400 ml) was added and the resultant precipitate was removed by filtration. The filtrate was concentrated under reduced pressure and purified by column chromatography on silica, using 30% Et₂O/iso-hexane as eluent, to give the silyl ether (9.11 g, 46%)

¹H NMR (360 MHz, CDCl₃) δ 0.00 (6H, s), 0.82 (9H,s), 4.73 (2H, s), 7.53 (1H, d, J=8.2 Hz), 7.83 (1H, d, J=8.2 Hz) 8.64 (1H, s). MS (ES⁺) 249 (M+1).

Step 3: 1-[2-(tert-Butyldimethylsilyloxymethyl)pyridin-5-yl](1-methyl)ethylamine CeCl₃.7H₂O (10 g, 26.8 mmol) was dried overnight at 120° C., 0.1 mm Hg and then for 4 h at 150° C., 0.1 mm Hg. The resulting powder was cooled to room temperature and THF (140 ml) was added and the mixture stirred for 15 min. The suspension was then cooled to –78° C. and MeLi (16.8 ml of a 1.6 M solution in Et₂O, 26.8 mmol) was then added dropwise over 7 min. The mixture was stirred for 30 min and then a solution of 6-(tert-butyldimethylsilyloxymethyl)nicotinonitrile (2.21 g, 8.9 mmol) in THF (10 ml) was added. The cooling bath was removed and the reaction was allowed to warm to room temperature. After stirring for 2 h NH₃ (conc., 25 ml) was added and the mixture filtered through celite. The filter pad was washed with CH₂Cl₂ (400 ml). The combined filtrates were concentrated under reduced pressure then taken up in CH₂Cl₂ (200 ml) and dried (MgSO₄). The solvent was evaporated to yield the crude amine (2.42 g, 96%) which was used without further purification.

¹H NMR (360 MHz, CDCl₃) δ 0.00 (6H, s), 0.83 (9H, s), 1.31 (6H, s), 4.70 (2H, s), 7.33 (1H, d, J=8.4 Hz), 7.73 (1H, d, J=8.4 Hz), 8.53 (1H, br. s). MS (ES⁺) 264 (M–NH₂).

Step 4: 1-[2-(Hydroxymethyl)pyridin-5-yl](1-methyl)ethylamine

A solution of 1-[2-(tert-butyldimethylsilyloxymethyl) pyridin-5-yl](1-methyl)ethylamine (1.5 g, 5.35 mmol) in AcOH (15 ml), THF (5 ml) and H₂O (5 ml) was heated at 50° C. for 2.5 h. The resultant mixture was concentrated under reduced pressue and then azeotroped with toluene (2×50 ml). The residue was dissolved in CH₂Cl₂ (15 ml) and MeOH (15 ml) and dry loaded onto silica. Purification by column chromatography on silica, using 10% MeOH/CH₂Cl₂ containing 1% NH₃ solution as eluent, gave the desired alcohol (330 mg, 37%).

¹H NMR (360 MHz, CDCl₃) δ 1.51 (6H, s), 4.73 (2H, s), 7.24 (1H, dd, J=8.2, 0.4 Hz), 7.84 (1H, dd, J=8.2, 2.3 Hz), 8.70 (1H, br. s).

Step 5: 1-Methyl-1-{2-[3-(5-methylisoxazol-3-yl)[1,2,4]triazolo[3,4-α]phthalazin-6-yloxymethyl]pyridin-5-yl}ethylamine The reaction was carried out as described in Example 1, Step 4 using 1-[2-(hydroxymethyl)pyridin-5-yl](1-methyl) ethylamine (330 mg, 1.98 mmol) and 6-chloro-3-(5-methylisoxazol-3-yl)-[1,2,4]triazolo[3,4-α]phthalazine to give after column chromatography on silica, eluting with 4% MeOH/CH₂Cl₂ containing 1% NH₃ solution, the title compound (504 mg, 61%) which was recrystallised from CH₂Cl₂/hexanes.

¹H NMR (400 MHz, CDCl₃) δ 1.54 (6H, s), 2.60 (3H, s), 5.74 (2H, s), 6.85 (1H, s), 7.72 (1H, d, J=7.3 Hz), 7.81 (1H, t, J=6.4 Hz), 7.88–8.00 (2H, m), 8.31 (1H, d, J=7.3 Hz), 8.69 (1H, d, J=7.0 Hz), 8.84 (1H, br. s). MS (ES⁺) 416 M+1). MP 189–191° C. C₂₂H₂₁N₇O₂.H₂O requires; C, 60.96; H, 5.35; N. 22.62%. Found: C, 60.97; H, 5.15; N, 22.52%.

EXAMPLE 6

Dimethyl-(1-methyl-1-{2-[3-(5-methyl-isoxazol-3-yl)-{1,2,4]triazolo[3,4-α]phthalazin-6-yloxymethyl]pyridin-5-yl}ethyl)amine NaBH(OAc)s (306 mg, 1.44 mmol) was added to a stirred solution of 1-methyl-1-{2-[3-(5-methylisoxazol-3-yl)-[1,2,4]triazolo[3,4-α]phthalazin-6-yloxymethyl]pyridin-5-yl}ethylamine (100 mg, 0.24 mmol), formaldehyde (37% (w/w) in H₂O, 49 μl, 0.6 mmol) in 1,2-dichloroethane (10 ml) at room temperature. The reaction mixture was stirred for 2 h and then quenched by addition of NaOH (2N, 10 ml). The organics were extracted using CH₂Cl₂ (2×50 ml) then the combined extracts were dried (MgSO₄) and concentrated under reduced pressure. The resulting white solid was recrystallised from CH₂Cl₂/iso-hexane to yield the title amine (80 mg, 75%).

¹H NMR (360 MHz, d₆-DMSO) δ 1.32 (6H, s), 2.08 (6H, s), 2.57 (3H, s), 5.69 (2H, s), 6.96 (1H, s), 7.68 (1H, d, J=8.2 Hz), 7.88–8.00 (2H, m), 8.11 (1H, t, J=7.7 Hz), 8.32 (1H, d, J=7.9 Hz), 8.57 (1H, d, J=8.0 Hz), 8.73 (1H, br. s.). MS (ES⁺) 444 (M+1). MP 173–177° C.

C₂₄H₂₅N₇O₂.0.5 (H₂O) requires: C, 63.70; H, 5.79; N, 21.67%. Found: C, 63.70; H, 5.45; N, 21.41%.

EXAMPLE 7

3-(5-Methylisoxazol-3-yl)-6-[5-(1-methylpyrrolidin-2-yl)pyridin-2-ylmethoxy]-[1,2,4]triazolo[3,4-α] phthalazine Step 1: 2-Bromo-5-(1-methylpyrrolidin-2-yl)pyridine A solution of BuLi (16.9 mmol) in hexanes (1.6 M, 10.6 ml) was added to a stirred solution of 2,5-dibromopyridine (40 g, 16.9 mmol) in Et₂O (300 ml) at –78° C. under N₂. The resulting suspension was then stirred at –78° C. for 1 h. N-Methyl pyrrolidinone (1.62 ml, 16.9 mmol) was added and the reaction allowed to warm slowly to room temperature and then stirred at RT for a further 1 h. NH₄Cl solution (50 ml) was added and the organics were extracted with Et₂O (3×100 ml). The combined organics were washed with brine (50 ml) and then concentrated under reduced pressure. The crude residue was taken up in 1,2-dichloroethane (50 ml), sodium triacetoxyborohydride (3.94 g, 16.9 mmol) was added portionwise and then the reaction mixture was stirred at room temperature overnight. 2 N NaOH solution (50 ml) was added and the organics were extracted with CH₂Cl₂ (3×100 ml), dried (MgSO₄), and concentrated under reduced pressure. The resulting crude residue was purified by column chromatography on silica using 3% MeOH/CH₂Cl₂ containing 1% NH₃ to yield the desired pyridine (480 mg, 10%). m/z (ES⁺) 241, 243 (1:1, M+H⁺).

Step 2: [5-(1-Methylpyrrolidin-2-yl)-pyridin-2-yl]methanol

A solution of BuLi (3.0 mmol) in hexanes (1.6 M, 1.87 ml) was added to a stirred solution of 2-bromo-5-(1-methylpyrrolidin-2-yl)pyridine (480 mg, 2.0 mmol) in THF (50 ml) at −78° C. under N₂. The reaction was stirred at −78° C. for 10 min, DMF (462 μl, 6.0 mmol) was added and the reaction allowed to warm slowly to room temperature and stirred at room temperature for a further 1 h. MeOH (50 ml) was added, followed by sodium borohydride (75 mg, 2.0 mmol) and then the reaction mixture was stirred at room temperature for 1 h. NH₄Cl solution (10 ml) was added cautiously. The resulting mixture was concentrated under reduced pressure, then dissolved in MeOH/CH₂Cl₂ (1:1, 50 ml) and dry loaded onto silica. The crude residue was purified by column chromatography on silica using 5% MeOH/CH₂Cl₂ containing 1% NH₃ to yield the desired hydroxymethylpyridine (100 mg, 26%). ¹H NMR (400 MHz, CDCl₃) δ 8.46 (1H, d, J=2.0 Hz), 7.70 (1H, dd, J=8.0, 2.0 Hz), 7.25 (1H, d, J=8.0 Hz), 4.75 (2H, s), 4.18 (1H, broad s), 3.28–3.18 (1H, m), 3.09 (1H, J=8.3 Hz), 2.31 (1H, q, J=9.0 Hz), 2.22–2.16 (1H, m), 2.16 (3H, s), 2.05–1.65 (3H, m). m/z (ES⁺) 193 (M+H⁺).

Step 3: 3-(5-Methylisoxazol-3-yl)-6-[5-(1-methylpyrrolidin-2-yl)pyridin-2-ylmethoxyl-[1,2,4]triazolo[3,4-α]phthalazine The reaction was carried out according to Example 1 step 4 using the [5-(1-methyl-pyrrolidin-2-yl)pyridin-2-yl]methanol (100 mg, 0.52 mmol) and 6-chloro-3-(5-methylisoxazol-3-yl)-[1,2,4]triazolo[3,4-α]phthalazine (149 mg, 0.52 mmol). The crude residue was purified by column chromatography on silica using 2% MeOH/CH₂Cl₂ containing 1% NH₃ to yield, after recystallisation from CH₂Cl₂/iso-hexanes, the desired phthalazine (107 mg, 47%). ¹H NMR (400 MHz, CDCl₃) δ 8.69 (1H, d, J=7.8 Hz), 8.58 (1H, s), 8.32 (1H, d, J=8.0 Hz), 7.97 (1H, t, J=8.0 Hz), 7.78–7.70 (3H, m), 6.83 (1H, s), 5.75 (2H, s), 3.25 (1H, broad s), 3.14 (1H, broad s), 2.59 (3H, s), 2.40–1.50 (8H, m). m/z (ES⁺) 441 (M+h⁺).

EXAMPLE 8

N,N-Dimethyl-2-[5-({[3-(5-methylisoxazol-3-yl)[1,2,4]triazolo[3,4-α]phthalazin-6-yl]oxyl}methyl)-1H-[1,2,3]triazol-1-yl]ethylamine Step 1: Ethyl 1-(2-{[1,1-dimethylethyl)(dimethyl)silyl]oxy]ethyl)-1H-1,2,3-triazole-5-carboxylate and ethyl 1-(2-{[1,1-dimethylethyl)(dimethyl)silyl]oxy]ethyl)-1H-1,2,3-triazole-4-carboxylate Sodium azide (978 mg, 15.0 mmol) was added to a stirred solution of 2-(tert-butyldimethylsilanyloxy)ethyl bromide (3.0 g, 12.5 mmol) in DMF (40 ml) at room temperature under N₂, the reaction heated at 80° C. for 1 h and then cooled to room tempertaure. H₂O (300 ml) was added and then the organics were extracted with Et₂O (700 ml and 200ml). The combined organic extracts were washed with H₂O (5×150 ml), brine (50 ml), dried (MgSO₄) and concentrated under reduced pressure. Ethyl propiolate (4.8 ml, 47 mmol) and toluene (50 ml) were added and the reaction mixture was heated at 80° C. overnight and then concentrated under reduced pressure. The resulting crude residue was purified by column chromatography on silica using 30 to 70% Et₂O/iso-hexanes to yield first the desired ethyl 1-(2-{[1,1-dimethylethyl)(dimethyl)silyl]oxy]ethyl)-1H-1,2,3-triazole-5-carboxylate (725 mg, 19%) and then ethyl 1-(2-{[1,1-dimethylethyl)(dimethyl)silyl]oxy]ethyl)-1H-1,2,3-triazole-4-carboxylate (2.16 g, 58%).

ethyl 1-(2-{[1,1-dimethylethyl)(dimethyl)silyl]oxy]ethyl)-1H-1,2,3-triazole-5-carboxylate: ¹H NMR (400 MHz, CDCl₃) δ 8.18 (1H, s), 4.97 (2H, t, J=5.6 Hz), 4.45 (2H, q, J=7.2 Hz), 4.09 (2H, t, J=5.6 Hz), 1.47 (3H, t, J=7.2 Hz), 0.87 (9H, s), 0.00 (6H, s). m/z (ES⁺) 300 (M+H⁺).

ethyl 1-(2-{[1,1-dimethylethyl)(dimethyl)silyl]oxy]ethyl)-1H-1,2,3-triazole-4-carboxylate: ¹H NMR (400 MHz, CDCl₃) δ 8.20 (1H, s), 4.55 (2H, t, J=5.4 Hz), 4.45 (2H, q, J=7.8 Hz), 4.00 (2H, t, J=5.4 Hz), 1.43 (3H, t, J=7.8 Hz), 0.87 (9H, s), 0.00 (6H, s). m/z (ES⁺) 300 (M+H⁺).

Step 2: [1-(2-{[(1,1-Dimethylethyl)(dimethyl)silyl]oxy}ethyl)-1H-1,2,3-triazol-5-yl]methanol A solution of DIBAL (5.37 mmol) in THF (1.0 M, 5.37 ml) was added dropwise to a stirred solution of the ethyl 1-(2-{[1,1-dimethylethyl)(dimethyl)silyl]oxy]ethyl)-1H-1,2,3-triazole-5-carboxylate (0.73 g, 2.44 mmol) in THF (40 ml) cooled to −78° C. under N₂. The reaction was allowed to warm to room temperature and then stirred for a further 3 h. Further DIBAL (5.37 mmol) was added and the reaction was stirred overnight. The reaction was quenched by sequential addition of H₂O (2.94 ml), EtOAc (200 ml), NaHCO₃ (1.07 g) and Na₂SO₄ (9.5 g) and then stirred for 2 h at room temperature. The resulting solid was filtered off, washed with EtOAc (200ml) and then the filtrate was concentrated under reduced pressure. The crude residue was purified by column chromatography on silica using 5% MeOH/CH₂Cl₂ to yield the desired the alcohol (387 mg, 61%). ¹H NMR (400 MHz, CDCl₃) δ 7.58 (1H, s), 4.78 (2H, s), 4.57 (2H, t, J=5.6 Hz), 4.09 (2H, t, J=5.6 Hz), 3.70 (1H, broad s), 0.84 (9H, s), 0.00 (6H, s).

Step 3: 6-({[1-(2-{[(Dimethylethyl)(dimethyl)silyl]oxy}ethyl)-1H-[1,2,3]triazol-5-yl]oxy)-3-(5-methylisoxazol-3-yl)-[1,2,4]triazolo[3,4-α]phthalazine The reaction was carried out according to Example 1 Step 4 using [1-(2-{[(1,1-dimethylethyl)(dimethyl)silyl]oxy}ethyl)-1H-1,2,3-triazol-5-yl]methanol (387 mg, 1.50 mmol) and 6-chloro-3-(5-methylisoxazol-3-yl)-[1,2,4]triazolo[3,4-αphthalazine (430 mg, 1.50 mmol). The crude residue was purified by column chromatography on silica using 2% MeOH/CH₂Cl₂ to yield the desired phthalazine (606 mg, 80%). ¹H NMR (400 MHz, CDCl₃) δ 8.74 (1H, d, J=8.2 Hz), 8.22 (1H, d, J=8.2 Hz), 8.12 (1H, s), 8.02 (1H, t, J=8.2 Hz), 7.87 (1H, t, J=8.2 Hz), 6.88 (1H, s), 5.91 (2H, s), 4.74 (2H, t, J=5.2 Hz), 4.13 (2H,t, J=5.2 Hz), 2.64 (3H, s), 0.66 (9H, s), 0.00 (6H, s). m/z (ES⁺) 507 (M+H⁺).

Step 4: 2-[5-({[3-(5-Methylisoxazol-3-yl)-[1,2,4]triazolo[3,4-α]phthalazin-6-yl]oxy}methyl]-1H-[1,2,3]triazol-1-yl]ethanol A solution of 6-({[1-(2-{[(dimethylethyl)(dimethyl)silyl]oxy}ethyl)-1H-[1,2,3]triazol-5-yl]methyl}oxy)-3-(5-methylisoxazol-3-yl)-[1,2,4]triazolo[3,4-α]phthalazine (606 mg, 1.2 mmol) and pyridinium para-toluenesulfonate (602 mg, 2.4 mmol) in EtOH (100 ml) was heated at 70° C. for 36 h. The reaction was cooled to room temperature and concentrated to approximately 25 ml, the resulting solid was filtered off and dried to yield the desired phthalazine (429 mg, 91%). ¹H NMR (360 MHz, d⁶-DMSO) δ 8.55 (1H, d, J=8.0 Hz), 8.22 (1H, d, J=8.0 Hz), 8.12–8.00 (2H, m), 7.93 (1H, t, J=8.0 Hz), 7.11 (1H, s), 5.83 (2H, s), 4.58 (2H, t, J=5.3 Hz), 3.84 (2H, t, J=5.3 Hz), 2.59 (3H, s).

Step 5: 6-({[1-(2-Bromoethyl)-1H-1,2,3-triazol-5-yl]methyl}oxy)-3-(5-methylisoxazol-3-yl)-[1,2,4]triazolo[3,4-α]-phthalazine A suspension of 2-[5-({[3-(5-methylisoxazol-3-yl)-[1,2,4]triazolo[3,4-α]phthalazin-6-yl]oxymethyl]-1H-[1,2,3]triazol-1-yl]ethanol (429 mg, 1.1 mmol) in CH₂Cl₂ (25 ml) was treated with thionyl bromide (500 μl) at room temperature under N$_2$ and the mixture was stirred at room temperature for 1 h, during which time the compound appeared to go into solution and then precipitate again. The reaction mixture was concentrated under reduced pressure, then taken up in MeOH/CH$_2$Cl$_2$ and dry loaded onto silica. Column chromatography on silica using 2% MeOH/CH$_2$Cl$_2$ containing 1% NH$_3$ as eluent yielded the desired bromide (429 mg, 25%). $^1$H NMR (360 MHz, CDCl$_3$) δ 8.68 (1H, d, J=7.6 Hz), 8.16 (1H, d, J=7.6 Hz), 8.11 (1H, s), 7.98 (1H, t, J=7.6 Hz), 7.83 (1H, t, J=7.6 Hz), 6.85 (1H, s), 5.87 (2H, s), 4.99 (2H, t, J=6.4 Hz), 3.89 (2H, t, J=6.4 Hz), 2.58 (3H, s). m/z (ES$^+$) 455, 457 (1:1, M+H$^+$).

Step 6: N,N-Dimethyl-2-[5-({[3-(5-methylisoxazol-3-yl)[1,2,4]triazolo[3,4-α]phthalazin-6-yl]oxy}methyl)-1H-[1,2,3]triazol-1-yl]ethylamine A solution of 6-({[1-(2-bromoethyl)-1H-1,2,3-triazol-5-yl]methyl}oxy)-3-(5-methylisoxazol-3-yl)-[1,2,4]triazolo[3,4-α]phthalazine (125 mg, 0.27 mmol) in DMF (5 ml) and Me$_2$NH (2.0 M in THF, 4 ml, 8 mmol) were heated at 80° C. for 4 h in a sealed tube. The reaction mixture was concentrated under reduced pressure and then taken up in MeOH/CH$_2$Cl$_2$ and dry loaded onto silica. The mixture was purified by column chromatography on silica using 1.5% MeOH/CH$_2$Cl$_2$ containing 1% NH$_3$ as eluent to yield the desired phthalazine (50 mg, 44%). $^1$H NMR (360 MHz, CDCl$_3$) δ 8.69 (1H, d, J=8.0 Hz), 8.18 (1H, d, J=8.0 Hz), 8.07 (1H, s), 7.98 (1H, t, J=7.6 Hz), 7.82 (1H, t, J=7.6 Hz), 6.85 (1H, s), 5.86 (2H, s), 4.66 (2H, t, J=6.9 Hz), 2.92 (2H, m), 2.59 (3H, s), 2.32 (6H, s). m/z (ES$^+$) 420 (M+H$^+$).

EXAMPLE 9

Dimethyl-(2-{4-[3-(5-methylisoxazol-3-yl)-[1,2,4]triazolo[3,4-α]phthalazin-6-yloxymethyl]-[1 2,3]triazol-1-yl}ethyl)amine Step 1: {1-[2-(tert-Butyldimethylsilanyloxy)ethyl]-1H-[1,2,3]triazol-4-yl}methanol The reaction was carried out as described in Example 8 step 2 using ethyl 1-(2-{[1,1-dimethylethyl)(dimethyl)silyl]oxy]ethyl)-1H-1,2,3-triazole-4-carboxylate (1.67 g, 7.22 mmol) to yield without chromatography the desired alcohol (1.67 g, 90%). $^1$H NMR (400 MHz, CDCl$_3$) δ 7.64 (1H, s), 4.79 (2H, s), 4.46 (2H, t, J=5.2 Hz), 3.98 (2H, t, J=5.2 Hz), 0.85 (9H, s), −0.02 (6H, s).

Step 2: 6-{1-[2-(tert-Butyldimethylsilanyloxy)ethyl]-1H-[1,2,3]triazol-4-ylmethoxy}-3-(5-methylisoxazol-3-yl)-[1,2,4]triazolo[3,4-α]phthalazine The reaction was carried out according to Example 1 step 4 using {1-[2-(tert-butyldimethylsilanyloxy)ethyl]-1H-[1,2,3]triazol-4-yl}methanol (1.67 g, 6.49 mmol) and 6-chloro-3-(5-methylisoxazol-3-yl)-[1,2,4]triazolo[3,4-α]phthalazine (1.85 g, 6.49 mmol). The crude residue was purified by column chromatography on silica using 2–3% MeOH/CH$_2$Cl$_2$ containing 1% NH$_3$ to yield the desired phthalazine (2.82 g, 86%). $^1$H NMR (400 MHz, CDCl$_3$) δ 8.75–8.70 (2H, m), 8.23 (1H, d, J=8.5 Hz), 7.94 (1H, t, J=8.5 Hz), 7.80 (1H, t, J=8.5 Hz), 6.91 (1H, s), 5.79 (2H, s), 4.46 (2H, t, J=5.7 Hz), 3.99 (2H, t, J=5.2 Hz), 2.60 (3H, s), 0.67 (9H, s), −0.16 (6H, s). m/z (ES$^+$) 507 (M+H$^+$).

Step 3: 2-{4-[3-(5-Methylisoxazol-3-yl)-[1,2,4]triazolo[3,4-α]phthalazin-6-yloxymethyl]-[1,2,3]triazol-1-yl}ethanol The reaction was carried out according to Example 8 step 4 using 6-{1-[2-(tert-butyldimethylsilanyloxy)ethyl]-1H-[1,2,3]triazol-4-ylmethoxy}-3-(5-methylisoxazol-3-yl)-[3,4-α]phthalazine (600 mg, 1.18 mmol) and pyridinium para-toluenesulfonate (595 mg, 2.37 mmol) to yield the desired alcohol (354 g, 76%). $^1$H NMR (400 MHz, d$^6$-DMSO) δ 8.55 (1H, d, J=7.9 Hz), 8.44 (1H, s), 8.17 (1H, d, J=7.9 Hz), 8.09 (1H, t, J=7.9 Hz), 7.91 (1H, t, J=7.9 Hz), 7.17 (1H, s), 5.70 (2H, s), 4.43 (2H, t, J=5.4 Hz), 3.79 (2H, t, J=5.4 Hz), 2.59 (3H, s).

Step 4: Dimethyl-(2-{4-[3-(5-methylisoxazol-3-yl)-[1,2,4]triazolo[3,4-α]phthalazin-6-yloxymethyl]-[1,2,3]triazol-1-yl}ethyl)amine Mesyl chloride (349 μl, 4.5 mmol) was added to a stirred suspension of 2-{4-[3-(5-methylisoxazol-3-yl)-[1,2,4]triazolo[3,4-α]phthalazin-6-yloxymethyl]-[1,2,3]triazol-1-yl}ethanol (354 mg, 0.9 mmol) in Et$_3$N (629 μl, 4.5 mmol) and CH$_2$Cl$_2$ (50 ml) at 0° C. under N$_2$. The reaction was stirred overnight slowly warming to room temperature. H$_2$O (20 ml) was added and the organics separated, dried and concentrated under reduced pressure. The crude residue was taken up in DMF (5 ml) in a sealed tube and a solution of Me$_2$NH (8 mmol) in THF (2.0 M, 4 ml) was added. The reaction was heated at 80° C. for 4 h. The reaction mixture was concentrated under reduced pressure and then taken up in MeOH/CH$_2$Cl$_2$ and dry loaded onto silica. The mixture was purified by column chromatography on silica using 1.5% MeOH/CH$_2$Cl$_2$ containing 1% NH$_3$ as eluent to yield the desired phthalazine (30 mg, 8%). $^1$H NMR (360 MHz, CDCl$_3$) δ 8:85 (1H, s), 8.64 (1H, d, J=7.4 Hz), 8.24 (1H, d, J=7.4 Hz), 7.93 (1H, t, J=7.4 Hz), 7.80 (1H, t, J=7.4 Hz), 6.90 (1H, s), 5.77 (2H, s), 4.46 (2H, t, J=6.5 Hz), 2.92 (2H, t, J=6.5 Hz), 2.60 (3H, s), 2.24 (6H, s). m/z (ES$^+$) 420 (M+H$^+$).

EXAMPLE 10

3-(5-Methylisoxazol-3-yl)-6-(6-[morpholin-4-yl]pyridin-2-ylmethoxy)[1,2,4]triazolo-[3,4-α]phthalazine Step 1: 4-[6-(tert-Butyldimethylsilanyloxymethyl)-pyridin-2-yl]morpholine A solution of 2-bromo-6-(tert-butyldimethylsilanyloxymethyl)pyridine (*J. Org. Chem.*; 1993; 4389–4397) (500 mg, 1.66 mmol), morpholine (173 μl, 2.0 mmol), 1,3-bis(diphenylphosphino)propane (68 mg, 10 mol %) in toluene (20 ml) was degassed with a stream of N$_2$ for 15 min. Sodium tert-butoxide (222 mg, 2.31 mmol) and Pd$_2$(dba)$_3$ (76 mg, 5 mol %) were added and the reaction mixture was heated at 70° C. overnight under N$_2$. After cooling to room temperature, Et$_2$O (100 ml) was added and the solution was washed with brine (25 ml), dried and concentrated under reduced. The mixture was purified by column chromatography on silica using 30% Et$_2$O/isohexanes as eluent to yield the desired aminopyridine (370 mg, 72%). $^1$H NMR (400 MHz, CDCl$_3$) δ 7.40 (1H, dd, J=8.6, 7.4 Hz), 6.75 (1H, d, J=7.4 Hz), 6.38 (1H, d, J=8.6 Hz), 4.56 (2H, s), 3.70 (4H, t, J=5.0 Hz), 3.36 (4H, t, J=5.0 Hz), 0.84 (9H, s), 0.00 (6H, s). m/z (ES$^+$) 309 (M+H$^+$).

Step 2: (6-(Morpholin-4-yl)-pyridin-2-yl)methanol

A solution of tetrabutylammonium fluoride (1.44 mmol) in THF (1.0 M, 1.44 ml) was added to a stirred solution of 4-[6-(tert-butyldimethylsilanyloxymethyl)-pyridin-2-yl]morpholine (370 mg, 1.2 mmol) in THF (10 ml) at room temperature under N$_2$ and the reaction mixture was stirred at room temperature for 1 h. H$_2$O (30 ml) was added and the organic were extracted with EtOAc (150 ml), then washed with brine (50 ml), dried and concentrated under reduced. The mixture was purified by column chromatography on silica using 100% Et$_2$O as eluent to yield the desired hydroxymethylpyridine (192 mg, 82%). $^1$H NMR (360 MHz, CDCl$_3$) δ 7.49 (1H, dd, J=8.4, 7.4 Hz), 6.57 (1H, d, J=7.4 Hz), 6.51 (1H, d, J=8.4 Hz), 4.62 (2H, s), 3.83 (4H, t, J=4.9 Hz), 3.50 (4H, t, J=4.9 Hz).

Step 3: 3-(5-Methylisoxazol-3-yl)-6-(6-[morpholin-4-yl]pyridin-2-ylmethoxy)[1,2,4]triazolo-[3,4-α]phthalazine The reaction was carried out according to Example 1 step 4 using (6-(morpholin-4-yl)pyridin-2-yl)methanol (96 mg, 0.49 mmol) and 6-chloro-3-(5-methylisoxazol-3-yl)-[1,2,4]triazolo[3,4-α]phthalazine (141 mg, 0.49 mmol). The crude residue was purified by column chromatography on silica using 2% MeOH/CH$_2$Cl$_2$ containing 1% NH$_3$ to yield, after recrystallisation from CH$_2$Cl$_2$/iso-hexanes, the desired phthalazine (101 mg, 46%). $^1$H NMR (360 MHz, CDCl$_3$) δ 8.70 (1H, d, J=8.1 Hz), 8.31 (1H, d, J=8.0 Hz), 8.00–7.91 (1H, m), 7.85–7.78 (1H, m), 7.58–7.50 (1H, m), 6.97 (1H, d, J=7.2 Hz), 6.80 (1H, s), 6.61 (1H, d, J=8.5 Hz), 5.60 (2H, s), 3.82 (4H, t, J=5.1 Hz), 3.54 (4H, t, J=5.1 Hz), 2.57 (3H, s). m/z (ES$^+$) 444 (M+H$^+$).

EXAMPLE 11

6-[5-(2-(Azetidin-1-yl)ethyl)-1-methyl-1H-[1,2,3]triazol-4-ylmethoxy-3-(5-methyl-isoxazol-3-yl)-[1,2,4]triazolo[3,4-α]phthalazine Step 1: 4-(tert-Butyldimethylsilanyloxymethyl)-1-methyl-1H-[1,2,3]triazole A mixture of 4-hydroxymethyl-1-methyl-1H-[1,2,3]triazole hydrochloride hydrate (WO-A-9850385) (7.0 g, 41.8 mmol), tert-butyldimethylsilyl chloride (6.3 g, 41.8 mmol), Et$_3$N (11.6 ml, 83.6 mmol) and 4-(dimethylamino)pyridine (255 mg, 5 mol %) in CH$_2$Cl$_2$ (250 ml) was stirred at room temperature overnight under N$_2$. Iso-hexanes (400 ml) were added and the resulting precipitate was removed by filtration. The filtrate was concentrated under reduced pressure and the mixture was purified by column chromatography on silica using 10–100% Et$_2$O/iso-hexanes as eluent to yield the desired protected alcohol (8.90 g, 94%). $^1$H NMR (360 MHz, CDCl$_3$) δ 7.35 (1H, s), 4.73 (2H, s), 3.98 (3H, s), 0.81(9H, s), 0.00 (6H, s).

Step 2: 2-[4-({[1,1-Dimethylethyl)(dimethyl)silyl]oxy}methyl)-1-methyl-1H-[1,2,3]triazol-5-yl]ethanol A solution of BuLi (43.5 mmol) in hexanes (1.6 M, 27.2 ml) was added to a stirred solution of 4-(tert-butyldimethylsilanyloxymethyl)-1-methyl-1H-[1,2,3]triazole (8.90 g, 39.5 mmol) in THF (200 ml) at −78° C. under N$_2$. The resulting suspension was stirred at −78° C. for 45 min. A solution of ethylene oxide (5.69 g, 0.12 mol) in THF (40 ml) was added and the reaction allowed to warm slowly to room temperature and then stirred at room temperature for a further 1 h. NH$_4$Cl solution (50 ml) was added and the organics were extracted with CH$_2$Cl$_2$ (2×100 ml). The combined organic extracts were washed with brine (50 ml), dried and then concentrated under reduced pressure while dry loading onto silica. The mixture was purified by column chromatography on silica using 5–10% MeOH/CH$_2$Cl$_2$ as eluent to yield the desired hydroxyethyltriazole (7.41 g, 70%). 1H NMR (400 MHz, CDCl$_3$) δ 4.67 (2H, s), 3,86 (3H, s), 3.72 (2H, t, J=5.2 Hz), 2.85 (2H, t, J=5.2 Hz), 0.78 (9H, s), 0.00 (6H, s). m/z (ES$^+$) 272 (M+H$^+$).

Step 3: 2-[4-({[(1,1-Dimethylethyl)(dimethyl)silyl]oxy}methyl)-1-methyl-1H-1,2,3-triazol-5-yl]ethyl methanesulphonate Mesyl chloride (314 μl, 4.06 mmol) was added dropwise over 2 min to a stirred solution of 2-[4-({[1,1-dimethylethyl)(dimethyl)silyl]oxy}methyl)-1-methyl-1H-[1,2,3]triazol-5-yl]ethanol (1.0 g, 3.69 mmol) and Et$_3$N (620 □l, 4.4 mmol) in CH$_2$Cl$_2$ (15 ml) at 0° C. under N$_2$. The reaction was stirred for 30 min at 0° C., then diluted with CH$_2$Cl$_2$ (150 ml) and washed with 1 N HCl (70 ml), NaHCO$_3$ solution (70 ml) and brine (70 ml). The solution was dried and concentrated under reduced pressure to yield the desired mesylate (1.42 g, 99%) which was used without further purification. $^1$H NMR (400 MHz, CDCl$_3$) δ 4.73 (2H, s), 4.33 (2H, t, J=6.4 Hz), 4.04 (3H, s), 3.09 (2H, t, J=6.4 Hz), 2.76 (3H, s), 0.78 (9H, s), 0.00 (6H, s). m/z (ES$^+$) 350 M+H$^+$).

Step 4: [5-(2-(Azetidin-1-yl)ethyl)-1-methyl-1H-[1,2,3]triazol-4-yl]methanol

A solution of 2-[4-({[(1,1-dimethylethyl)(dimethyl)silyl]oxy}methyl)-1-methyl-1H-1,2,3-triazol-5-yl]ethyl methanesulphonate (642 mg, 1.84 mmol) and azetidine (2.48 ml, 18.4 mmol) in THF (10 ml) was heated at reflux for 4 h and then concentrated under reduced pressure while dry loading onto silica. The mixture was purified by column chromatography on silica using 2% MeOH/CH$_2$Cl$_2$ containing 1% NH$_3$ solution as eluent. After concentrating under reduced pressure, THF (3 ml), H$_2$O (3ml) and AcOH (9 ml) were added and the mixture stirred at RT for 60 h. The solvents were removed under reduced pressure while azeotroping with toluene (2×25 ml). The residue was dissolved in CH$_2$Cl$_2$, dry loaded onto silica and purified by column chromatography on silica using 15% MeOH/CH$_2$Cl$_2$ containing 1% NH$_3$ solution as eluent to yield the desired hydroxymethyltriazole (103 mg, 29%). $^1$H NMR (360 MHz, CDCl$_3$) δ 4.65 (2H, s), 3.94 (3H, s), 3.25 (4H, t, J=7.2 Hz), 2.76–2.62 (4H, m), 2.11 (2H, quintet, 7.2 Hz). m/z (ES$^+$) 196 (M+H$^+$).

Step 5: 6-[5-(2-(Azetidin-1-yl)ethyl)-1-methyl-1H-[1,2,3]triazol-4-ylmethoxy]-3-(5-methyl-isoxazol-3-yl)-[1,2,4]triazolo[3,4-α]phthalazine The reaction was carried out according to Example 1 step 4 using [5-(2-(azetidin-1-yl)ethyl)-1-methyl-1H-[1,2,3]triazol-4-yl]methanol (103 mg, 0.53 mmol) and 6-chloro-3-(5-methylisoxazol-3-yl)-[1,2,4]triazolo[3,4-α]phthalazine (150 mg, 0.53 mmol). The crude residue was purified by column chromatography on silica using 2% MeOH/CH$_2$Cl$_2$ containing 1% NH$_3$ to yield, after recrystallisation from CH$_2$Cl$_2$/iso-hexanes, the desired phthalazine (104 mg, 44%). $^1$H NMR (360 MHz, CDCl$_3$) δ 8.68 (1H, d, J=7.9 Hz), 8.19 (1H, d, J=7.9 Hz), 7.95 (1H, t, J=7.9 Hz), 7.78 (1H, t, J=7.9 Hz), 6.95 (1H, s), 5.75 (2H, s), 4.07 (3H, s), 3.11 (4H, t, J=6.9 Hz), 2.84 (2H, t, J=7.1 Hz), 2.65–2.50 (5H, m), 1.99 (2H, quintet, J=6.9 Hz). m/z (ES$^+$) 446 (M+H$^+$).

EXAMPLE 12

4-[5-({[3-(5-Methylisoxazol-3-yl)[1,2,4]triazolo[3,4-α]phthalazin-6-yl]oxy}methyl)pyridin-2-yl]piperidin-4-ol Step 1: 1,1-Dimethylethyl 4-hydroxy-4-[5-hydroxymethylpyridin-2-yl]-1-piperidine carboxylate A solution of BuLi (9.94 mmol) in hexanes (1.6 M, 6.2 ml) was added dropwise over 3 min to a stirred solution of 2-bromo-5-(tert-butyldimethylsilyloxymethyl)pyridine (2.0 g, 6.63 mmol) in THF (40 ml) at −78° C. under N$_2$. The resulting solution was then stirred at −78° C. for 30 min and a solution of N-Boc-4-piperidone (1.95 g, 9.93 mmol) in THF (20 ml) was added. The reaction was allowed to warm to room temperature and stirred for a further 15 min. NH$_4$Cl solution (40 ml) was added and the organics were extracted with EtOAc (3×50 ml). The combined organics were washed with brine (50 ml) and then concentrated under reduced pressure. A solution of tetrabutylammonium fluoride(6.63 mmol) in THF (1.0 M, 6.63 ml) was added to a stirred solution of the crude silyl ether in THF (100 ml) at room temperature under N$_2$ and the reaction mixture was stirred for 1 h. NH$_4$Cl solution (40 ml) was added and the organic were extracted with EtOAc (3×50 ml), then washed with brine (50 ml), dried and concentrated under reduced. The mixture was purified by column chromatography on silica using 100% EtOAc as eluent to yield the desired hydroxymethylpyridine (0.89 g, 44%). $^1$H NMR (360 MHz, CDCl$_3$) δ

8.48 (1H, s), 7.74 (1H, d, J=8.1 Hz), 7.32 (1H, d, J=8.1 Hz), 4.72 (1H, broad s), 4.10 (2H, s), 4.10–4.00 (2H, m), 3.30–3.20 92H, m), 1.89 (2H, td, J=8.1, 4.9 Hz), 1.56 92H, d, J=8.1 Hz), 1.47 (9H, s). m/z (ES$^+$) 423 (M+H$^+$).

Step 2: 1,1-Dimethylethyl 4-hydroxy-4-[5-({[3-(5-methylisoxazol-3-yl)}1,2,4]triazolo[3,4-α]phthalazin-6-yl] oxy}methyl)pyridin-2-yl]-1-piperidine carboxylate The reaction was carried out according to Example 1 Step 4 using 1,1-dimethylethyl 4-hydroxy-4-[5-hydroxymethylpyridin-2-yl]-1-piperidine carboxylate (490 mg, 1.59 mmol) and 6-chloro-3-(5-methylisoxazol-3-yl)-[1,2,4]triazolo[3,4-α]phthalazine (454 mg, 1.59 mmol). The crude residue was purified by column chromatography on silica using 2.5% MeOH/CH$_2$Cl$_2$ containing 1% NH$_3$ to yield the desired phthalazine (707 mg, 80%). $^1$H NMR (360 MHz, CDCl$_3$) δ 8.85 (1H, s), 8.68 (1H, d, J=8.0 Hz), 8.22 (1H, d, J=8.0 Hz), 8.15 (1H, dd, J=8.1, 2.1 Hz), 7.96 (1H, t, J=8.0 Hz), 7.81 (1H, t, J=8.0 Hz), 7.39 (1H, d, J=8.1 Hz), 6.85 (1H, s), 5.70 (2H, s), 4.20–4.00 (2H, broad s), 3.38–3.20 (2H, broad s), 2.61 (3H, s), 2.00–1.88 (2H, m), 1.65–1.55 (2H, m), 1.48 (9H, s).

Step 3: 4-[5-({[3-(5-Methylisoxazol-3-yl)[1,2,4]triazolo[3,4-α]phthalazin-6-yl}oxy}methyl)pyridin-2-yl]piperidin-4-ol Trifluoroacetic acid (3 ml) was added to a stirred solution of 1,1-dimethylethyl 4-hydroxy-4-[5-({[3-(5-methylisoxazol-3-yl){1,2,4]triazolo[3,4-α]phthalazin-6-yl] oxy}methyl)pyridin-2-yl]-1-piperidine carboxylate(707 mg, 1.27 mmol) in CH$_2$Cl$_2$ (30 ml) at room temperature and the reaction stirred for 6 h. The reaction mixture was concentrated under reduced pressure, 2N NaOH solution (30 ml) was added and the resulting precipitate was filtered off. After dissolving in MeOH/CH$_2$Cl$_2$ (60 ml) and dry loading onto alumina, the crude residue was purified by column chromatography on alumina using 5–7% MeOH/CH$_2$Cl$_2$ containing 1% NH$_3$ to yield the desired phthalazine (361 mg, 62%). $^1$H NMR (360 MHz, d$^6$-DMSO) δ 8.80 (1H, s), 8.55 (1H, d, J=7.1 Hz), 8.23 (1H, d, J=7.1 Hz), 8.15–8.03 (2H, m), 7.93 (1H, t, J=7.1 Hz), 7.71 (1H, d, J=7.4 Hz), 7.07 (1H, s), 5.67 (2H, s), 5.06 (2H, s), 2.91 (2H, t, J=11.2 Hz), 2.74 (2H, d, J=11.2 Hz), 2.60 (3H, s), 2.04 (2H, td, J=12.4, 4.0 Hz), 1.44 (2H, d, J=12.4 Hz). m/z (ES$^+$) 458 (M+H$^+$).

EXAMPLE 13

3-(5-Methylisoxazol-3-yl)-6-(1',2',3',6'-tetrahydro-[2,4']bipyridinyl-5-ylmethoxy)-[1,2,4]triazolo[3,4-α] phthalazine Step 1: 1,1-Dimethylethyl 5-({[3-(5-methylisoxazol-3-yl)[1,2,4]triazolo[3,4-α]phthalazin-6-yl]oxy}methyl)-3'6'-dihydro-2,4'-bipyridine-1'(2'H)-carboxylate Burgess reagent (262 mg, 1.1 mmol) was added to a stirred solution of 1,1-dimethylethyl 4-hydroxy-4-[5-({[3-(5-methylisoxazol-3-yl)[1,2,4]triazolo[3,4-α]phthalazin-6-yl]oxy}methyl)pyridin-2-yl]-1-piperidine carboxylate (307 mg, 0.55 mmol) in 1,2-dichloroethane (20 ml) at room temperature under N$_2$ and the reaction heated at reflux for 90 min. After cooling to room temperature, the reaction mixture was concentrated under reduced pressure while dry loading onto silica. The residue was purified by column chromatography on silica using 2% MeOH/CH$_2$Cl$_2$ containing 1% NH$_3$ to yield the desired phthalazine (296 mg, 99%). $^1$H NMR (360 MHz, CDCl$_3$) δ 8.86 (1H, s), 8.66 (1H, d, J=8.0 Hz), 8.20 (1H, d, J=8.0 Hz), 8.05–8.00 (1H, m), 7.95 (1H, t, J=8.0 Hz), 7.79 (1H, t, J=8.0 Hz), 7.43 (1H, d, J=8.1 Hz), 6.85 (1H, s), 6.66 (1H, m), 5.67 (2H, s), 4.17–4.11 (2H, m), 3.67–3.58 (2H, m), 2.68–2.60 (2H, m), 2.59 (3H, s), 1.49 (9H, s). m/z (ES$^+$) 540 (M+H$^+$).

Step 2: 3-(5-Methylisoxazol-3-yl)-6-(1',2',3',6'-tetrahydro-[2,4']bipyridinyl-5-ylmethoxy)-[1,2,4]triazolo[3,4-α] phthalazine The reaction was carried out according to Example 12 step 3 using 1,1-dimethylethyl 5-({[3-(5-methylisoxazol-3-yl)[1,2,4]triazolo[3,4-α]phthalazin-6-yl]oxy}methyl)-3'6'-dihydro-2,4'-bipyridine-1'(2'H)-carboxylate (296 mg, 0.55 mmol) and trifluoroacetic acid (5 ml). The crude residue was purified by column chromatography on silica using 7% MeOH/CH$_2$Cl$_2$ containing 1% NH$_3$ to yield the desired phthalazine (124 mg, 51%). $^1$H NMR (360 MHz, CDCl$_3$) δ 8.81 (1H, s), 8.68 (1H, d, J=7.6 Hz), 8.21 (1H, d, J=8.0 Hz), 8.05–7.90 (2H, m), 7.80 (1H, t, J=8.0 Hz), 7.43 (1H, t, J=8.1 Hz), 6.85 (1H, s), 6.75 (1H, broad s), 5.68 (2H, s), 3.60 (2H, q, J=2.9 Hz), 3.12 (2H, t, J=5.7 Hz), 2.67–2.55 (5H, m). m/z (ES$^+$) 440 (M+H$^+$).

EXAMPLE 14

3-(5-Methylisoxazol-3-yl)-6-(1-methyl-5-(piperidin-1-yl)methyl-1H-[1,2,3]triazol-4-ylmethoxy)-[1,2,4] triazolo[3,4-α]phthalazine Step 1: [4-({[(1,1-Dimethylethyl)(dimethyl)silyl] oxy}methyl)-1-methyl-1H-[1,2,3]triazol-5-yl]methanol A solution of BuLi (23.6 mmol) in hexanes (1.6 M, 14.7 ml) was added to a stirred solution of 4-(tert-butyldimethylsilanyloxymethyl)-1-methyl-1H-[1,2,3]triazole (3.00 g, 13.2 mmol) in THF (50 ml) at −78° C. under N$_2$. The resulting solution was stirred at −78° C. for 15 min, then warmed to −40° C. and recooled to −78° C. DMF (4.97 ml, 64.2 mmol) was added and the reaction was allowed to warm to room temperature. MeOH (50 ml) was added, followed by sodium borohydride (1.21 g, 32.1 mmol) and the reaction mixture was stirred at room temperature for 30 min. NH$_4$Cl solution (50 ml) was added cautiously. The organic solvents were removed under reduced pressure, then 4N NaOH solution (50 ml) was added and the organics were extracted with CH$_2$Cl$_2$ (3×100 ml). The combined organic extracts were washed with NH$_4$Cl solution (50 ml) and brine (50 ml), then dried and concentrated under reduced pressure. The crude residue was purified by column chromatography on silica using 3% MeOH/CH$_2$Cl$_2$ to yield the desired hydroxymethyltriazole (2.83 g, 83%). $^1$H NMR (360 MHz, CDCl$_3$) δ 4.77 (2H, s), 4.62 (2H, d, J=5.9 Hz), 3.90 (3H, s), 0.78 (9H, s), 0.00 (6H,s). m/z (ES$^+$) 258 (M+H$^+$).

Step 2: 4-({[(1,1-Dimethylethyl)(dimethyl)silyl] oxy}methyl)-5-({[(1,1-dimethylethyl)(diphenyl)silyl] oxy}methyl)-1-methyl-1H-1,2 3-triazole A mixture of [4-({[(1,1-dimethylethyl)(dimethyl)silyl] oxy}methyl)-1-methyl-1H-[1,2,3]triazol-5-yl]methanol (1.23 g, 4.79 mmol), tert-butyldiphenylsilyl chloride (1.25 g, 4.79 mmol), Et$_3$N (666 μl, 4.79 mmol) and 4-(dimethylamino)pyridine (29 mg, 5 mol %) in CH$_2$Cl$_2$ (50 ml) was stirred at room temperature for 72 h under N$_2$. Iso-hexanes (400 ml) were added and the resulting precipitate was removed by filtration. The filtrate was concentrated reduced and the mixture was purified by column chromatography on silica using 40% Et$_2$O/iso-hexanes as eluent to yield the desired bis-protected diol (1.77 g, 74%). $^1$H NMR (400 MHz, CDCl$_3$) δ 7.74–7.65 (4H, m), 7.55–7.40 (6H, m), 4.88 (2H, s), 4.56 (2H, s), 4.11 (3H, s), 1.10 (9H, s), 0.82 (9H, s), 0.00 (6H, s). m/z (ES$^+$) 496 (M+H$^+$).

Step 3: [5-({[(1,1-Dimethylethyl)(diphenyl)silyl] oxy}methyl)-1-methyl-1H-[1,2,3]triazol-4-yl]methanol Pyridinium para-toluenesulfonate (0.99 g, 3.94 mmol) was added to a stirred solution of 4-({[(1,1-dimethylethyl) (dimethyl)silyl]oxy}methyl)-5-({[(1,1-dimethylethyl) (diphenyl)silyl]oxy}methyl)-1-methyl-1H-1,2,3-triazole (1.77 g, 3.56 mmol) in EtOH (50 ml) and then heated at 50° C. for 6 h. The reaction mixture was concentrated under reduced pressure, then taken up in EtOAc (100 ml) and washed with $H_2O$ (100 ml), 2N NaOH (100 ml) and brine (100 ml). After drying, the solvents were removed under reduced pressure and the mixture was purified by column chromatography on silica using 10–100% $Et_2O$/iso-hexanes as eluent to yield the desired hydroxymethyltriazole (1.20 g, 89%). $^1$H NMR (360 MHz, $CDCl_3$) δ 7.68–7.60 (4H, m), 7.50–7.34 (6H, m), 4.78 (2H, s), 4.46 (2H, s), 4.02 (3H, s), 1.04 (9H, s). m/z ($ES^+$) 382 ($M+H^+$).

Step 4: 6-({[5-({[(1,1-Dimethylethyl)(diphenyl)silyl]oxy}methyl)-1-methyl-1H-[1,2,3]triazol-4-yl]methyl}oxy)-3-(5-methylisoxazol-3-yl)-[1,2,4]triazolo[3,4-α]phthalazine The reaction was carried out according to Example 1 step 4 using [5-({[(1,1-dimethylethyl)(diphenyl)silyl]oxy}methyl)-1-methyl-1H-[1,2,3]triazol-4-yl]methanol (1.20 g, 3.14 mmol) and 6-chloro-3-(5-methylisoxazol-3-yl)-[1,2,4]triazolo[3,4-α]phthalazine (0.90 mg, 3.14 mmol). The crude residue was purified by column chromatography on silica using 1–2% $MeOH/CH_2Cl_2$ containing 1% $NH_3$ to yield the desired phthalazine (1.90 g, 96%). $^1$H NMR (360 MHz, $CDCl_3$) δ 8.68 (1H, d, J=7.9 Hz), 7.99 (1H, d, J=7.9 Hz), 7.91 (1H, t, J=7.9 Hz), 7.69 (1H, t, J=7.9 Hz), 7.55 (4H, d, J=7.9 Hz), 7.34–7.18 (6H, m), 6.90 (1H, s), 5.43 (2H, s), 4.90 (2H, s), 4.10 (3H, s), 2.58 (3H, s), 0.99 (9H, s). m/z ($ES^+$) 632 ($M+2H^+$).

Step 5: [1-Methyl-4-({[3-(5-methylisoxazol-3-yl)[1,2,4]triazolo[3,4-α]phthalazine-6-yl]oxy}methyl)-1H-[1,2,3]triazol-5-yl]methanol A solution of tetrabutylammonium fluoride (3.3 mmol) in THF (1.0 M, 3.3 ml) was added to a stirred solution of 6-({[5-({[(1,1-dimethylethyl)(diphenyl)silyl]oxy}methyl)-1-methyl-1H-[1,2,3]triazol-4-yl]methyl}oxy)-3-(5-methylisoxazol-3-yl)-[1,2,4]triazolo[3,4-α]phthalazine (1.90 g, 3.3 mmol) in THF (50 ml) and MeOH (10 ml) at room temperature under $N_2$ and the reaction mixture was stirred overnight. $H_2O$ (10 ml) was added and then the mixture was concentrated under reduced pressure to remove the organic solvents. The resulting solid was filtered off, washed with $H_2O$ (20 ml), then triturated with $CH_2Cl_2$ (100 ml), filtered and dried, to yield the desired hydroxymethyltriazole (672 mg, 56%). $^1$H NMR (400 MHz, $d^6$-DMSO) δ 8.56 (1H, d, J=7.9 Hz), 8.17–8.04 (2H, m), 7.91 (1H, td, J=7.9, 0.9 Hz), 7.22 (1H, s), 5.71 (2H, s), 5.42 (1H, t, J=5.6 Hz), 4.72 (2H, d, J=5.6 Hz), 4.06 (3H, s), 2.59 (3H, s).

Step 6: 3-(5-Methylisoxazol-3-yl)-6-(1-methyl-5-(piperidin-1-yl)methyl-1H-[1,2,3]triazol-4-ylmethoxy)-[1,2,4]triazolo[3,4-α]phthalazine Thionyl chloride (625 μl, 8.6 mmol) was added to a stirred suspension of [1-methyl-4-({[3-(5-methylisoxazol-3-yl)[1,2,4]triazolo[3,4-α]phthalazine-6-yl]oxy}methyl)-1H-[1,2,3]triazol-5-yl]methanol (672 mg, 1.71 mmol) in $CH_2Cl_2$ (50 ml) and the mixture was stirred at room temperature for 1 h under $N_2$, during which period the solid dissolved and then precipitated. The reaction mixture was concentrated under reduced pressure and then azeotroped with toluene (2×50 ml) and used without further purification. A portion of the crude chloromethyltriazole (125 mg, 0.30 mmol) and piperidine (0.30 ml, 3.0 mmol) in $CH_2Cl_2$ (6ml) were stirred at room temperature for 48 h under $N_2$. The mixture was then concentrated under reduced pressure while dry loading onto silica and purified by column chromatography on silica using 2% $MeOH/CH_2Cl_2$ containing 1% $NH_3$ solution as eluent to yield the desired phthalazine (126 mg, 90%), which was then recrystallised $CH_2Cl_2$/iso-hexanes. $^1$H NMR (360 MHz, $CDCl_3$) δ 8.67 (1H, d, J=8.0 Hz), 8.14 (1H, d, J=8.0 Hz), 7.93 (1H, t, J=8.0 Hz), 7.75 (1H, d, J=8.0 Hz), 6.94 (1H, s), 5.77 (2H, s), 4.12 (3H, broad s), 3.70–3.60 (2H, m), 2.59 (3H, s), 2.40–2.30 (4H, m), 1.75–1.33 (6H, m).

EXAMPLE 15

2-(Azetidin-1-yl)-1-{5-[3-(5-methylisoxazol-3-yl)-[1,2,4]triazolo[3,4-α]phthalazin-6-yloxymethyl]pyridin-2-yl}ethanol Step 1: 5-(Tert-Butyldimethylsilanyloxymethyl)-2-vinylpyridine A solution of 2-bromo-5-(tert-butyldimethylsilyloxymethyl)pyridine (1.0 g, 3.3 mmol) and vinyltributylstannane (2.09 g, 6.6 mmol) in 1,4-dioxane (30 ml) was degassed with a stream of $N_2$ for 15 min and then $Pd(PPh_3)_2Cl_2$ (116 mg, 5 mol %) was added and the reaction mixture heated at reflux under $N_2$ for 20 h. After cooling to room temperature, the solvent were removed under reduced pressure and the mixture was azeotroped with xylene (2×10 ml). The residue was purified by column chromatography on silica using 20% EtOAc/iso-hexanes as eluent to yield the desired vinylpyridine (690 mg, 84%). $^1$H NMR (400 MHz, $CDCl_3$) δ 8.40 (1H, s), 7.51 (1H, d, J=8.0 Hz), 7.21 (1H, d, J=8.0 Hz), 6.71 (1H, dd, J=17.5, 10.8 Hz), 6.06 (1H, d, J=17.5 Hz), 5.34 (1H, d, J=10.8 Hz), 4.64 (2H, s), 0.81 (9H, s), 0.00 (6H, s). m/z ($ES^+$) 250 ($M+H^+$).

Step 2: (6-Vinylpyridin-3-yl)methanol

A solution of tetrabutylammonium fluoride (15.6 mmol) in THF (1.0 M, 15.6 ml) was added to a stirred solution of 5-(tert-butyldimethylsilanyloxymethyl)-2-vinylpyridine (3.55 g, 14.3 mmol) in THF (100 ml) at room temperature under $N_2$ and the reaction mixture was stirred overnight. $NH_4Cl$ solution (40 ml) was added and the organic were extracted with EtOAc (3×70 ml), then washed with brine (50 ml), dried and concentrated under reduced. The mixture was purified by column chromatography on silica using 100% EtOAc as eluent to yield the desired hydroxymethylpyridine (1.59 g, 82%). $^1$H NMR (360 MHz, $CDCl_3$) δ 8.45 (1H, d, J=1.7 Hz), 7.67 (1H, dd, J=7.2, 1.7 Hz), 7.34 (1H, d, J=7.2 Hz), 6.80 (1H, dd, J=17.5, 10.8 Hz), 6.15 (1H, d, J=17.5 Hz), 5.47 (1H, d, J=10.8 Hz), 4.69 (2H, s). m/z ($ES^+$) 135 ($M^+$).

Step 3: 3-(5-Methylisoxazol-3-yl)-6-(6-vinylpyridin-3-ylmethoxy)-[1,2,4]triazolo[3,4-α]phthalazine The reaction was carried out according to Example 1 step 4 using (6-vinylpyridin-3-yl)methanol (500 mg, 3.7 mmol) and 6-chloro-3-(5-methylisoxazol-3-yl)-[1,2,4]triazolo[3,4-α]phthalazine (1.05 g, 3.7 mmol). The crude residue was purified by column chromatography on silica using 2–4% $MeOH/CH_2Cl_2$ to yield the desired phthalazine (1.31 g, 92%). $^1$H NMR (360 MHz, $CDCl_3$) δ 8.86 (1H, s), 8.68 (1H, d, J=8.0 Hz), 8.21 (1H, d, J=8.0 Hz), 8.03 (1H, dd, J=8.0, 2.2 Hz), 7.95 (1H, t, J=8.0 Hz), 7.80 (1H, t, J=8.0 Hz), 7.40 (1H, d, J=8.0 Hz), 6.88–6.78 (2H, m), 6.23 (1H, dd, J=17.5, 1.1 Hz), 5.68 (2H, s), 5.51 (1H, dd, J=10.8, 1.1 Hz), 2.59 (3H, s). m/z ($ES^+$) 385 ($M+2H^+$).

Step 4: 2-(Azetidin-1-yl)-1-{5-[3-(5-methylisoxazol-3-yl)-[1,2,4]triazolo[3,4-α]phthalazin-6-yloxymethyl]pyridin-2-yl}ethanol N-Bromosuccinimide (254 mg, 1.42 mmol) was added to a stirred solution of 3-(5-methylisoxazol-3-yl)-6-(6-vinylpyridin-3-ylmethoxy)-[1,2,4]triazolo[3,4-α]phthalazine (500 mg, 1.30 mmol) in DMF (70 ml), $H_2O$ (10 ml) and AcOH (0.1 ml) and the resulting solution stirred at room temperature for 90 min and then 4 N NaOH (3 ml) was added. The mixture was concentrated under reduced pressure and then taken up in $CH_2Cl_2$ (100 ml), dried and concentrated. The mixture was purified by column chromatography on silica using 2% MeOH/CH₂Cl₂ containing 1% NH₃ as eluent to yield a 1:1 mixture of the vinylpyridine and the epoxide, m/z (ES⁺) 401 (M+H⁺), which was used without further purification. The crude residue was taken up in DMF (5 ml) in a sealed tube and azetidine (126 μl, 1.87 mmol) was added. The reaction was heated at 80° C. for 4 h. The reaction mixture was concentrated under reduced pressure and then taken up in MeOH/CH₂Cl₂, dry loaded onto silica and purified by column chromatography on silica using 8% MeOH/CH₂Cl₂ containing 1% NH₃ as eluent. The fractions containing the correct compound were concentrated under reduced pressure and further purified on a prep. plate eluting with 7% MeOH/CH₂Cl₂ containing 1% NH₃ to yield the desired phthalazine (4.9 mg, 1%). ¹H NMR (400 MHz, CDCl₃) δ 8.82 (1H, s), 8.64 (1H, d, J=7.4 Hz), 8.21 (1H, d, J=7.4 Hz), 8.06 (1H, d, J=7.4 Hz), 7.95 (1H, t, J=7.4 Hz), 7.80 (1H, t, J=7.4 Hz), 7.55 (1H, d, J=7.4 Hz), 6.84 (1H, s), 5.68 (2H, s), 4.68 (1H, dd, J=7.7, 3.5 Hz), 3.38–3.23 (4H, m). 2.87 (1H, dd, J=10.9, 3.5 Hz), 2.70 (1H, dd, J=10.9, 7.7 Hz), 2.60 (3H, s), 2.10 (2H, quintet, J=6.3 Hz). m/z (ES⁺) 457 (M+H⁺).

EXAMPLE 16

N-Methyl-2-{4-[3-(5-methylisoxazol-3-yl)-[1,2,4]triazolo[3,4-α]phthalazin-6-yloxymethyl]-[1,2,3]triazol-1-yl}ethyl)amine Step 1: 6-[1-(2-Bromoethyl)-1H-[1,2,3]triazol-4-ylmethoxy]-3-(5-methylisoxazol-3-yl)-[1,2,4]triazolo[3,4-α]phthalazine A suspension of 2-{4-[3-(5-methylisoxazol-3-yl)-[1,2,4]triazolo[3,4-α]phthalazin-6-yloxymethyl]-[1,2,3]triazol-1-yl}ethanol (300 mg, 0.76 mmol) (from Example 1 Step 5) in CH₂Cl₂ (20 ml) was treated with thionyl bromide (177 μl, 2.28 mmol) at room temperature under N₂ and the mixture was stirred at room temperature for 3 h. The reaction mixture was concentrated under reduced pressure, then taken up in MeOH/CH₂Cl₂ and dry loaded onto silica. Column chromatography on silica using 2% MeOH/CH₂Cl₂ containing 1% NH₃ as eluent yielded the desired bromide (200 mg, 58%). ¹H NMR (360 MHz, d⁶-DMSO) δ 8.56 (1H, d, J=8.0 Hz), 8.54 (1H, s), 8.19 (1H, d, J=9.0 Hz), 8.10 (1H, t, J=8.0 Hz), 7.94 (1H, t, J=8.0 Hz), 7.18 (1H, s), 5.73 (2H, s), 4.83 (2H, t, J=5.8 Hz), 3.94 (2H, t, J=5.8 Hz), 2.59 (3H, s). m/z (ES⁺) 455, 457 (1:1, M+H⁺).

Step 2: N-Methyl-2-{4-[3-(5-methylisoxazol-3-yl)-[1,2,4]triazolo[3,4-α]phthalazin-6-yloxymethyl]-[1,2,3]triazol-1-yl}ethyl)amine A solution of 6-[1-(2-bromoethyl)-1H-[1,2,3]triazol-4-ylmethoxy]-3-(5-methylisoxazol-3-yl)-[1,2,4]triazolo[3,4-α]phthalazine (90 mg, 0.20 mmol), ethanol (2 ml) and methylamine (2.0 M in THF, 7.5 ml, 15 mmol) were heated at 90° C. for 4 h in a sealed tube. The reaction solvent was removed in vacuo, water added and extracted into dichloromethane. These extracts were washed with water and saturated brine then dried over magnesium sulphate, filtered and concentrated in vacuo. The resultant solid was purified by preparative thin layer chromatography on silica eluting with 5% methanol-dichloromethane containing 1% NH₃ to give methyl-(2-{4-[3-(5-methylisoxazol-3-yl)-[1,2,4]triazolo[3,4-α]phthalazin-6-yloxymethyl]-[1,2,3]triazol-1-yl}ethyl)amine as a White solid (32 mg). ₁H NMR (400 MHz, d₆-DMSO) δ 2.25 (3H, s), 2.59 (3H, s), 2.91 (2H, t, J6), 4.43 (2H, t, J 6), 5.70 (2H, s), 7.18 (1H, s), 7.94 (1H, t, J 7), 8.10 (1H, t, J 7), 8.19 (1H, d, J 8), 8.46 (1H, s), 8.56 (1H, d, J 8). m/z (ES⁺) 406 (M+H⁺).

EXAMPLE 17

Tert-Butyl[3-(5-methylisoxazol-3-yl)-[1,2,4]triazolo[3,4-α]phthalazin-6-yloxymethyl]pyridazin-3-ylmethyl}amine Step 1: {6-[3-(5-Methylisoxazol-3-yl)-[1,2,4]triazolo[3,4-α]phthalazin-6-yloxymethyl]-pyridazin-3-yl}methanol.

(6-Hydroxymethylpyridazin-3-yl)methanol (J. Het. Chem., 1996, 33 (6), 2059–2061) (0.10 g, 0.71 mmol) and 6-chloro-3-(5-methylisoxazol-3-yl)-[1,2,4]triazolo[3,4-α]phthalazine (0.22 g, 0.77 mmol) were coupled together and purified as in Example 1, step 4 to give {6-[3-(5-methylisoxazol-3-yl)-[1,2,4]triazolo[3,4-α]phthalazin-6-yloxymethyl]pyridazin-3-yl}methanol as a white solid (35 mg). ¹H NMR (400 MHz, d₆-DMSO) δ 2.58 (3H, s), 4.80 (2H, s), 5.65–5.75 (1H, br s), 5.92 (2H, s), 6.99 (1H, s), 7.81 (1H, d, J 8), 7.98 (1H, t, J 8), 8.07–8.15 (2H, m), 8.32 (1H, d, J 8), 8.58 (1H, d, J 8). m/z (ES⁺) 390 (M+H⁺).

Step 2: tert-Butyl-{6-[3-(5-methylisoxazol-3-yl)-[1,2,4]triazolo[3,4-α]phthalazin-6-yloxymethyl]-pyridazin-3-ylmethyl}amine Methane sulfonyl chloride (60 μl, 0.77 mmol) was added to a stirred suspension of {6-[3-(5-methylisoxazol-3-yl)-[1,2,4]triazolo[3,4-α]phthalazin-6-yloxymethyl]pyridazin-3-yl}methanol (30 mg, 77 μmol) in dry dichloromethane (7 ml) and triethylamine (0.12 ml, 0.87 mmol) at ambient temperature. After 2 h the mixture was applied directly to a pad of silica and eluted with 5% methanol-dichloromethane to give the mesylate as a white solid (35 mg). This material, triethylamine (50 μl, 0.40 mmol) and tert-butylamine (0.20 ml, 1.9 mmol) in tetrahydrofuran (5 ml)-ethanol (1 ml) was stirred in a sealed tube and heated to 70° C. After 2 h the solution was allowed to cool, solvents removed in vacuo and purification by column chromatography, eluting with dichloromethane on a gradient of methanol (5–10%) containing 1% ammonia, gave tert-butyl{6-[3-(5-methylisoxazol-3-yl)-[1,2,4]triazolo[3,4-α]phthalazin-6-yloxymethyl]pyridazin-3-ylmethyl}amine as a white solid (15 mg). 1H NMR (400 MHz, d₆-DMSO) δ 1.10 (9H, s), 2.59 (3H, s), 4.04 (2H, s), 5.91 (2H, s), 6.99 (1H, s), 7.83 (1H, d, J 8), 8.00 (1H, t, J 8), 8.03 (1H, d, J 8), 8.12 (1H, t, J 8), 8.31 (1H, d, J 8), 8.58 (1H, d, J 8). m/z (ES⁺) 445 (M+H⁺).

EXAMPLE 18

{2-[5-(3-Isoxazol-3-yl-[1,2,4]triazolo[3,4-α]phthalazin-6-yloxymethyl)-[1,2,4]triazol-1-yl]ethyl}dimethylamine The reaction was carried out using the procedure described in Example 1, Step 4, using 3-isoxazol-3-yl-6-(2,2,2-trifluoroethoxy)-[1,2,4]triazolo[3,4-α]phthalazine (WO-A-9850385) (100 mg, 0.29 mmol) instead of 6-chloro-3-(5-methylisoxazol-3-yl)-[1,2,4]triazolo[3,4-α]phthalazine with [2-(2-dimethylaminoethyl)-2H-[1,2,4]triazol-3-yl]methanol (Example 4, Step 2) (51 mg, 0.29 mmol). Crude residue was purified on silica eluting 2–6% MeOH/DCM, followed by crashing out from DCM using isohexane. The title compound was isolated by filtration to give a cream solid (47 mg, 39%).

¹H NMR (360 MHz, d₆DMSO) δ 2.13 (6H, s), 2.63–2.71 (2H, m), 4.40 (2H, t, J=6.3 Hz), 5.84 (2H, s), 7.56 (1H, d, J=1.7 Hz), 7.97 (1H, t, J=8.0 Hz), 8.03 (1H, s), 8.12 (1H, t, J=8.1 Hz), 8.22 (1H, d, J=7.9 Hz), 8.60 (1H, d, J=7.5 Hz). MS (ES⁺) 406 (M+1).

EXAMPLE 19

Dimethyl[2-{5-[3-(3-methyl[1,2,4]oxadiazol-5-yl)-[1,2,4]triazolo[3,4-α]phthalazin-6-yloxymethyl]-[1,2,4]triazol-1-yl}ethyl)amine The reaction was carried out using the procedure described in Example 1, Step 4 using 6-chloro-3-(3-methyl[1,2,4]oxadiazol-5-yl)-[1,2,4]triazolo[3,4-α]phthalazine (WO-A-9850385) (125 mg, 0.44 mmol) and [2-(2-dimethylaminoethyl)-2H-[1,2,4]triazol-3-yl]methanol (Example 4, Step 2) (74 mg, 0.44 mmol). Crude residue was purified on silica, eluting product with 3% MeOH/DCM, followed by trituration with DCM and isohexane. The title compound was isolated by filtration to give a white solid (50 mg, 27%).

$^1$H NMR (360 MHz, d$_6$DMSO) δ 2.15 (6H, S), 2.55 (3H, s), 2.63–2.71 (2H, m), 4.44 (2H, t, J=6.2 Hz), 5.84 (2H, s), 7.99–8.06 (2H, m), 8.16 (1H, t, J=7.6 Hz), 8.26 (1H, d, J=7.9 Hz), 8.64 (1H, d, J=7.8 Hz). MS (ES$^+$) 421 (M+1).

EXAMPLE 20

Dimethyl{1-methyl-5-[3-(5-methylisoxazol-3-yl)-[1,2,4]triazolo[3,4-α]phthalazin-6-yloxymethyl]-1H-[1,2,4]triazol-3-ylmethyl}amine Step 1: [1-Methyl-5-({[3-(5-methylisoxazol-3-yl)-[1,2,4]triazolo[3,4-α]phthalazin-6-yl]oxy}methyl]-1H-[1,2,4]triazol-3-yl}methanol 6-Chloro-3-(5-methylisoxazol-3-yl)-1,2,4-triazolo[3,4-α]phthalazine (Intermediate 1) (2.33 g, 8.2 mmol) was reacted with [3-({[(1,1-dimethylethyl)(dimethyl)silyl]oxy}methyl)-1-methyl-1H-[1,2,4]triazol-5-yl]methanol (WO-A-0047582) (2.1 g, 8.2 mmol) as described in Example 1, Step 4, to give 6-({[3-({[(1,1-dimethylethyl)(dimethyl)silyl]oxy}methyl)-1-methyl-1H-1,2,4-triazol-6-yl]methyl}oxy)-3-(5-methylisoxazol-3-yl)-[1,2,4]triazolo[3,4-α]phthalazine as a white solid (2.3 g, 56%). MS (ES$^+$) 507 (M+1). The foregoing silyl ether was deprotected as described in Example 3, Step 5, to give the title compound as a white solid in 56% yield.

$^1$H NMR (360 MHz, d$_6$DMSO) δ 2.60 (3H, d, J=0.6 Hz), 3.96 (3H, s), 4.42 (2H, d, J=5.9 Hz), 5.24 (1H, t, J=5.9 Hz), 5.78 (2H, s), 7.23 (1H, d, J=0.9 Hz), 7.95 (1H, t, J=8.4 Hz), 8.11 (1H, t, J=8.1 Hz), 8.24 (1H, d, J=7.9 Hz), 8.57 (1H, d, J=7.8 Hz). MS (ES$^+$) 393 (M+1).

Step 2: 6-({[3-Chloromethyl-1-methyl-1H-[1,2,4]triazol-5-ylmethyl}oxy)-3-(5-methylisoxazol-3-yl)-[1,2,4]triazolo[3,4-α]phthalazine A suspension of [1-methyl-5-({[3-(5-methylisoxazol-3-yl)-[1,2,4]triazolo[3,4-α]phthalazin-6-yl]oxy}methyl)-1H-[1,2,4]triazol-3-yl}methanol (350 mg, 0.9 mmol) in dichloromethane (15 ml) was treated portionwise with thionyl chloride (5 ml) at room temperature for 1 h. The mixture was evaporated in vacuo and the residue partitioned between 5% MeOH/DCM and water. The aqueous layer was basified with saturated K$_2$CO$_3$ solution. The organic layer was separated, dried (MgSO$_4$), and concentrated to give the title compound as a white solid (0.28 g, 78%).

$^1$H NMR (400 MHz, CDCl$_3$) δ 2.58 (3H, s), 4.10 (3H, s), 4.61 (2H, s), 5.82 (2H, s), 6.88 (1H, s), 7.85 (1H, t, J=8.3 Hz), 7.99 (1H, t, J=8.2 Hz), 8.24 (1H, d, J=8.0 Hz), 8.72 (1H, d, J=7.8 Hz). MS (ES$^+$) 411 & 413 (ratio 1.5:1) (M+1).

Step 3: Dimethyl{1-methyl-5-[3-(5-methylisoxazol-3-yl)-[1,2,4]triazolo[3,4-α]phthalazin-6-yloxymethyl]-1H-[1,2,4]triazol-3-ylmethyl}amine A suspension of the foregoing chloride (110 mg. 0.27 mmol) in dichloromethane (10 ml) was treated with a 2.0 M solution of dimethylamine in THF (1.35 ml, 2.7 mmol) for 16 h at room temperature then for a further 2 h at 50° C. The reaction was concentrated in vacuo and the residue purified by silica plug chromatography eluting 1% MeOH/DCM then 6% MeOH/DCM. The title compound was obtained as an off-white solid (55 mg, 49%).

$^1$H NMR (400 MHz, d$_6$DMSO) δ 2.24 (6H, s), 2.60 (3H, d, J=0.6 Hz), 3.53 (2H, s), 3.97 (3H, s), 5.79 (2H, s), 7.24 (1H, d, J=0.9 Hz), 7.95 (1H, t, J=8.3 Hz), 8.11 (1H, t, J=8.0 Hz), 8.25 (1H, d, J=7.8 Hz), 8.57 (1H, d, J=7.7 Hz). MS (ES$^+$) 420 (M+1).

EXAMPLE 21

N-Ethyl-1-[1-methyl-5-({[3-(5-methylisoxazol-3-yl)[1,2,4]triazolo[3,4-α]phthalazin-6-yl]oxy}methyl)-1H-[1,2,4]triazol-3-ylethyl]amine Step 1: 1-Methyl-5-({[3-(5-methylisoxazol-3-yl) [1,2,4]triazolo[3,4-α]phthalazin-6-yl]oxy}methyl)-1H-[1,2,4]triazole-3-carbaldehyde A mixture of [1-methyl-5-({[3-(5-methylisoxazol-3-yl)-[1,2,4]triazolo[3,4-α]phthalazin-6-yl]oxy}methyl]-1H-[1,2,4]triazol-3-yl}methanol (Example 20) (1 g, 2.55 mmol) in chloroform (120 ml) and manganese dioxide (4.4 g, 51 mmol) was heated at reflux for 60 h. More manganese dioxide (2.2 g, 25 mmol) was added and reflux continued for further 24 h. The cooled mixture was filtered through "Hyflo" eluting with chloroform. Solvent was evaporated in vacuo to give the crude carbaldehyde as a yellow solid (320 mg). MS (ES$^+$) 391 (M+1).

Step 2: 1-{1-Methyl-5-({[3-(5-methylisoxazol-3-yl)[1,2,4]triazolo[3,4-α]phthalazin-6-yl]oxy}methyl)-1H-[1,2,4]triazol-3-yl}ethanol A cooled (ice/water bath) solution of the foregoing aldehyde (320 mg, 0.82 mmol) in dichloromethane (60 ml) was treated with a 3 M solution of methyl magnesium chloride in THF (0.33 ml, 0.99 mmol). The cooling bath was removed and stirred at room temperature for 24 h. A solution of ammonium chloride was added and the dichloromethane layer separated. Aqueous re-extracted twice with dichloromethane. Combined organics dried (MgSO$_4$) and evaporated in vacuo to give crude which was purified by silica chromatography eluting dichloromethane then 2% MeOH/DCM to give the alcohol as a white solid (180 mg, 54%). MS (ES$^+$) 407 (M+1).

Step 3: 1-{1-Methyl-5-({[3-(5-methylisoxazol-3-yl)[1,2,4]triazolo[3,4-α]phthalazin-6-yl]oxy}methyl)-1H-[1,2,4]triazol-3-yl}ethanone The foregoing secondary alcohol was oxidized using manganese dioxide by the procedure described above to give the ketone (160 mg, 89%). MS (ES$^+$) 405 (M+1).

Step 4: N-Ethyl-1-[1-methyl-5-({[3-(5-methylisoxazol-3-yl) [1,2,4]triazolo[3,4-α]phthalazin-6-yl]oxy}methyl)-1H-[1,2,4]triazol-3-ylethyl]amine The title compound (6 mg, 8%) was obtained by reductive amination of the foregoing ketone by the procedure of Example 2, Step 2 except the reaction was heated in a sealed tube at 50° C. (oil bath) instead of room temperature.

$^1$H NMR (400 MHz, d$_6$DMSO) δ 0.96 (3H, t, J=7.1 Hz), 1.37 (3H, d, J=6.8 Hz), 2.53–2.61 (5H, m), 3.97–4.05 (4H, m), 5.80 (2H, s), 7.22 (1H, s), 7.96 (1H, t, J=8.2 Hz), 8.12 (1H, t, J=7.8 Hz), 8.25 (1H, d, J=7.8 Hz), 8.58 (1H, d, J=7.8 Hz). MS (ES$^+$) 434 (M+1).

The followings compounds can be made by analogy with the foregoing Examples:

TABLE 1

| Example No. | X |
|---|---|
| 22 | 5-methyl-pyridin-2-yl-methyl-azetidine |
| 23 | 6-methyl-pyridin-3-yl-methyl-azetidine |
| 24 | 5-methyl-pyridin-2-yl-ethyl-azetidine |
| 25 | 6-methyl-pyridin-2-yl-ethyl-imidazole |
| 26 | 6-methyl-pyridin-2-yl-ethyl-azetidine |

TABLE 1-continued

| Example No. | X |
|---|---|
| 27 | 3-methylphenyl-N(Me)-propyl-NMe₂ |
| 28 | 6-methyl-pyridin-2-yl-methyl-piperazine |
| 29 | 6-methyl-pyridin-2-yl-methyl-NHMe |
| 30 | 6-methyl-pyridin-2-yl-methyl-piperidine |
| 31 | 6-methyl-pyridin-2-yl-methyl-NHBn |

TABLE 1-continued
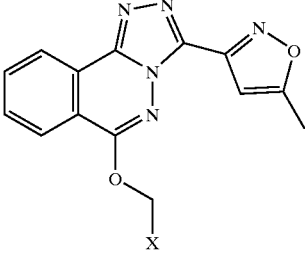
| Example No. | X |
|---|---|
| 32 | 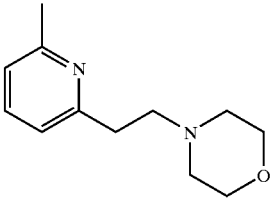 |
| 33 | 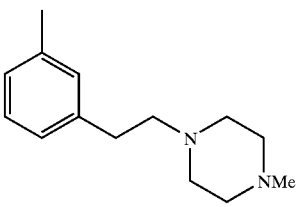 |
| 34 | 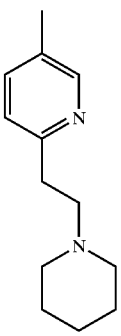 |
| 35 | 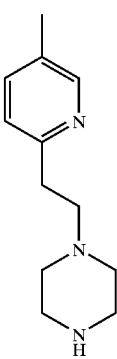 |
TABLE 1-continued
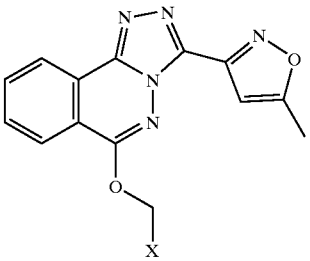
| Example No. | X |
|---|---|
| 36 | 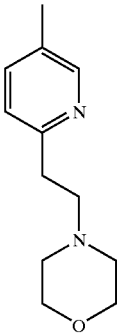 |
| 37 | 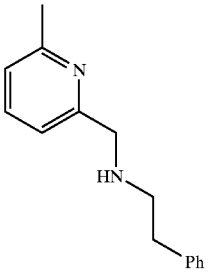 |
| 38 | 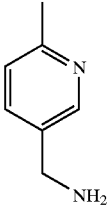 |
| 39 | 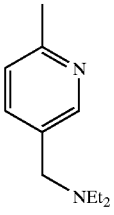 |

TABLE 1-continued
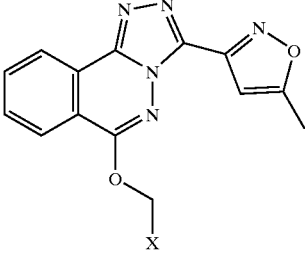
| Example No. | X |
|---|---|
| 40 | 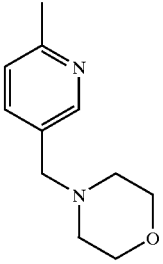 |
| 41 | 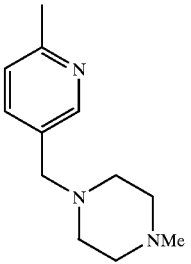 |
| 42 | 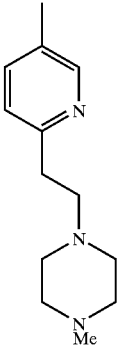 |
| 43 | 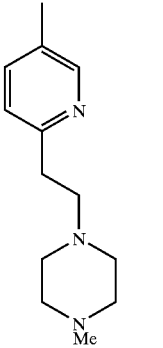 |
TABLE 1-continued
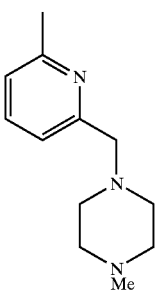
| Example No. | X |
|---|---|
| 44 | 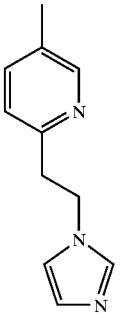 |
| 45 | 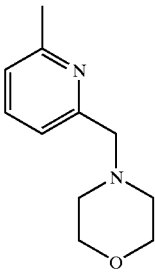 |
| 46 | 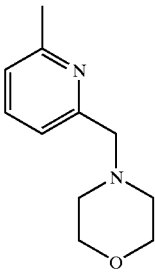 |
| 47 | 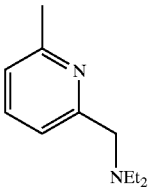 |
| 48 | 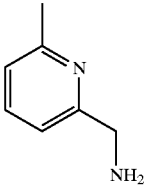 |

TABLE 1-continued

[Structure: phthalazine fused with triazole, bearing 5-methylisoxazol-3-yl and OCH₂–X substituent]

| Example No. | X |
|---|---|
| 49 | 6-methylpyridin-3-yl-CH₂–piperazin-1-yl (NH) |
| 50 | 6-methylpyridin-3-yl-CH₂–imidazol-1-yl |
| 51 | 5-methylpyridin-2-yl-CH₂–morpholin-4-yl |
| 52 | 5-methylpyridin-2-yl-CH₂–(4-methylpiperazin-1-yl) |
| 53 | 5-methylpyridin-2-yl-CH₂–NMe₂ |
| 54 | 6-methylpyridin-2-yl-CH₂–NMe₂ |
| 55 | 6-methylpyridin-2-yl-CH₂–imidazol-1-yl |
| 56 | 3-methylphenyl-CH₂–NH–(CH₂)₃–NMe₂ |
| 57 | 6-methylpyridin-2-yl–(4-methylpiperazin-1-yl) |

TABLE 1-continued
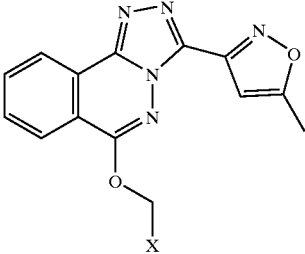
| Example No. | X |
|---|---|
| 58 | 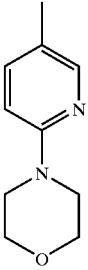 |
| 59 | 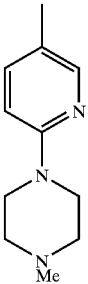 |
| 60 | 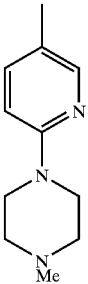 |
| 61 | 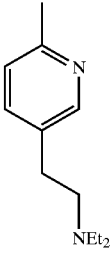 |
| 62 | 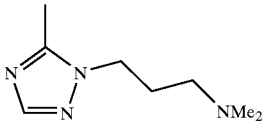 |
TABLE 1-continued
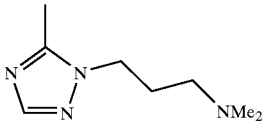
| Example No. | X |
|---|---|
| 63 | 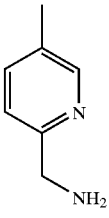 |
| 64 | 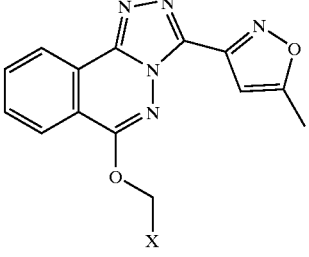 |
| 65 | 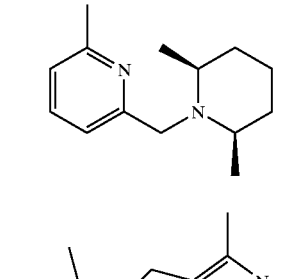 |
| 66 | 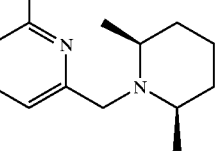 |
| 67 | 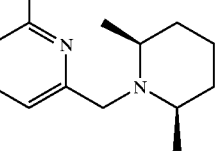 |
| 68 | 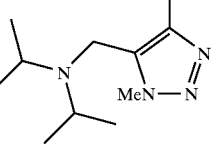 |

TABLE 1-continued

| Example No. | X |
|---|---|
| 69 | 6-methylpyridin-3-yl-CH2-N(CH2CH(CH3)2)2 |
| 70 | 6-methylpyridin-3-yl-CH2-N(iPr)2 |
| 71 | 6-methylpyridin-3-yl-CH2-N(2,6-dimethylpiperidin-1-yl) |
| 72 | 6-methylpyridin-3-yl-CH2-N(cyclohexyl)2 |
| 73 | (5-methyl-4-Me-1,2,4-triazol-3-yl)-CH2-N(2,6-dimethylpiperidin-1-yl) |
| 74 | (5-methyl-1-Me-1,2,4-triazol-3-yl)-CH2-N(iPr)2 |
| 75 | (5-methyl-1,2,4-triazol-1-yl)-CH2CH2-NH2 |
| 76 | 6-methylpyridin-3-yl-CH2-N(tBu)(Et) |
| 77 | (5-methyl-1,2,3-triazol-1-yl)-CH2CH2-NHMe |

TABLE 1-continued
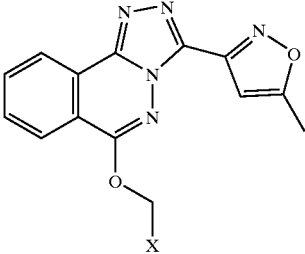
| Example No. | X |
|---|---|
| 78 | 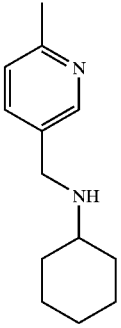 |
| 79 | 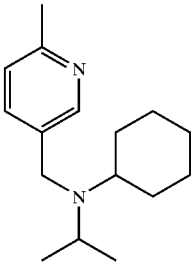 |
| 80 | 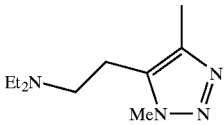 |
| 81 | 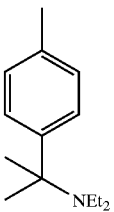 |
| 82 | 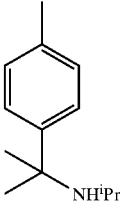 |
TABLE 1-continued
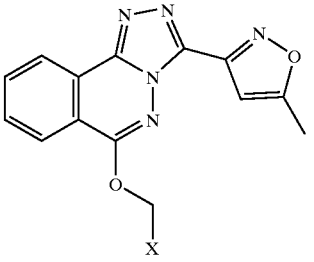
| Example No. | X |
|---|---|
| 83 | 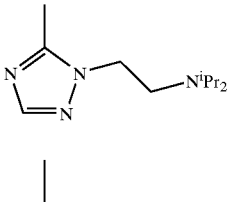 |
| 84 | 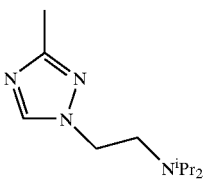 |
| 85 | 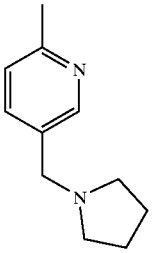 |
| 86 | 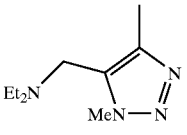 |
| 87 | 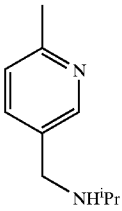 |
| 88 | 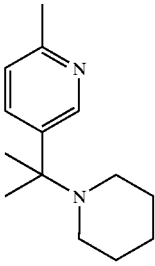 |

TABLE 1-continued
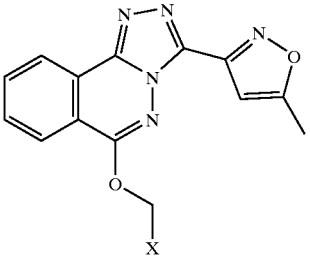
| Example No. | X |
|---|---|
| 89 | 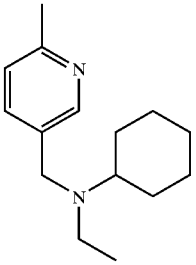 |
| 90 | 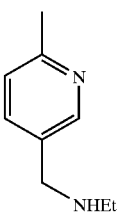 |
| 91 | 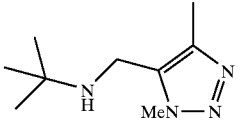 |
| 92 | 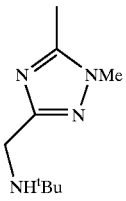 |
| 93 | 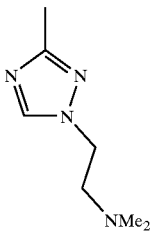 |
TABLE 1-continued
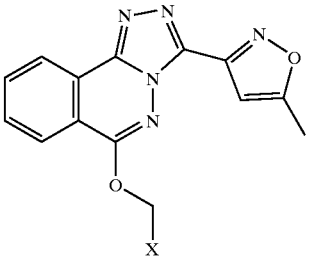
| Example No. | X |
|---|---|
| 94 | 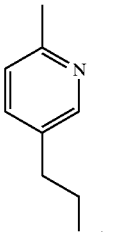 |
| 95 | 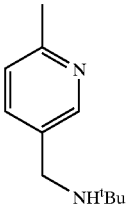 |
| 96 | 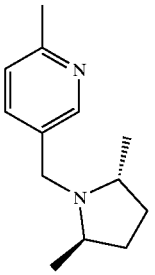 |
| 97 | 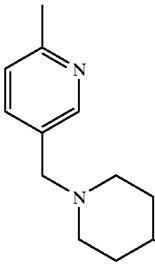 |
| 98 | 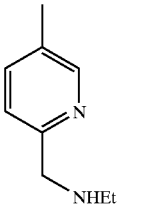 |

TABLE 1-continued
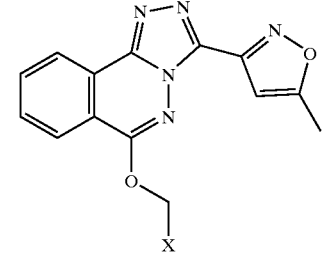
| Example No. | X |
|---|---|
| 99 | 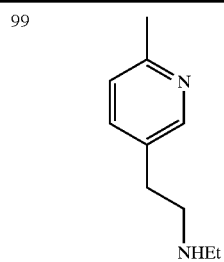 |
| 100 | 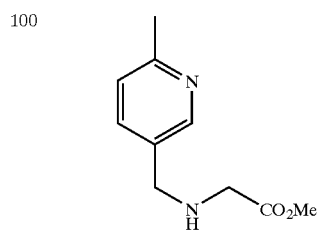 |
| 101 | 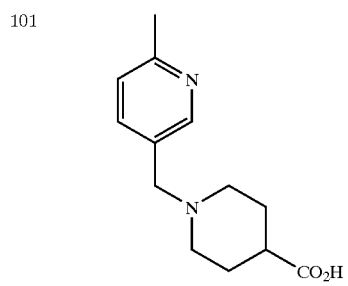 |
| 102 | 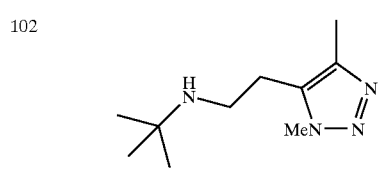 |
| 103 | 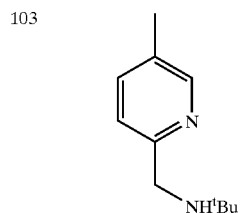 |
TABLE 1-continued
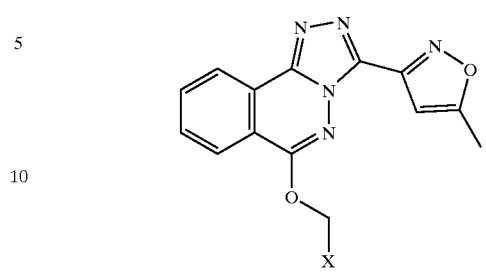
| Example No. | X |
|---|---|
| 104 | 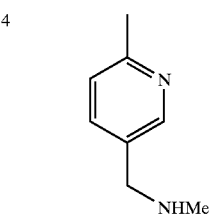 |
| 105 | 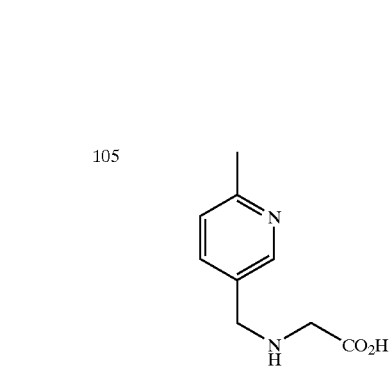 |
| 106 | 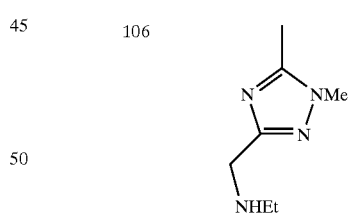 |
| 107 | 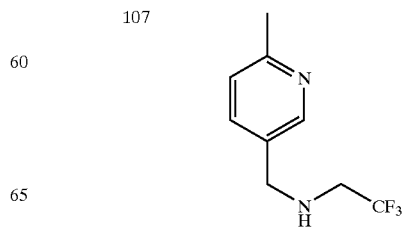 |

TABLE 1-continued

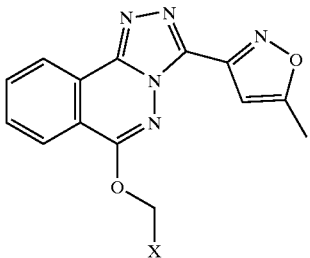

Example No.    X

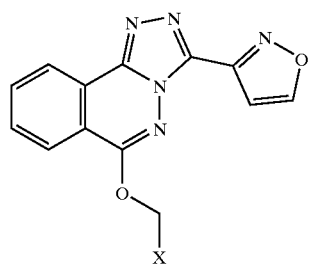

X =

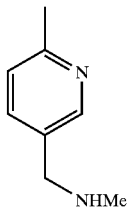   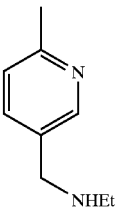

Example 108    Example 109

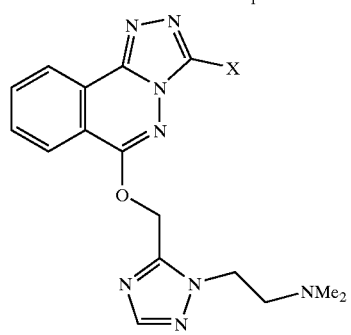

Example 110

X =

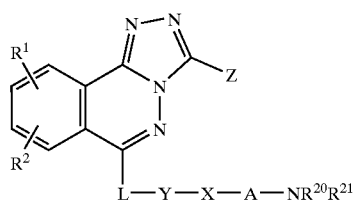

What is claimed is:

1. A compound of the formula I:

(I)

wherein:

A is a $C_{1-4}$alkylidene group optionally substituted with one or more $C_{1-4}$alkyl, halogen or hydroxy groups in which case $R^{20}$ and $R^{21}$ are independently chosen from hydrogen, $C_{1-10}$alkyl, $C_{3-6}$cycloalkyl, $C_{5-6}$cycloalkenyl, $C_{2-10}$alkenyl, $C_{2-10}$alkynyl, amino$C_{1-10}$alkyl, $C_{1-6}$alkylamino$C_{1-10}$alkyl, di($C_{1-6}$alkyl)amino$C_{1-10}$alkyl and phenyl$C_{1-10}$alkyl, or $R^{20}$ and $R^{21}$, together with the nitrogen atom to which they are attached, form an unsaturated 4–7 membered heterocyclic ring optionally containing a further nitrogen atom or an oxygen atom, or a 5 or 6 membered heteroaromatic ring containing one, two or three further heteroatoms chosen from O, N and S, at most one of the heteroatoms being O or S, may be substituted with one or two groups chosen from halogen, hydroxy, $C_{1-6}$alkyl, $CF_3$, CN, amino and nitro or $R^{20}$ and/or $R^{21}$, together with A and the nitrogen to which $R^{20}$ and/or $R^{21}$ is attached, form a 4–7 membered heterocyclic ring optionally containing a further nitrogen or oxygen atom, $R^{20}$ and $R^{21}$ being optionally substituted with one, two or three groups chosen from halogen, hydroxy, $C_{1-6}$alkyl, $CF_3$, CN, amino, C(O)H, carboxy and $CO_2C_{1-6}$ alkyl;

alternatively A is a bond in which case $R^{20}$ and $R^{21}$, together with the nitrogen atom to which they are attached, form a 4–7 membered saturated heterocyclic ring containing a further nitrogen or oxygen atom, or a partially saturated heterocyclic ring optionally containing a further nitrogen or oxygen atom, $R^{20}$ and $R^{21}$ being optionally substituted with one, two or three groups chosen from halogen, hydroxy, $C_{1-6}$alkyl, $CF_3$, CN, amino, nitro, C(O)H, carboxy and $CO_2C_{1-6}$alkyl;

$R^1$ is hydrogen, halogen or CN or a group $CF_3$, $OCF_3$, $C_{1-4}$alkyl, $C_{2-4}$alkenyl, $C_{2-4}$alkynyl, $C_{1-4}$alkoxy, $C_{2-4}$alkenyloxy or $C_{2-4}$alkynyloxy, each of which groups is unsubstituted or substituted with one or two halogen atoms or with a pyridyl or phenyl ring each of which rings may be unsubstituted or independently substituted by one or two halogen atoms or nitro, cyano, amino, methyl or $CF_3$ groups;

$R^2$ is hydrogen, halogen or CN or a group $CF_3$, $OCF_3$, $C_{1-4}$alkyl, $C_{2-4}$alkenyl, $C_{2-4}$alkynyl, $C_{1-4}$alkoxy, $C_{2-4}$alkenyloxy or $C_{2-4}$alkynyloxy each of which groups is unsubstituted or substituted with one or two halogen atoms;

L is O, S or $NR''$ where $R''$ is H, $C_{1-6}$alkyl or $C_{3-6}$cycloalkyl;

X is a 5-membered heteroaromatic ring containing 1, 2, 3 or 4 heteroatoms independently chosen from oxygen, nitrogen and sulphur, at most one of the heteroatoms being oxygen or sulphur, or a 6-membered heteroaromatic ring containing 1, 2 or 3 nitrogen atoms, the 5- or 6-membered heteroaromatic ring being optionally fused to a benzene ring and the heteroaromatic ring being optionally substituted by $R^x$ and/or $R^y$ and/or $R^z$, where $R^x$ is halogen, $R^3$, $OR^3$, $OCOR^3$, $NR^4R^5$, $NR^4COR^5$, tri($C_{1-6}$alkyl)silyl$C_{1-6}$alkoxy$C_{1-4}$alkyl, CN or $R^9$, $R^y$ is halogen, $R^3$, $OR^3$, $OCOR^3$, $NR^4R^5$, $NR^4COR^5$ or CN and $R^z$ is $R^3$, $OR^3$ or $OCOR^3$, where $R^3$ is $C_{1-6}$alkyl, $C_{2-6}$alkenyl, $C_{2-6}$alkynyl, $C_{3-6}$cycloalkyl, hydroxy$C_{1-6}$alkyl and $R^3$ is optionally mono-, di- or tri-fluorinated, $R^4$ and $R^5$ are each independently hydrogen, $C_{1-6}$alkyl, $C_{2-6}$alkenyl, $C_{2-6}$alkynyl, $C_{3-6}$cycloalkyl or $CF_3$ or $R^4$ and $R^5$, together with the nitrogen atom to which they are attached, form a 4–7 membered heteroaliphatic ring containing the nitrogen atom as the sole heteroatom, and $R^9$ is benzyl or an aromatic ring containing either 6 atoms, 1, 2 or 3 of which are optionally nitrogen, or 5 atoms, 1, 2 or 3 of which are independently chosen from oxygen, nitrogen and sulphur, at most one of the atoms being oxygen or sulphur, and R⁹ is optionally substituted by one, two or three substituents independently chosen from halogen atoms and $C_{1-4}$alkyl, $C_{2-4}$alkenyl, $C_{2-4}$alkynyl, $C_{1-4}$alkoxy, $C_{2-4}$alkenyloxy and $C_{2-4}$alkynyloxy groups each of which groups is unsubstituted or substituted by one, two or three halogen atoms, and when X is a pyridine derivative, the pyridine derivative is optionally in the form of the N-oxide and providing that when X is a tetrazole derivative it is protected by a $C_{1-4}$alkyl group; or X is phenyl optionally substituted by one, two or three groups independently selected from halogen, cyano, $C_{1-6}$alkyl, $C_{2-6}$alkenyl, $C_{2-6}$alkynyl and $C_{3-6}$cycloalkyl;

Y is optionally branched $C_{1-4}$alkylidene optionally substituted by an oxo group or Y is a group $(CH_2)_j O$ wherein the oxygen atom is nearest the group X and j is 2, 3 or 4;

Z is a 5-membered heteroaromatic ring containing 1, 2 or 3 heteroatoms independently selected from oxygen, nitrogen and sulphur, at most one of the heteroatoms being oxygen or sulphur and providing that when one of the atoms is oxygen or sulphur then at least one nitrogen atom is present, or a 6-membered heteroaromatic ring containing 2 or 3 nitrogen atoms, Z being optionally substituted by $R^v$ and/or $R^w$, where $R^v$ is halogen, $R^6$, $NR^7R^8$, $NR^7COR^8$, CN, furyl, thienyl, phenyl, benzyl, pyridyl or a 5-membered heteroaromatic ring containing at least one nitrogen atom and optionally 1, 2 or 3 other heteroatoms independently selected from oxygen, nitrogen and sulphur, at most one of the other heteroatoms being oxygen or sulphur and $R^w$ is $R^6$ or CN;

$R^6$ is $C_{1-6}$alkyl, $C_{2-6}$alkenyl, $C_{2-6}$alkynyl, $C_{3-6}$cycloalkyl, hydroxy$C_{1-6}$alkyl, $C_{1-6}$alkoxy, $C_{2-6}$alkenyloxy, $C_{2-6}$alkynyloxy, $C_{1-6}$alkoxy$C_{1-6}$alkyl, $CH_2F$ or $CF_3$; and $R^7$ and $R^8$ are each independently hydrogen, $C_{1-6}$alkyl, $C_{2-6}$alkenyl, $C_{2-6}$alkynyl, $C_{3-6}$cycloalkyl or $CF_3$ or $R^7$ and $R^8$, together with the nitrogen atom to which they are attached, form a 4–7 membered heteroaliphatic ring containing the nitrogen atom as the sole heteroatom; or a pharmaceutically acceptable salt thereof.

2. The compound of claim 1 of formula I':

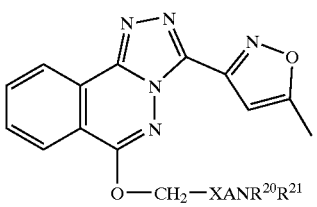

(I')

wherein A, X, $R^{20}$ and $R^{21}$ are as defined in claim 1.

3. The compound of claim 1 which is selected from the group consisting of:

dimethyl{6-[3-(5-methylisoxazol-3-yl)-[1,2,4]triazolo[3,4-α]phthalazin-6-yloxymethyl]pyridin-3-ylmethyl}amine;
dimethyl[2-{5-[3-(5-methylisoxazol-3-yl)-[1,2,4]triazolo[3,4-α]phthalazin-6-yloxymethyl]-[1,2,4]triazol-1-yl}ethyl]amine;
1-methyl-1-{2-[3-(5-methylisoxazol-3-yl)-[1,2,4]triazolo[3,4-α]phthalazin-6-yloxymethyl]pyridin-5-yl}ethylamine;
dimethyl-(1-methyl-1-{2-[3-(5-methyl-isoxazol-3-yl)-{1,2,4]triazolo[3,4-α]phthalazin-6-yloxymethyl]pyridin-5-yl}ethyl)amine;
3-(5-methylisoxazol-3-yl)-6-[5-(1-methylpyrrolidin-2-yl)pyridin-2-ylmethoxy]-[1,2,4]triazolo[3,4-α]phthalazine;
N,N-dimethyl-2-[5-({[3-(5-methylisoxazol-3-yl)[1,2,4]triazolo[3,4-α]phthalazin-6-yl]oxy}methyl)-1H-[1,2,3]triazol-1-yl]ethylamine;
dimethyl-(2-{4-[3-(5-methylisoxazol-3-yl)-[1,2,4]triazolo[3,4-α]phthalazin-6-yloxymethyl]-[1,2,3]triazol-1-yl}ethyl)amine;
3-(5-methylisoxazol-3-yl)-6-(6-[morpholin-4-yl]pyridin-2-ylmethoxy)[1,2,4]triazolo-[3,4-α]phthalazine;
6-[5-(2-(azetidin-1-yl)ethyl)-1-methyl-1H-[1,2,3]triazol-4-ylmethoxy]-3-(5-methyl-isoxazol-3-yl)-[1,2,4]triazolo[3,4-α]phthalazine;
4-[5-({[3-(5-methylisoxazol-3-yl)[1,2,4]triazolo[3,4-α]phthalazin-6-yl]oxy}methyl)pyridin-2-yl]piperidin-4-ol;
3-(5-methylisoxazol-3-yl)-6-(1',2',3',6'-tetrahydro-[2,4']bipyridinyl-5-ylmethoxy)-[1,2,4]triazolo[3,4-α]phthalazine;
3-(5-methylisoxazol-3-yl)-6-(1-methyl-5-(piperidin-1-yl)methyl-1H-[1,2,3]triazol-4-ylmethoxy)-[1,2,4]triazolo[3,4-α]phthalazine;
2-(azetidin-1-yl)-1-{5-[3-(5-methylisoxazol-3-yl)-[1,2,4]triazolo[3,4-α]phthalazin-6-yloxymethyl]pyridin-2-yl}ethanol;
N-methyl-2-{4-[3-(5-methylisoxazol-3-yl)-[1,2,4]triazolo[3,4-α]phthalazin-6-yloxymethyl]-[1,2,3]triazol-1-yl}ethyl)amine;
tert-butyl[3-(5-methylisoxazol-3-yl)-[1,2,4]triazolo[3,4-α]phthalazin-6-yloxymethyl]pyridazin-3-ylmethyl}amine;
{2-[5-(3-isoxazol-3-yl-[1,2,4]triazolo[3,4-α]phthalazin-6-yloxymethyl)-[1,2,4]triazol-1-yl]ethyl}dimethylamine;
dimethyl[2-{5-[3-(3-methyl[1,2,4]oxadiazol-5-yl)-[1,2,4]triazolo[3,4-α]phthalazin-6-yloxymethyl]-[1,2,4]triazol-1-yl}ethyl)amine;
dimethyl{1-methyl-5-[3-(5-methylisoxazol-3-yl)-[1,2,4]triazolo[3,4-α]phthalazin-6-yloxymethyl]-1H-[1,2,4]triazol-3-ylmethyl}amine;
N-ethyl(1-{1-methyl-5-({[3-(5-methylisoxazol-3-yl)[1,2,4]triazolo[3,4-α]phthalazin-6-yl]oxy}methyl)-1H-[1,2,4]triazol-3-yl]ethylamine;

or a pharmaceutically acceptable salt thereof.

4. The compound of claim 1 wherein A is $C_{1-2}$alkylidene optionally substituted by one or two hydroxy or $C_{1-2}$alkyl groups.

5. The compound of claim 1 wherein $R^{20}$ and $R^{21}$ are independently selected from hydrogen, $C_{1-6}$alkyl, amino $C_{1-6}$alkyl, $C_{1-6}$alkylamino$C_{1-6}$alkyl, di($C_{1-6}$alkyl)amino $C_{1-6}$alkyl and phenyl $C_{1-6}$alkyl or $R^{20}$ and $R^{21}$, together with the nitrogen atom to which they are attached, form an azetidinyl, piperidinyl, piperazinyl or morpholinyl ring or a 5 or 6 membered heteroaromatic ring containing 1, 2 or 3 further heteroatoms selected from the group consisting of O, N and S, provided that no more than one of the heteroatoms is O or S, the heteroaromatic ring being optionally substituted by $C_{1-4}$alkyl.

6. The compound of claim 2 of the formula
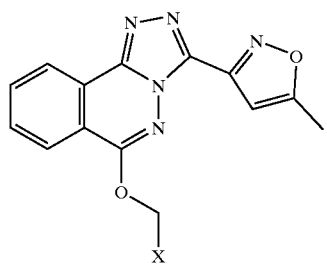
wherein X is selected from the group consisting of the substituents listed in the following table:
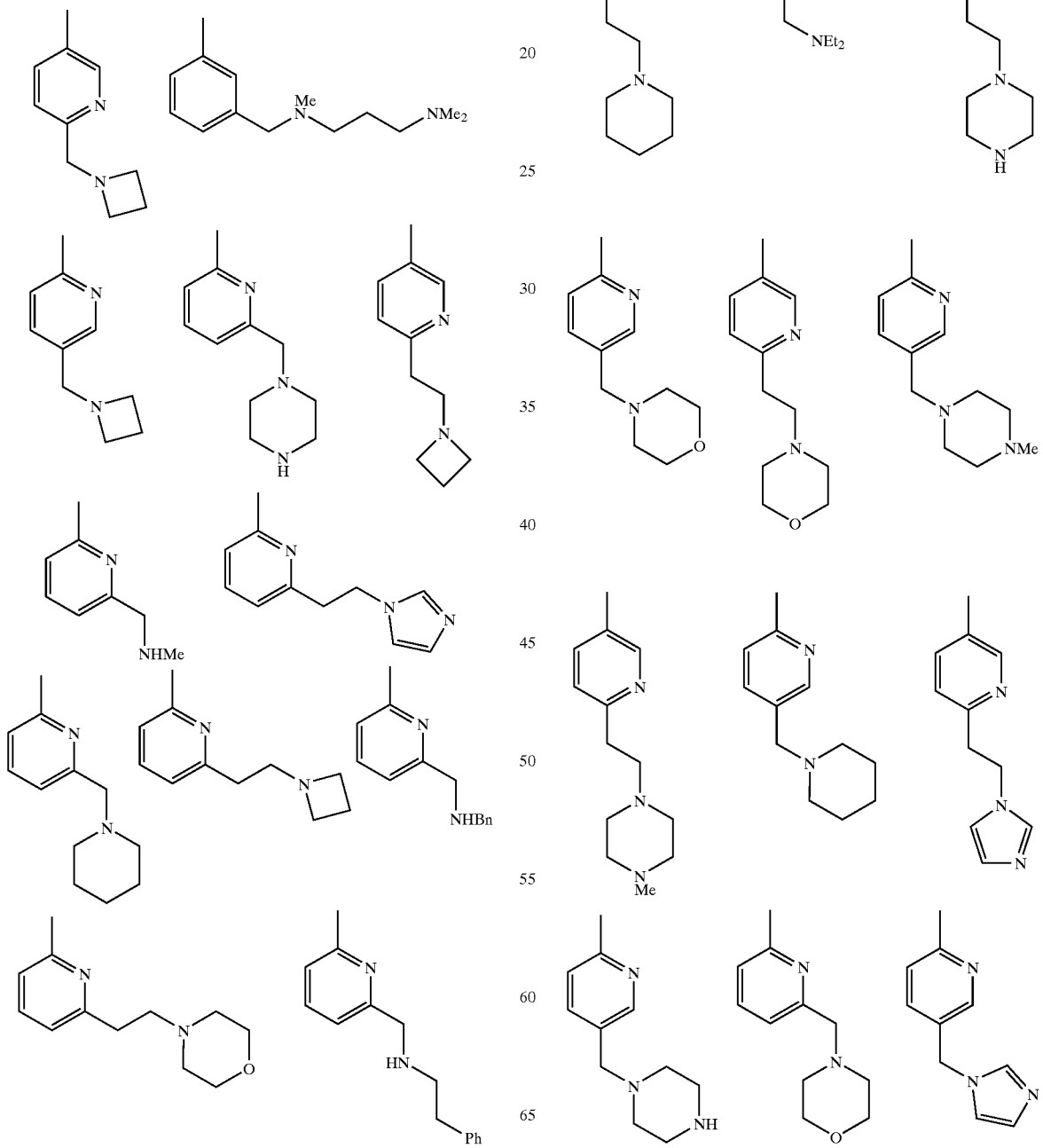

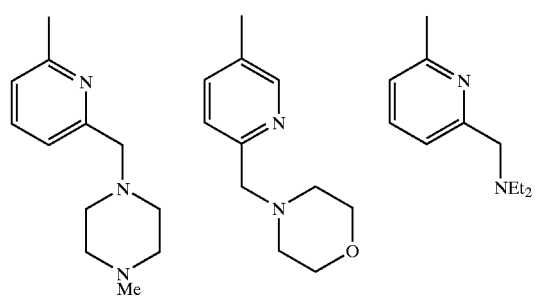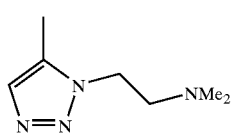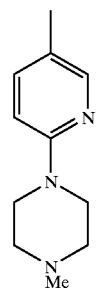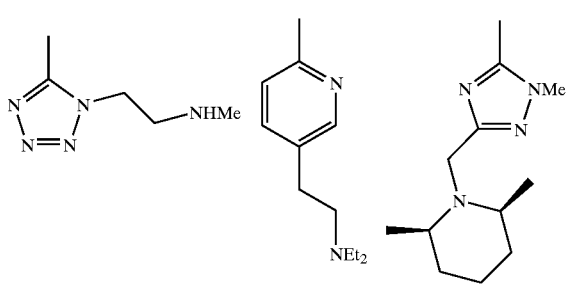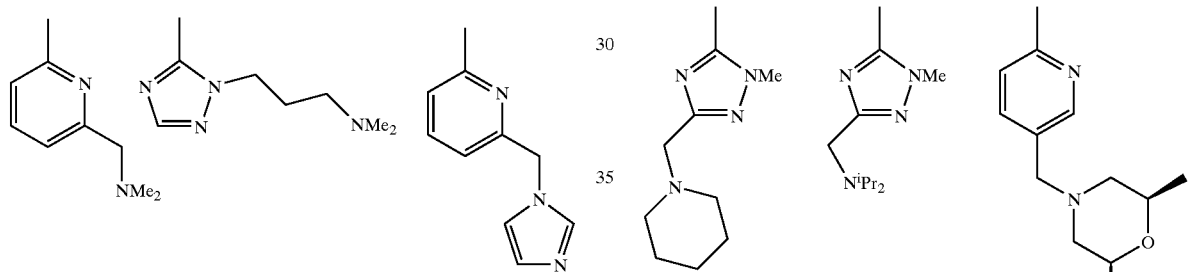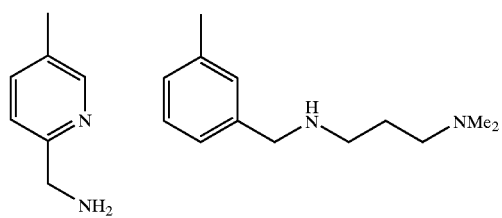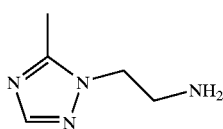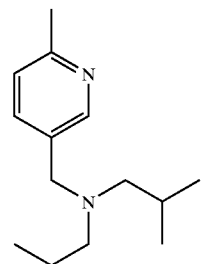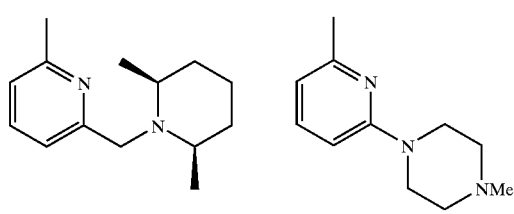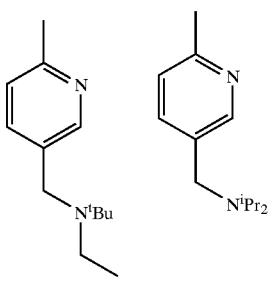

-continued
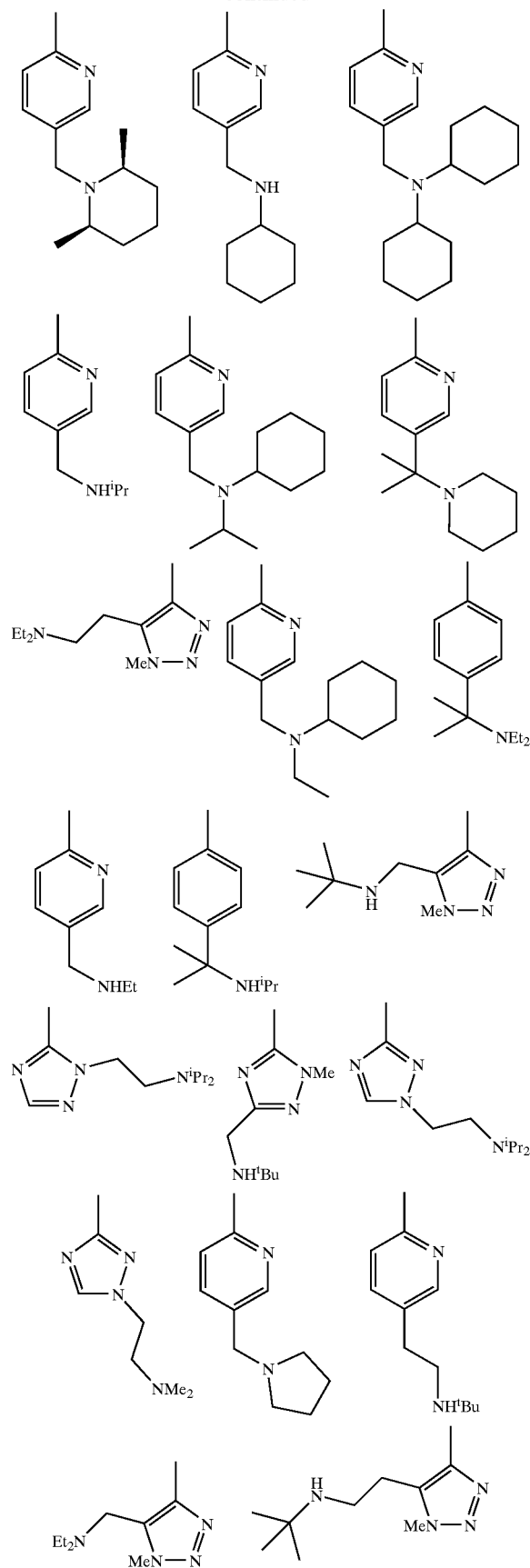
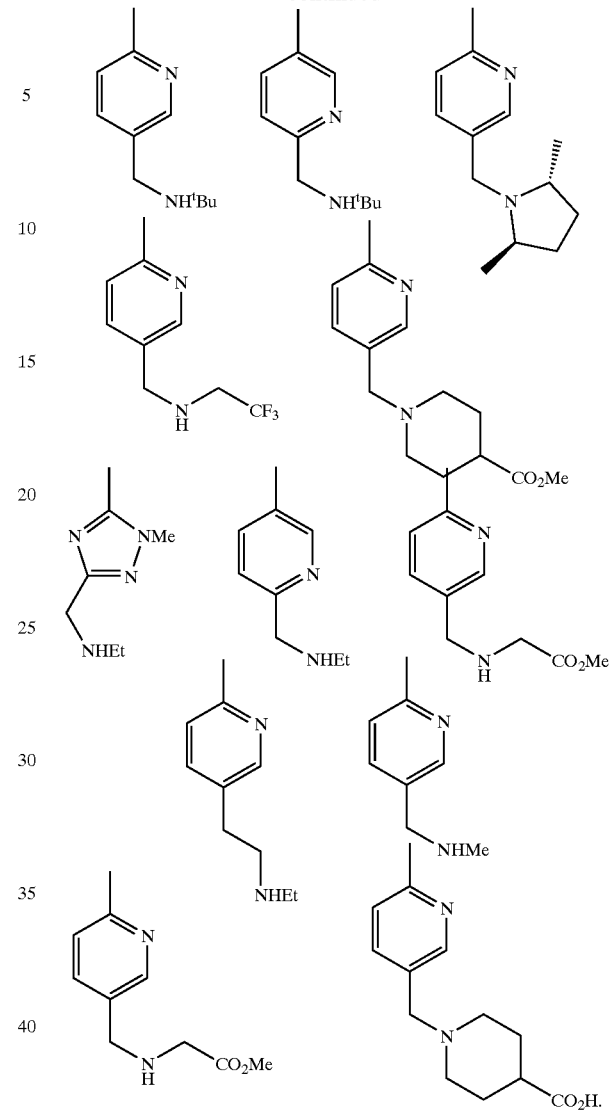
7. The compound of claim 5 of the formula
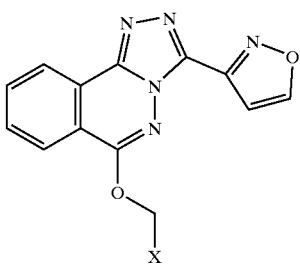
wherein X is selected from the group consisting of
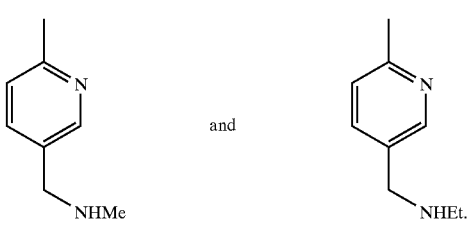

8. The compound of claim 5 which is

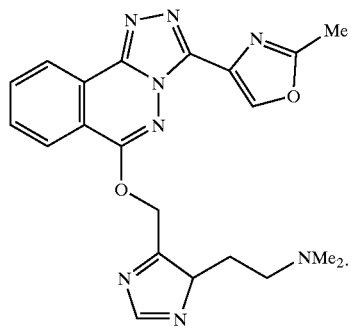

9. A pharmaceutical composition comprising a compound of formula I as defined in claim 1 or a pharmaceutically acceptable salt thereof and a pharmaceutically acceptable carrier.

10. A method of treating an individual suffering from a cognition deficit which comprises administering to that individual a therapeutically effective amount of a compound of formula I as defined in claim 1 or a pharmaceutically acceptable salt thereof.

* * * * *